United States Patent
Doi et al.

(10) Patent No.: US 10,563,234 B2
(45) Date of Patent: Feb. 18, 2020

(54) METHOD FOR PRODUCING L-AMINO ACIDS

(71) Applicant: AJINOMOTO CO., INC., Tokyo (JP)

(72) Inventors: Hidetaka Doi, Kanagawa (JP); Akiko Matsudaira, Kanagawa (JP); Yoshihiro Usuda, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 71 days.

(21) Appl. No.: 15/361,645

(22) Filed: Nov. 28, 2016

(65) Prior Publication Data

US 2017/0073714 A1    Mar. 16, 2017

Related U.S. Application Data

(63) Continuation of application No. PCT/JP2015/066072, filed on Jun. 3, 2015.

(30) Foreign Application Priority Data

Jun. 3, 2014 (JP) .................................. 2014-114799

(51) Int. Cl.
*C12P 13/04* (2006.01)
*C12P 13/08* (2006.01)

(52) U.S. Cl.
CPC .................................. *C12P 13/08* (2013.01)

(58) Field of Classification Search
CPC .......................................... C12P 13/04–13/24
See application file for complete search history.

(56) References Cited

U.S. PATENT DOCUMENTS

| | | |
|---|---|---|
| 5,168,056 A | 12/1992 | Frost |
| 5,776,736 A | 7/1998 | Frost et al. |
| 5,906,925 A | 5/1999 | Liao |
| 8,510,053 B2 | 8/2013 | Nishio et al. |
| 8,551,741 B2 | 10/2013 | Usuda et al. |
| 8,728,772 B2 | 5/2014 | Suzuki et al. |
| 8,932,834 B2 | 1/2015 | Doi et al. |
| 8,951,760 B2 | 2/2015 | Doi et al. |
| 8,975,045 B2 | 3/2015 | Doi et al. |
| 2009/0203090 A1 | 8/2009 | Ptitsyn et al. |
| 2009/0246835 A1 | 10/2009 | Iwatani et al. |
| 2010/0190217 A1 | 7/2010 | Doi et al. |
| 2011/0244529 A1 | 10/2011 | Claes et al. |
| 2013/0005000 A1 | 1/2013 | Doi et al. |
| 2013/0260425 A1 | 10/2013 | Doi et al. |
| 2014/0065697 A1 | 3/2014 | Zhang et al. |
| 2015/0203881 A1 | 7/2015 | Ptitsyn et al. |
| 2015/0259717 A1 | 9/2015 | Hara et al. |

FOREIGN PATENT DOCUMENTS

| | | | |
|---|---|---|---|
| CN | 103173504 A | 6/2013 | |
| EP | 2192170 A1 | 6/2010 | |
| EP | 2290092 A1 | 3/2011 | |
| JP | 2014-506466 A | 3/2014 | |
| WO | WO-03076629 A2 * | 9/2003 | ........... C12N 9/0008 |
| WO | WO2008/010565 A2 | 1/2008 | |
| WO | WO2009/031565 A1 | 3/2009 | |
| WO | WO2010/101053 A1 | 9/2010 | |
| WO | WO2011/096554 A1 | 8/2011 | |
| WO | WO2012/002486 A1 | 1/2012 | |
| WO | WO2012/077739 A1 | 6/2012 | |

OTHER PUBLICATIONS

Zhou et al., Cell Mol Life Sci 63:2260-2290, 2006 (Year: 2006).*
Kozak, M., Gene 234:187-208, 1999 (Year: 1999).*
UniProt Database Accession No. P25516, May 2014, 4 pages (Year: 2014).*
UniProt Database Accession No. P36683, May 2014, 5 pages (Year: 2014).*
Uni Prot Database Accession No. P37685, May 2014, 3 pages (Year: 2014).*
Schendel, P., "Current Protocols in Molecular Biology" (1998) 16.1.1-16.1.3 (Year: 1998).*
Tang et al., Microbiology 148:1027-1037, 2002 (Year: 2002).*
International Search Report for PCT Patent App. No. PCT/JP2015/066072 (dated Aug. 4, 2015).
Ho, K. K., et al., "Isolation and Characterization of an Aldehyde Dehydrogenase Encoded by the aldB Gene of *Escherichia coli*," J. Bacteriol. 2005;187:1067-1073.
Cunningham, L., et al., "Transcriptional regulation of the aconitase genes (acnA and acnB) of *Escherichia coli*," Microbiol. 1997;143:3795-3805.
International Preliminary Report on Patentability for PCT Patent App. No. PCT/JP2015/066072 (dated Dec. 15, 2016).
Supplementary European Search Report for European Patent App. No. 15803550.1 (dated Oct. 19, 2017).

* cited by examiner

*Primary Examiner* — David Steadman
(74) *Attorney, Agent, or Firm* — Cermak Nakajima & McGowan LLP; Shelly Guest Cermak

(57) ABSTRACT

A method for producing an L-amino acid is provided. An L-amino acid is produced by culturing a bacterium belonging to the family Enterobacteriaceae and having an L-amino acid-producing ability, wherein the bacterium has been modified so that the activity of aconitase is increased, or the activities of aconitase and acetaldehyde dehydrogenase are increased, in a medium, and collecting the L-amino acid from the medium or cells of the bacterium.

12 Claims, 5 Drawing Sheets

Specification includes a Sequence Listing.

Fig. 1A

```
E.coli          1:MTNNPPSAQIKPGEYGFPLKLKARYDNFIGGEWVAPADGEYYQNLTPVTGQLLCEVASSG 60
 (SEQ ID NO:38)
P.ananatis      1:-------MRYAHPGTPGALVTFKSAYGNYIDGKFIEPLSGEYFMNTSPVNGSDIARFPRSD 54
 (SEQ ID NO:40)
P.atrosepticum  1:MAHDNLEGRSAFGEVG-SLDLKKRYDNFIGGTWVPPDAGQYFVNLTPVTGQPMCEVASSS 59
 (SEQ ID NO:42)
S.enterica      1:MTNNPPSTRIQPSEYGYPLKLKARYDNFIGGDWVAPADGEYYQNLTPVTGQPLCEVASSG 60
 (SEQ ID NO:44)
                   ...  *  . * ,*,*,*,*  ., *  *,*  *, ,**,*,   ,....*

E.coli          61:KRDIDLALDAAHKVKDKWAHTSVQDRAAILFKIADRMEQNLELLATAETWDNGKPIRETS 120
P.ananatis      55:ARDIDLALDAAHRAAEAWGKTSVQTRSNLLLQVADRIDANLETLAVAESWDNGKPIRETL 114
P.atrosepticum  60:TRDIDHALDAAHKAKAEWGGLSVQERALVLNRIADRMEQNLERLAGVETWDNGKPIRETS 119
S.enterica      61:KKDIDLALDAAHKAKDKWAHTSVQDRAAILFKIADRMEQNLELLATAETWDNGKPIRETS 120
                   ,*,****,.. *  ,*** *,  *  ,*,,,* ** ,*,**********, E.coli          121:AADVPLAIDHFRYFASCIRAQEGGISEVDSETVAYHFHEPLGVVGQIIPWNFPLLMASWK 180
P.ananatis      115:NADLPLAADHFRYFAGCLRAQEGSTGEIDEKTVAYHFHEPLGVVGQIIPWNFPLLMAAWK 174
P.atrosepticum  120:GADVPLAIDHFRYFAACIRAQEGAISEIDGDTVAYHFHEPLGVVAQIIPWNFPLLMACWK 179
S.enterica      121:AADIPLAIDHFRYFASCIRAQEGGISEVDSETVAYHFHEPLGVVGQIIPWNFPLLMASWK 180
                   ** ***,****** *,***** ,,* * ,************** ,*********** **

E.coli          181:MAPALAAGNCVVLKPARLTPLSVLLLMEIVGDLLPPGVVNVVNGAGGVIGEYLATSKRIA 240
P.ananatis      175:LAPALAAGNCVVLKPAEQTPLGITLLMEMIGDLFPAGVLNVVQGFGREAGEALATSKRIA 234
P.atrosepticum 180:MAPALAAGNCIVLKPAKLTPMSVLILMELIQDLLPAGVINVVNGSGSEIGEYLATSKRVA 239
S.enterica      181:MAPALAAGNCVVLKPARLTPLSVLLLMEVIGDLLPPGVVNVVNGAGGEIGEYLATSKRIA 240
                    ********** ***** ,**,,..,*** , **,* ** ***,* *  ,**,******,*

E.coli          241:KVAFTGSTEVGQQIMQYATQNIIPVTLELGGKSPNIFFADVMDEEDAFFDKALEGFALFA 300
P.ananatis      235:KIAFTGSTPVGRHIMACAAENIIPCTVELGGKSPNIYFADIMNGEPDFIDKAVEGLVLGF 294
P.atrosepticum 240:KVAFTGSTEVGQQIMSYAAQNVTPVTLELGGKSPNIFFADVMDKEDSFFDKALEGFTLFA 299
S.enterica      241:KVAFTGSTEVGQQIMQYATQNIIPVTLELGGKSPNIFFADVMDEEDAFFDKALEGFALFA 300
                    *,******,**,,** ,*,*  *,*,********,***,*, * ,*,***,**, *,,
```

Fig. 1B

```
E.coli         301:FNQGEVCTCPSRALVQESIYERFMERAIRRVESIRSGNPLDSVTQMGAQVSHGQLETILN 360
P.ananatis     295:FNQGEVCTCPSRALIHESVYAPFMERVMAKVATIRRGDPLDTDTMIGAQASRQQFDKILS 354
P.atrosepticum 300:FNQGEVCTCPSRALVQESIYDRFMERAIKRVEAIRIGNPLDSKTMMGAQVSAGQLETILN 359
S.enterica     301:FNQGEVCTCPSRALVQESIYERFMERAIRRVESIRSGNPLDSGTQMGAQVSHGQLETILN 360
                  ************* ** * ****   * ** * ***  * *** *  * *   **

E.coli         361:YIDIGKKEGADVLTGGRRKLLEGELKDGYYLEPTILFGQNNMRVFQEEIFGPVLAVTTFK 420
P.ananatis     355:YIEIARNEGGEILTGGERALISSELDNGFYIQPTLIKGSNSMRCFQEEIFGPVIGITTFK 414
P.atrosepticum 360:YIDIGKKEGARVLTGGQRKAMPGGLAEGYYLEPTILFGKNSMRVFQEEIFGPVLAVTTFK 419
S.enterica     361:YIDIGKKEGADILTGGRRKELDGELKEGYYLEPTILFGKNNMRVFQEEIFGPVLAVTTFK 420
                  ** *   **   **** *     *   * * * ***   * ** ********   ****

E.coli         421:TMEEALELANDTQYGLGAGVWSRNGNLAYKMGRGIQAGRVWTNCYHAYPAHAAFGGYKQS 480
P.ananatis     415:DEAEALRIANETQFGLGAGVWTRDSNLAYRMGRAIKAGRVWTNCYHIYPAHAAFGGYKQS 474
P.atrosepticum 420:TMEDALEIANDTEYGLGAGVWSRNGNVAYRMGRGIQAGRVWTNCYHAYPAHAAFGGYKQS 479
S.enterica     421:TMEKALEIANDTQYGLGAGVWSRNGNLAYKMGRGIQAGRVWTNCYHAYPAHAAFGGYKQS 480
                     ** ** * ******* * *  ** *** * ********** *************

E.coli         481:GIGRETHKMMLEHYQQTKCLLVSYSDKPLGLF                             512
P.ananatis     475:GVGRETHKMALNQYQQTKNLLVSYDTAPLGLF                             506
P.atrosepticum 480:GIGRENHKMMLDHYQQTKCLLVSYSDKPMGLF                             511
S.enterica     481:GIGRETHKMMLEHYQQTKCLLVSYSDKPLGLF                             512
                  * *** *** * ***** ***** ***  ***
```

Fig. 2A

```
E.coli           1:MAVTNVAELNALVERVKKAQREYASFTQEQVDKIFRAAALAAADARIPLAKMAVAESGMG 60
  (SEQ ID NO:46)
P.ananatis       1:MAVTNVAELNALVERVKKAQQEFANFSQQQVDAIFRAAALAAADARIPLAKMAVAESGMG 60
  (SEQ ID NO:48)
P.atrosepticum   1:MAVTNVAELNALVERVKKAQQEFATYTQEQVDKIFRAAALAASDARIPLAKMAVAESGMG 60
  (SEQ ID NO:50)
S.enterica       1:MAVTNVAELNALVERVKKAQREYASFTQEQVDKIFRAAALAAADARIPLAKMAVAESGMG 60
  (SEQ ID NO:52)
                   *********************  *  * .. *. ***.********* ****************

E.coli          61:IVEDKVIKNHFASEYIYNAYKDEKTCGVLSEDDTFGTITIAEPIGIICGIVPTTNPTSTA 120
P.ananatis      61:IVEDKVIKNHFASEYIYNAYKDEKTCGVLDTDDTFGTITIAEPIGLICGIVPTTNPTSTA 120
P.atrosepticum  61:IVEDKVIKNHFASEYIYNAYQDEKTCGVLSTDDTFGTITIAEPIGLICGIVPTTNPTSTA 120
S.enterica      61:IVEDKVIKNHFASEYIYNAYKDEKTCGVLSEDDTFGTITIAEPIGIICGIVPTTNPTSTA 120
                   ********************. *******. *************** ************

E.coli         121:IFKSLISLKTRNAIIFSPHPRAKDATNKAADIVLQAAIAAGAPKDLIGWIDQPSVELSNA 180
P.ananatis     121:IFKALISLKTRNGIIFSPHPRAKDATNKAADIVLQAAIAAGAPKDIIGWIDAPSVELSNQ 180
P.atrosepticum 121:IFKALISLKTRNGIIFSPHPRAKNATNKAADIVLQAAIAAGAPKDIIGWIDQPSVDLSNQ 180
S.enterica     121:IFKSLISLKTRNAIIFSPHPRAKEATNKAADIVLQAAIAAGAPKDLIGWIDQPSVELSNA 180
                   *** ******** ********** *********************..*****.*** ***

E.coli         181:LMHHPDINLILATGGPGMVKAAYSSGKPAIGVGAGNTPVVIDETADIKRAVASVLMSKTF 240
P.ananatis     181:L-HHPDINLILATGGPGMVKAAYSSGKPAIGVGAGNTPVVIDETADVKRAVASILMSKTF 239
P.atrosepticum 181:LMHHPDINLILATGGPGMVKAAYSSGKPAIGVGAGNTPVVIDETADIKRAVASILMSKTF 240
S.enterica     181:LMHHPDINLILATGGPGMVKAAYSSGKPAIGVGAGNTPVVIDETADIKRAVASVLMSKTF 240
                   *. ************************************************. ****** ******

E.coli         241:DNGVICASEQSVVVVDSVYDAVRERFATHGGYLLQGKELKAVQDVILKNGALNAAIVGQP 300
P.ananatis     240:DNGVICASEQSVIVVDAVYDAVRERFASHGGYLLQGQELSAVQNIILKNGGLNAAIVGQP 299
P.atrosepticum 241:DNGVICASEQSVIVVDSAYDAVRERFATHGGYMLKGKELHAVQGILLKNGSLNADIVGQP 300
S.enterica     241:DNGVICASEQSVVVVDSVYDAVRERFASHGGYMLQGQELKAVQNVILKNGALNAAIVGQP 300
                   ************ ***. ******** **** * *.** ***  .**** ***.*****
```

Fig. 2B

```
E.coli         301:AYKIAELAGFSVPENTKILIGEVTVVDESEPFAHEKLSPTLAMYRAKDFEDAVEKAEKLV 360
P.ananatis     300:AVKIAEMAGISVPGETKILIGEVERVDESEPFAHEKLSPTLAMYRAKDYQDAVSKAEKLV 359
P.atrosepticum 301:APKIAEMAGITVPANTKVLIGEVTAVDESEPFAHEKLSPTLAMYRAKDFNDAVIKAEKLV 360
S.enterica     301:AYKIAELAGFSVPETTKILIGEVTVVDESEPFAHEKLSPTLAMYRAKDFEEAVEKAEKLV 360
                   * **** ** ** **.***** .********************. .** ******

E.coli         361:AMGGIGHTSCLYTDQDNQPARVSYFGQKMKTARILINTPASQGGIGDLYNFKLAPSLTLG 420
P.ananatis     360:AMGGIGHTSCLYTDQDNQTARVHYFGDKMKTARILINTPASQGGIGDLYNFKLAPSLTLG 419
P.atrosepticum 361:AMGGIGHTSCLYTDQDNQPERVNHFGNMMKTARILINTPASQGGIGDLYNFKLAPSLTLG 420
S.enterica     361:AMGGIGHTSCLYTDQDNQPERVAYFGQMMKTARILINTPASQGGIGDLYNFKLAPSLTLG 420
                   ******************. ** .** ********************************

E.coli         421:CGSWGGNSISENVGPKHLINKKTVAKRAENMLWHKLPKSIYFRRGSLPIALDEVITDGHK 480
P.ananatis     420:CGSWGGNSISENVGPKHLINKKTVAKRAENMLWHKLPKSIYFRRGSLPIALEEIATDGAK 479
P.atrosepticum 421:CGSWGGNSISENVGPKHLINKKTVAKRAENMLWHKLPKSIYFRRGSLPIALEEVASDGAK 480
S.enterica     421:CGSWGGNSISENVGPKHLINKKTVAKRAENMLWHKLPKSIYFRRGSLPIALDEVITDGHK 480
                   *********************************************** *. .** *

E.coli         481:RALIVTDRFLFNNGYADQITSVLKAAGVETEVFFEVEADPTLSIVRKGAELANSFKPDVI 540
P.ananatis     480:RAFVVTDRFLFNNGYADQVTRVLKSHGIETEVFFEVEADPTLSIVRKGAEQMNSFKPDVI 539
P.atrosepticum 481:RAFIVTDRFLFNNGYVDQVTSVLKQHGLETEVFFEVEADPTLSIVRKGAEQMHSFKPDVI 540
S.enterica     481:RALIVTDRFLFNNGYADQITSVLKAAGVETEVFFEVEADPTLSVVRKGAELANSFKPDVI 540
                   ** .***********.** *.***  * ****************.****** .******

E.coli         541:IALGGGSPMDAAKIMWVMYEHPETHFEELALRFMDIRKRIYKFPKMGVKAKMIAVTTTSG 600
P.ananatis     540:IALGGGSPMDAAKIMWVMYEHPETHFEELALRFMDIRKRIYKFPKMGVKARMVAITTTSG 599
P.atrosepticum 541:IALGGGSPMDAAKIMWVMYEHPTTHFEELALRFMDIRKRIYKFPKMGVKAKMVAITTTSG 600
S.enterica     541:IALGGGSPMDAAKIMWVMYEHPETHFEELALRFMDIRKRIYKFPKMGVKAKMIAVTTTSG 600
                   *********************. *********************** * * *****
```

Fig. 2C

```
E. coli          601:TGSEVTPFAVVTDDATGQKYPLADYALTPDMAIVDANLVMDMPKSLCAFGGLDAVTHAME 660
P. ananatis      600:TGSEVTPFAVVTDDATGQKYPLADYALTPDMAIVDANLVMDMPRSLCAFGGLDAVTHALE 659
P. atrosepticum  601:TGSEVTPFAVVTDDATGQKYPLADYALTPDMAIVDANLVMNMPKSLCAFGGLDAVTHSLE 660
S. enterica      601:TGSEVTPFAVVTDNATGQKYPLADYALTPDMAIVDANLVMDMPKSLCAFGGLDAVTHALE 660
                     *************.***********************.**.*************..*

E. coli          661:AYVSVLASEFSDGQALQALKLLKEYLPASYHEGSKNPVARERVHSAATIAGIAFANAFLG 720
P. ananatis      660:AYVSVLANEYSDGQALQALKLLKENLPASYAEGAKNPVARERVHNAATIAGIAFANAFLG 719
P. atrosepticum  661:AYVSVLANEYSDGQALQALKLLKENLPDSYRDGAKNPVARERVHNAATIAGIAFANAFLG 720
S. enterica      661:AYVSVLASEFSDGQALQALKLLKENLPASYHEGSKNPVARERVHSAATIAGIAFANAFLG 720
                     ******.*.*************.**.**..*.**********.****************

E. coli          721:VCHSMAHKLGSQFHIPHGLANALLICNVIRYNANDNPTKQTAFSQYDRPQARRRYAEIAD 780
P. ananatis      720:VCHSMAHKLGSEFHIPHGLANSLLISNVIRYNANDNPTKQTAFSQYDRPQARRRYAEIAD 779
P. atrosepticum  721:VCHSMAHKLGSEFHIPHGLANAMLISNVIRYNANDNPTKQTTFSQYDRPQARRRYAEIAD 780
S. enterica      721:VCHSMAHKLGSQFHIPHGLANALLICNVIRYNANDNPTKQTAFSQYDRPQARRRYAEIAD 780
                     ***********.*********..**.*********************************

E. coli          781:HLGLSAPGDRTAAKIEKLLAWLETLKAELGIPKSIREAGVQEADFLANVDKLSEDAFDDQ 840
P. ananatis      780:HLGLTAPGDRTAQKIEKLLVWLDEIKTELGIPASIREAGVQEADFLAKVDKLADDAFDDQ 839
P. atrosepticum  781:HLRLTAPSDRTAQKIEKLLNWLEEIKTELGIPASIREAGVQEADFLAKVDKLSEDAFDDQ 840
S. enterica      781:HLGLSAPGDRTAAKIEKLLAWLESIKAELGIPKSIREAGVQEADFLAHVDKLSEDAFDDQ 840
                     **.*.**.****.******.**..*.******.**************.****.******

E. coli          841:CTGANPRYPLISELKQILLDTYYGRDYVEGETAAKKE-AAPAKAEKKAKKSA----     891
P. ananatis      840:CTGANPRYPLIAELKQLMLDSYYGRKFVEPFASAAEAAQAQPVSDSKAAKKAKKA      894
P. atrosepticum  841:CTGANPRYPLISELKQILLDTYYGRKFSEEVKTETVEPVAKAAKTGKKAAH----      891
S. enterica      841:CTGANPRYPLISELKQILLDTYYGRDFTEGEVAAKKDVVAAPKAEKKAKKSA---      892
                     ***********.****..**.****..*    .    *    *...
```

METHOD FOR PRODUCING L-AMINO ACIDS

This application is a Continuation of, and claims priority under 35 U.S.C. § 120 to, International Application No. PCT/JP2015/066072, filed Jun. 3, 2015, and claims priority therethrough under 35 U.S.C. § 119 to Japanese Patent Application No. 2014-114799, filed Jun. 3, 2014, the entireties of which are incorporated by reference herein. Also, the Sequence Listing filed electronically herewith is hereby incorporated by reference (File name: 2016-11-28T_US-558_Seq_List; File size: 158 KB; Date recorded: Nov. 28, 2016).

BACKGROUND OF THE INVENTION

Field of the Invention

The present invention relates to a method for producing an L-amino acid utilizing a bacterium. L-amino acids are industrially useful as additives for animal feeds, ingredients of seasonings, ingredients of foods and drinks, amino acid infusions, and so forth.

Brief Description of the Related Art

L-Amino acids are industrially produced by, for example, fermentation using various microorganisms having an L-amino acid-producing ability. Examples of such methods for producing an L-amino acid by fermentation include, for example, methods of using a wild-type microorganism (wild-type strain), methods of using an auxotrophic strain derived from a wild-type strain, methods of using a metabolic regulation mutant strain derived from a wild-type strain as a mutant strain resistant to any of various drugs, and methods of using a strain having properties as both auxotrophic strain and metabolic regulation mutant strain.

In recent years, microorganisms in which an L-amino acid-producing ability is improved by recombinant DNA techniques are also utilized for production of L-amino acids. Examples of method for improving an L-amino acid-producing ability of a microorganism include, for example, enhancing the expression of a gene encoding an L-amino acid biosynthesis system enzyme (U.S. Pat. Nos. 5,168,056 and 5,776,736), and enhancing inflow of a carbon source into an L-amino acid biosynthesis system (U.S. Pat. No. 5,906,925).

In the conventional industrial production of objective substances such as L-amino acids by fermentation, glucose, fructose, sucrose, blackstrap molasses, starch hydrolysate, and so forth have been used as a carbon source.

It is also possible to use alcohols such as ethanol as a carbon source. As methods for producing an L-amino acid by fermentation using ethanol as a carbon source, there are known, for example, a method of using an Enterobacteriaceae bacterium modified so that it expresses alcohol dehydrogenase under aerobic conditions (WO2008/010565), a method of using an Enterobacteriaceae bacterium modified so that the activity of pyruvate synthase or pyruvate:NADP$^+$ oxidoreductase is increased (WO2009/031565), a method of using an Enterobacteriaceae bacterium modified so that the activity of ribonuclease G is reduced (WO2010/101053), a method of using an Enterobacteriaceae bacterium modified so that it harbors a mutant ribosome S1 protein (WO2011/096554), a method of using an Enterobacteriaceae bacterium modified so that the activity of an A1 dB protein is reduced (WO2012/002486), and a method of using an Enterobacteriaceae bacterium modified so that the intracellular concentration of hydrogen peroxide is reduced (Japanese Patent Laid-open (Kokai) No. 2014-036576).

Aconitase is a dehydratase/hydratase that reversibly catalyzes the isomerization between citrate and isocitrate in the TCA cycle or glyoxylate cycle (EC 4.2.1.3). *Escherichia coli* has at least two kinds of isozymes of aconitase, AcnA and AcnB. The identity of the amino acid sequences of AcnA and AcnB is about 17%. AcnB is the major aconitase of *Escherichia coli*, and is expressed especially in the logarithmic phase (Cunningham L1, Gruer M J, Guest J R., Microbiology., 1997, December; 143(12):3795-805). On the other hand, AcnA is induced by iron or oxidization stress, and is expressed especially in the resting stage (Ho K K, Weiner H., J. Bacteriol., 2005, February; 187(3): 1067-73).

Acetaldehyde dehydrogenase is an enzyme that reversibly catalyzes the reaction of generating acetic acid from acetaldehyde by using NAD$^+$ or NADP$^+$ as an electron acceptor (EC 1.2.1.3, EC 1.2.1.4, EC 1.2.1.5, EC 1.2.1.22, etc.). For example, the AldB protein of *Escherichia coli* has the acetaldehyde dehydrogenase activity that uses NADP$^+$ as an electron acceptor. As described above, it is known that a reduction of the activity of the AldB protein is effective for L-amino acid production using ethanol as a carbon source.

SUMMARY OF THE INVENTION

Aspects to be Achieved by the Invention

An aspect of the present invention is to develop a novel technique for improving an L-amino acid-producing ability of a bacterium, and thereby provide a method for efficiently producing an L-amino acid.

It has been found that by modifying a bacterium so that the activity of aconitase is increased, or both the activities of aconitase and acetaldehyde dehydrogenase are increased, L-amino acid production by the bacterium using ethanol as a carbon source can be improved.

It is an aspect of the present invention to provide a method for producing an L-amino acid, the method comprising (A) culturing an Enterobacteriaceae bacterium and having an L-amino acid-producing ability in a medium comprising ethanol, resulting in the production and accumulation of the L-amino acid in the medium or cells of the bacterium; and (B) collecting the L-amino acid from the medium or the cells, wherein the bacterium has been modified to increase the activity of aconitase, and wherein the aconitase is an AcnB protein.

It is a further aspect of the present invention to provide the method as described above, wherein the AcnB protein is selected from the group consisting of (a) a protein comprising the amino acid sequence of SEQ ID NO: 30, 32, 34, or 36; (b) a protein comprising the amino acid sequence of SEQ ID NO: 30, 32, 34, or 36, but wherein said sequence includes substitution, deletion, insertion, or addition of 1 to 10 amino acid residues, and said protein has aconitase activity; (c) a protein comprising an amino acid sequence having an identity of 90% or higher to the amino acid sequence of SEQ ID NO: 30, 32, 34, or 36, and wherein said protein has aconitase activity.

It is a further aspect of the present invention to provide a method for producing an L-amino acid, the method comprising (A) culturing an Enterobacteriaceae bacterium having an L-amino acid-producing ability in a medium comprising ethanol, resulting in production and accumulation of the L-amino acid in the medium or cells of the bacterium; and (B) collecting the L-amino acid from the medium or the cells, wherein the bacterium has been modified to increase the activities of aconitase and acetaldehyde dehydrogenase.

It is a further aspect of the present invention to provide the method as described above, wherein the aconitase is an AcnA protein or AcnB protein.

It is a further aspect of the present invention to provide the method as described above, wherein the AcnA protein is selected from the group consisting of (a) a protein comprising the amino acid sequence of SEQ ID NO: 22, 24, 26, or 28; (b) a protein comprising the amino acid sequence of SEQ ID NO: 22, 24, 26, or 28, but wherein said sequence includes substitution, deletion, insertion, or addition of 1 to 10 amino acid residues, and wherein said protein has aconitase activity; (c) a protein comprising an amino acid sequence having an identity of 90% or higher to the amino acid sequence of SEQ ID NO: 22, 24, 26, or 28, and wherein said protein has aconitase activity.

It is a further aspect of the present invention to provide the method as described above, wherein the AcnB protein is selected from the group consisting of (a) a protein comprising the amino acid sequence of SEQ ID NO: 30, 32, 34, or 36; (b) a protein comprising the amino acid sequence of SEQ ID NO: 30, 32, 34, or 36, but wherein said sequence includes substitution, deletion, insertion, or addition of 1 to 10 amino acid residues, and wherein said protein has aconitase activity; (c) a protein comprising an amino acid sequence having an identity of 90% or higher to the amino acid sequence of SEQ ID NO: 30, 32, 34, or 36, and wherein said protein has aconitase activity.

It is a further aspect of the present invention to provide the method as described above, wherein the acetaldehyde dehydrogenase is an AldB protein.

It is a further aspect of the present invention to provide the method as described above, wherein the AldB protein is selected from the group consisting of (a) a protein comprising the amino acid sequence of SEQ ID NO: 38, 40, 42, or 44; (b) a protein comprising the amino acid sequence of SEQ ID NO: 38, 40, 42, or 44, but wherein said sequence includes substitution, deletion, insertion, or addition of 1 to 10 amino acid residues, and wherein said protein has acetaldehyde dehydrogenase activity; (c) a protein comprising an amino acid sequence having an identity of 90% or higher to the amino acid sequence of SEQ ID NO: 38, 40, 42, or 44, and wherein said protein has acetaldehyde dehydrogenase activity.

It is a further aspect of the present invention to provide the method as described above, wherein the bacterium has been further modified to increase the activity of an ethanol metabolic enzyme.

It is a further aspect of the present invention to provide the method as described above, wherein the bacterium is able to aerobically utilize ethanol.

It is a further aspect of the present invention to provide the method as described above, wherein the bacterium has been modified to harbor a mutant adhE gene, and wherein the mutant adhE gene is encodes a mutant AdhE protein comprising a mutation that results in improved resistance to inactivation under aerobic conditions.

It is a further aspect of the present invention to provide the method as described above, wherein the mutation is replacement of an amino acid residue corresponding to the glutamic acid residue at position 568 in the amino acid sequence of SEQ ID NO: 46 with an amino acid residue other than glutamic acid and aspartic acid.

It is a further aspect of the present invention to provide the method as described above, wherein the amino acid residue other than glutamic acid and aspartic acid is lysine.

It is a further aspect of the present invention to provide the method as described above, wherein the mutant AdhE protein further has an additional mutation selected from the group consisting of (A) replacement of an amino acid residue corresponding to the glutamic acid residue at position 560 in the amino acid sequence of SEQ ID NO: 46 with another amino acid residue, (B) replacement of an amino acid residue corresponding to the phenylalanine residue at position 566 in the amino acid sequence of SEQ ID NO: 46 with another amino acid residue, (C) replacement of amino acid residues corresponding to the glutamic acid residue at position 22, methionine residue at position 236, tyrosine residue at position 461, isoleucine residue at position 554, and alanine residue at position 786 in the amino acid sequence of SEQ ID NO: 46 with other amino acid residues; and (D) combinations thereof.

It is a further aspect of the present invention to provide the method as described above, wherein the bacterium is an *Escherichia* bacterium.

It is a further aspect of the present invention to provide the method as described above, wherein the bacterium is *Escherichia coli*.

It is a further aspect of the present invention to provide the method as described above, wherein the L-amino acid is L-lysine.

It is a further aspect of the present invention to provide the method as described above, wherein the bacterium further has a characteristic selected from the group consisting of (A) the bacterium has been modified to increase the activity or activities of an enzymes selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyl-diaminopimelate deacylase, and combinations thereof (B) the bacterium has been modified to reduce the activity of lysine decarboxylase; and (C) combinations thereof.

BRIEF DESCRIPTION OF THE DRAWINGS

FIGS. 1A and 1B: Alignment of amino acid sequences of various AldB proteins

FIGS. 2A, 2B, and 2C: Alignment of amino acid sequences of various AldE proteins.

DESCRIPTION OF THE PREFERRED EMBODIMENTS

Hereafter, the present invention will be explained in detail.

The method of the present invention is a method for producing an L-amino acid by culturing an Enterobacteriaceae bacterium having an L-amino acid-producing ability in a medium containing ethanol resulting in production and accumulation of the L-amino acid in the medium or cells of the bacterium, and collecting the L-amino acid from the medium or the cells, wherein the bacterium has been modified so that the activity of aconitase is increased, or the activities of aconitase and acetaldehyde dehydrogenase are increased. The bacterium used for this method is also referred to as "the bacterium of the present invention".

<1> Bacterium of the Present Invention

The bacterium can belong to the family Enterobacteriaceae and also can have an L-amino acid-producing ability. The bacterium has been modified so that the activity of aconitase is increased, or the activities of aconitase and acetaldehyde dehydrogenase are increased.

<1-1> Bacterium Having L-Amino Acid-Producing Ability

The phrase "bacterium having an L-amino acid-producing ability" refers to a bacterium having an ability to generate or produce, and accumulate an objective L-amino acid in a medium or cells of the bacterium to such a degree that the L-amino acid can be collected, when the bacterium is cultured in the medium. The bacterium having an L-amino acid-producing ability may be able to accumulate an objective L-amino acid in a medium in an amount larger than that obtainable with a non-modified strain. Examples of the non-modified strain include a wild-type strain and parental strain. The bacterium having an L-amino acid-producing ability may be a bacterium that can accumulate an objective L-amino acid in a medium in an amount of 0.5 g/L or more, or 1.0 g/L or more.

Examples of the L-amino acid include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. The bacterium can have an ability to produce a single kind of L-amino acid, or two or more kinds of L-amino acids.

Amino acids may be L-amino acids unless otherwise stated. Furthermore, the L-amino acid to be produced may be in the form of a free compound, a salt, or a mixture of these forms. That is, the term "L-amino acid" can refer to an L-amino acid in a free form, its salt, or a mixture of these, unless otherwise stated. Examples of the salt will be described later.

Examples of bacteria belonging to the family Enterobacteriaceae include bacteria belonging to the genus *Escherichia, Enterobacter, Pantoea, Klebsiella, Serratia, Envinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov) can be used.

The *Escherichia* bacterial species are not particularly limited, and examples include species classified into the genus *Escherichia* according to the taxonomy known to those skilled in the field of microbiology. Examples of the *Escherichia* bacterium include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology, Second Edition, American Society for Microbiology Press, Washington, D.C.). Examples of the *Escherichia* bacterial species include, for example, *Escherichia coli*. Specific examples of *Escherichia coli* strains include, for example, *Escherichia coli* W3110 (ATCC 27325) and *Escherichia coli* MG1655 (ATCC 47076) derived from the prototype wild-type strain, K-12.

The *Enterobacter* bacteria are not particularly limited, and examples include species classified into the genus *Enterobacter* according to classification known to a person skilled in the art of microbiology. Examples of the *Enterobacter* bacterium include, for example, *Enterobacter agglomerans* and *Enterobacter aerogenes*. Specific examples of *Enterobacter agglomerans* strains include, for example, the *Enterobacter agglomerans* ATCC 12287. Specific examples of *Enterobacter aerogenes* strains include, for example, the *Enterobacter aerogenes* ATCC 13048, NBRC 12010 (Biotechnol Bioeng., 2007, Mar. 27; 98(2):340-348), and AJ110637 (FERM BP-10955). Examples the *Enterobacter* bacterial strains also include, for example, the strains described in European Patent Application Laid-open (EP-A) No. 0952221. In addition, *Enterobacter agglomerans* also include some strains classified as *Pantoea agglomerans*.

The *Pantoea* bacteria are not particularly limited, and examples include species classified into the genus *Pantoea* according to classification known to a person skilled in the art of microbiology. Examples of the *Pantoea* bacterial species include, for example, *Pantoea ananatis, Pantoea stewartii, Pantoea agglomerans*, and *Pantoea citrea*. Specific examples of *Pantoea ananatis* strains include, for example, the *Pantoea ananatis* LMG20103, AJ13355 (FERM BP-6614), AJ13356 (FERM BP-6615), AJ13601 (FERM BP-7207), SC17 (FERM BP-11091), and SC17(0) (VKPM B-9246). Some strains of *Enterobacter agglomerans* were recently reclassified into *Pantoea agglomerans, Pantoea ananatis, Pantoea stewartii*, or the like on the basis of nucleotide sequence analysis of 16S rRNA etc. (Int. J. Syst. Bacteriol., 43, 162-173 (1993)). The *Pantoea* bacteria include those reclassified into the genus *Pantoea* as described above.

Examples of the Envinia bacteria include Envinia *amylovora* and Envinia *carotovora*. Examples of the *Klebsiella* bacteria include *Klebsiella planticola*.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org/). The registration numbers of the strains are listed in the catalogue of the American Type Culture Collection.

The bacterium may be a bacterium inherently having an L-amino acid-producing ability, or may be a bacterium modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a typical mutagenesis treatment, and then selecting a strain exhibiting autotrophy, analogue resistance, or a metabolic regulation mutation, and having an L-amino acid-producing ability from the obtained mutant strains. Examples of typical mutagenesis treatments include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP 1010755 A, and so forth. The detailed procedures for enhancing enzyme activity will be described later.

Furthermore, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" includes an enzyme involved in decomposition of the objective amino acid. The method for reducing an enzyme activity will be described later.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability include, for example, a method of modifying a bacterium so that the bacterium has an increased activity or activities of one or more of the L-glutamic acid biosynthesis enzymes. Examples of such enzymes include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (OA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are genes encoding the enzymes (the same shall apply to the same occasions hereafter). It is preferable to enhance the activity or activities of one or more of, for example, glutamate dehydrogenase, citrate synthase, phosphoenol pyruvate carboxylase, and methylcitrate synthase.

Examples of strains belonging to the family Enterobacteriaceae and modified so that the expression of the citrate synthase gene, phosphoenolpyruvate carboxylase gene, and/or glutamate dehydrogenase gene are increased include those disclosed in EP 1078989 A, EP 955368 A, and EP 952221 A. Furthermore, examples of strains belonging to the family Enterobacteriaceae and modified so that the expression of a gene of the Entner-Doudoroff pathway (edd, eda) is increased include those disclosed in EP 1352966 B.

Examples of methods for imparting or enhancing L-glutamic acid-producing ability also include, for example, a method of modifying a bacterium so that the bacterium has a reduced activity or activities of one or more enzymes that catalyze a reaction branching away from the biosynthesis pathway of L-glutamine to generate a compound other than L-glutamic acid. Examples of such enzymes include, but are not particularly limited to, isocitrate lyase (aceA), α-ketoglutarate dehydrogenase (sucA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). It is preferable to reduce or delete, for example, the α-ketoglutarate dehydrogenase activity.

*Escherichia* bacteria having a reduced α-ketoglutarate dehydrogenase activity or deficient in the α-ketoglutarate dehydrogenase activity, and methods for obtaining them are described in U.S. Pat. Nos. 5,378,616 and 5,573,945. Furthermore, methods for reducing or deleting the α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, 8,129,151, and WO2008/075483. Specific examples of *Escherichia* bacteria having a reduced α-ketoglutarate dehydrogenase activity or deficient in the α-ketoglutarate dehydrogenase activity include the following strains.

*E. coli* W3110sucA::Km$^r$
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ is a strain obtained by disrupting the sucA gene encoding α-ketoglutarate dehydrogenase of *E. coli* W3110. This strain is completely deficient in the α-ketoglutarate dehydrogenase activity.

Examples of L-glutamic acid-producing bacteria and parental strains that can be used to derive such bacteria also include *Pantoea* bacteria, such as *Pantoea ananatis* AJ13355 (FERM BP-6614), *Pantoea ananatis* SC17 (FERM BP-11091), and *Pantoea ananatis* SC17(0) (VKPM B-9246). The AJ13355 strain is isolated from soil in Iwata-shi, Shizuoka-ken, Japan as a strain that can proliferate in a low pH medium containing L-glutamic acid and a carbon source. The SC17 strain is selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Furthermore, examples of L-glutamic acid-producing bacteria and parental strains that can be used to derive such bacteria also include *Pantoea* bacteria having a reduced α-ketoglutarate dehydrogenase activity or deficient in the α-ketoglutarate dehydrogenase activity. Examples of such strains include AJ13356 (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, they are referred to as *Pantoea ananatis* in this specification.

Furthermore, examples of L-glutamic acid-producing bacteria and parental strains that can be used to derive such bacteria also include *Pantoea* bacteria such as the *Pantoea ananatis* SC17sucA/RSFCPG+pSTVCB, *Pantoea ananatis* AJ13601, *Pantoea ananatis* NP106, and *Pantoea ananatis* NA1. The SC17sucA/RSFCPG+pSTVCB strain was obtained by introducing the plasmid RSFCPG containing the citrate synthase gene (gltA), phosphoenolpyruvate carboxylase gene (ppc), and glutamate dehydrogenase gene (gdhA) derived from *Escherichia coli*, and the plasmid pSTVCB containing the citrate synthase gene (gltA) derived from *Brevibacterium lactofermentum*, into the SC17sucA strain. The AJ13601 strain is selected from SC17sucA/RSFCPG+pSTVCB as a strain resistant to a high concentration of L-glutamic acid at a low pH. The NP106 strain was obtained from the AJ13601 strain by curing the RSFCPG and pSTVCB plasmids. The AJ13601 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Chiba-ken, 292-0818, Japan) on Aug. 18, 1999, and assigned an accession number FERM P-17516. Then, the deposit was converted to an international deposit under the provisions of the Budapest Treaty on Jul. 6, 2000, and assigned an accession number FERM BP-7207.

Examples of L-glutamic acid-producing bacteria and parental strains that can be used to derive such bacteria also include strains in which both the α-ketoglutarate dehydrogenase (sucA) activity and the succinate dehydrogenase (sdh) activity are reduced or deleted (Japanese Patent Laid-open (Kokai) No. 2010-041920). Specific examples of such strains include, for example, the sucAsdhA double-deficient strain of *Pantoea ananatis* NA1 (Japanese Patent Laid-open (Kokai) No. 2010-041920).

Examples of L-glutamic acid-producing bacteria and parental strains that can be used to derive such bacteria also include auxotrophic mutant strains. Specific examples of auxotrophic mutant strains include, for example, *E. coli* VL334thrC$^+$ (VKPM B-8961, EP 1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains that can be used to derive such bacteria also include strains having resistance to an aspartic acid analogue. Such strains can also be deficient in α-ketoglutarate dehydrogenase activity. Specific examples of strains having resistance to an aspartic acid analogue and deficient in the α-ketoglutarate dehydrogenase activity include, for example, *E. coli* AJ13199 (FERM BP-5807, U.S. Pat. No. 5,908,768), *E. coli* FFRM P-12379, which additionally has a lowered L-glutamic acid-decomposing ability (U.S. Pat. No. 5,393,671), and *E. coli* M13138 (FERM BP-5565, U.S. Pat. No. 6,110,714).

Examples of methods for imparting or enhancing L-glutamic acid-producing ability also include a method of modifying a bacterium so that the D-xylulose-5-phosphate phosphoketolase activity and/or the fructose-6-phosphate phosphoketolase activity are/is enhanced (Japanese Patent Laid-open (Kohyo) No. 2008-509661). Either one of the D-xylulose-5-phosphate phosphoketolase activity and the fructose-6-phosphate phosphoketolase activity may be enhanced, or both may be enhanced. In this specification, D-xylulose-5-phosphate phosphoketolase and fructose-6-phosphate phosphoketolase may be collectively referred to as phosphoketolase.

The D-xylulose-5-phosphate phosphoketolase activity means the conversion of xylulose-5-phosphate into glyceraldehyde-3-phosphate and acetyl phosphate while consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183: 2929-2936, 2001).

The fructose-6-phosphate phosphoketolase activity means conversion of fructose-6-phosphate into erythrose-4-phosphate and acetyl phosphate while consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001).

Examples of methods for imparting or enhancing L-glutamine-producing ability also include, for example, a method of enhancing the expression of the yhfK gene (WO2005/085419) or the ybjL gene (WO2008/133161), which is an L-glutamic acid secretion gene.

<L-Glutamine-Producing Bacteria>

Examples of methods for imparting or enhancing L-glutamine-producing ability include, for example, a method of modifying a bacterium so that the bacterium has an increased activity or activities of one or more of the L-glutamine biosynthesis enzymes. Examples of such enzymes include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP 1229121).

Examples of methods for imparting or enhancing L-glutamine-producing ability also include, for example, a method of modifying a bacterium so that the bacterium has a reduced activity or activities of one or more enzymes that catalyze a reaction branching away from the biosynthesis pathway of L-glutamine to generate a compound other than L-glutamine. Examples of such enzymes include, but are not particularly limited to, glutaminase.

Examples of L-glutamic acid-producing bacteria and parental strains that can be used to derive such bacteria include a strain belonging to the genus *Escherichia* and having a mutant glutamine synthetase in which the tyrosine residue of the position 397 is replaced with another amino acid residue (U.S. Patent Published Application No. 2003/0148474).

<L-Proline-Producing Bacteria>

Examples of methods for imparting or enhancing L-proline-producing ability include, for example, a method of modifying a bacterium so that the bacterium has an increased activity or activities of one or more kinds of enzymes selected from the L-proline biosynthesis enzymes. Examples of such enzymes include glutamate-5-kinase (proB), γ-glutamylphosphate reductase, and pyroline-5-carboxylate reductase (putA). For enhancing the activity of such an enzyme, for example, the proB gene encoding a glutamate kinase desensitized to feedback inhibition by L-proline (German Patent No. 3127361) can be preferably used.

Examples of methods for imparting or enhancing L-glutamine-producing ability also include, for example, a method of modifying a bacterium so that the bacterium has a reduced activity of an enzyme involved in decomposition of L-proline. Examples of such an enzyme include proline dehydrogenase and ornithine aminotransferase.

Specific examples of L-proline-producing bacteria and parental strains that can be used to derive such bacteria include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 (VKPM B-8011), which is a 3,4-dehydroxyproline and azetidine-2-carboxylate resistant strain, and *E. coli* 702ilvA (VKPM B-8012), which is an ilvA gene-deficient strain of the 702 strain (EP 1172433).

<L-Threonine-Producing Bacteria>

Examples of methods for imparting or enhancing L-threonine-producing ability include, for example, a method of modifying a bacterium so that the bacterium has an increased activity or activities of one or more of the L-threonine biosynthesis enzymes. Examples of such enzymes include, but are not particularly limited to, aspartokinase III (lysC), aspartate semialdehyde dehydrogenase (asci), aspartokinase I (thrA), homoserine kinase (thrB), threonine synthase (thrC), and aspartate aminotransferase (aspartate transaminase) (aspC). Among these enzymes, it is preferable to enhance activity or activities of one or more of aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed include, for example, *E. coli* TDH6, which is deficient in the threonine dehydrogenase activity (Japanese Patent Laid-open (Kokai) No. 2001-346578).

The activities of the L-threonine biosynthesis enzymes are inhibited by the endproduct, L-threonine. Therefore, to construct L-threonine-producing strains, the genes of the L-threonine biosynthesis enzymes can be modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, expression of the threonine operon can be enhanced by removing the leader sequence or the attenuator in the attenuation region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is located upstream of the threonine operon, and can be replaced with a non-native promoter (refer to WO98/04715). Also, the threonine operon may be constructed so that the threonine biosynthesis genes are expressed under the control of the repressor and promoter of λ-phage (European Patent No. 0593792). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

The expression amount of the threonine operon that is modified so as to be desensitized to feedback inhibition by L-threonine as described above can be increased in a host by increasing its copy number or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include rhtA (Res. Microbiol. 154:123-135 (2003)), rhtB (European Patent Laid-open No. 0994190), rhtC (European Patent Laid-open No. 1013765), yfiK, and yeaS (European Patent Laid-open No. 1016710). As for methods for imparting L-threonine resistance to a host, those described in European Patent Laid-open No. 0994190 and WO90/04636 are exemplary.

Specific examples of L-threonine-producing bacteria and parental strains that can be used to derive such bacteria include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP 1149911 A), and *E. coli* VKPM B-5318 (EP 0593792 B).

The VKPM B-3996 strain is obtained by introducing the plasmid pVIC40 into the TDH-6 strain. The TDH-6 strain has sucrose-assimilating ability, is deficient in the thrC gene, and the ilvA gene has a leaky mutation. This VKPM B-3996 strain also has a mutation in the rhtA gene, which imparts resistance to high concentrations of threonine or homoserine. The plasmid pVIC40 is a plasmid obtained by inserting the thrA*BC operon containing a mutant thrA gene encoding an aspartokinase-homoserine dehydrogenase I resistant to feedback inhibition by threonine and the wild-type thrBC genes into an RSF1010-derived vector (U.S. Pat. No. 5,705, 371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 in which the regulatory region of the threonine operon is replaced with the temperature-sensitive λ-phage Cl repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene, which encodes aspartokinase-homoserine dehydrogenase I of *E. coli*, has been elucidated (nucleotide numbers 337 to 2799, GenBank accession NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC_000913.2, gi: 49175990). The thrB gene is located between the thrA and thrC genes on the chromosome of *E. coli* K-12. The thrC gene, which encodes threonine synthase of *E. coli*, has been elucidated (nucleotide numbers 3734 to 5020, GenBank accession NC_000913.2, gi: 49175990). The thrC gene is located between the thrB gene and the yaaX open reading frame on the chromosome of *E. coli* K-12. The thrA*BC operon containing a mutant thrA gene which encodes an aspartokinase-homoserine dehydrogenase I resistant to feedback inhibition by threonine and the wild-type thrBC genes can be obtained from the well-known plasmid pVIC40, which is present in the threonine-producing strain *E. coli* VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated rhtA gene (rht: resistance to homoserine and threonine). It has also been revealed that the rhtA23 mutation that imparts resistance to high concentrations of threonine or homoserine is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif., Aug. 24-29, 1997, abstract No. 457; EP 1013765 A).

The asd gene of *E. coli* has already been elucidated (nucleotide numbers 3572511 to 3571408, GenBank accession NC_000913.1, gi:16131307), and can be obtained by PCR (refer to White, T. J., et al., Trends Genet, 5:185-189, 1989) utilizing primers prepared on the basis of the nucleotide sequence of the gene. The asd genes of other microorganisms can also be obtained in a similar manner.

The aspC gene of *E. coli* has also already been elucidated (nucleotide numbers 983742 to 984932, GenBank accession NC_000913.1, gi:16128895), and can be obtained by PCR utilizing primers prepared on the basis of the nucleotide sequence of the gene. The aspC genes of other microorganisms can also be obtained in a similar manner.

<L-Lysine-Producing Bacteria>

Examples of methods for imparting or enhancing L-lysine-producing ability include, for example, a method of modifying a bacterium so that the bacterium has an increased activity or activities of the L-lysine biosynthesis enzymes. Examples of such enzymes include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP 1253195 A). It is preferable to enhance the activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase. In addition, L-lysine-producing bacteria and parental strains that can be used to derive such bacteria can express an increased level of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme.

Examples of methods for imparting or enhancing L-lysine-producing ability also include, for example, a method of modifying a bacterium so that the bacterium has a reduced activity or activities of one or more of the enzymes that catalyze a reaction branching away from the biosynthetic pathway of L-lysine to generate a compound other than L-lysine. Examples of such enzymes include, but are not particularly limited to, homoserine dehydrogenase, lysine decarboxylase (U.S. Pat. No. 5,827,698), and malic enzyme (WO2005/010175).

Examples of L-lysine-producing bacteria and parental strains that can be used to derive such bacteria also include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parental strains that can be used to derive such bacteria include E. coli AJ11442 (FERM BP-1543, NRRL B-12185, see U.S. Pat. No. 4,346,170) and E. coli VL611. In these strains, aspartokinase is desensitized to feedback inhibition by L-lysine.

Specific examples of L-lysine-producing bacteria and parental strains that can be used to derive such bacteria also include the E. coli WC196 strain. The WC196 strain was bred by imparting AEC resistance to the W3110 strain, which was derived from E. coli K-12 (U.S. Pat. No. 5,827, 698). The WC196 strain was designated E. coli AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Preferred examples of L-lysine-producing bacteria include E. coli WC196ΔcadAΔldc and E. coli WC196ΔcadAΔldc/pCABD2 (WO2010/061890). The E. coli WC196ΔcadAΔldc strain is constructed from the WC196 strain by disrupting the cadA and ldcC genes encoding lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from Escherichia coli and encoding a dihydrodipicolinate synthase (DDPS) having a mutation for desensitization to feedback inhibition by L-lysine, a mutant lysC gene derived from Escherichia coli and encoding aspartokinase III having a mutation for desensitization to feedback inhibition by L-lysine, the dapB gene derived from Escherichia coli and encoding dihydrodipicolinate reductase, and the ddh gene derived from Brevibacterium lactofermentum and encoding diaminopimelate dehydrogenase.

Other examples of L-lysine-producing bacteria also include E. coli AJIK01 (NITE BP-01520). The AJIK01 strain was designated E. coli AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

<L-Arginine-Producing Bacteria>

Examples of methods for imparting or enhancing L-arginine-producing ability include, for example, a method of modifying a bacterium so that the bacterium has an increased activity or activities of one or more of the L-arginine biosynthesis enzymes. Examples of such enzymes include, but are not particularly limited to, N-acetylglutamate synthase (argA), N-acetylglutamyl phosphate reductase (argC), ornithine acetyl transferase (argJ), N-acetylglutamate kinase (argB), acetylornithine transaminase (argD), acetylornithine deacetylase (argE), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (European Patent Laid-open No. 1170361) can be used.

Specific examples of L-arginine-producing bacteria and parental strains that can be used to derive such bacteria include, for example, the E. coli 237 strain (VKPM B-7925) (U.S. Patent Published Application No. 2002/058315A1), derivative strains introduced with the argA gene encoding a mutant N-acetyl glutamate synthase (Russian Patent Application No. 2001112869, EP 1170361 A1), E. coli 382 strain derived from the 237 strain and having an improved acetic acid-assimilating ability (VKPM B-7926, EP 1170358 A1), and E. coli 382ilvA+ strain, which is a strain obtained from the 382 strain by introducing the wild-type ilvA gene from E. coli K-12 strain thereto. The E. coli strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The E. coli 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of L-arginine-producing bacteria and parental strains that can be used to derive such bacteria also include strains having resistance to amino acid analogues, and so forth. Examples of such strains include Escherichia coli mutant strains having resistance to α-methylmethionine, p-fluorophenylalanine, D-arginine, arginine hydroxamate, S-(2-aminoethyl)-cysteine, α-methylserine, β-2-thienylalanine, or sulfaguanidine (refer to Japanese Patent Laid-open (Kokai) No. 56-106598).

<L-Citrulline-Producing Bacteria and L-Ornithine-Producing Bacteria>

The biosynthetic pathways of L-citrulline and L-ornithine are common to that of L-arginine. Therefore, an ability to produce L-citrulline and/or L-ornithine can be imparted or enhanced by increasing the activity or activities of N-acetylglutamate synthase (argA), N-acetylglutamyl phosphate reductase (argC), ornithine acetyltransferase (argJ), N-acetylglutamate kinase (argB), acetylornithine transaminase (argD), and/or acetylornithine deacetylase (argE) (WO2006/35831).

<L-Histidine-Producing Bacteria>

Examples of methods for imparting or enhancing L-histidine-producing ability include, for example, a method of modifying a bacterium so that the bacterium has an increased activity or activities of one or more of the L-histidine biosynthesis enzymes. Examples of such enzymes include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2003677 and 2119536).

Specific examples of L-histidine-producing bacteria and parental strains that can be used to derive such bacteria include, for example, strains belonging to the genus *Escherichia*, such as the *E. coli* 24 strain (VKPM B-5945, RU 2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP 1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP 1016710 A), and *E. coli* 80 strain, which has been imparted with resistance to sulfaguanidine, DL-1,2,4-triazole-3-alanine, and streptomycin (VKPM B-7270, Russian Patent No. 2119536).

<L-Cysteine-Producing Bacteria>

Examples of methods for imparting or enhancing L-cysteine-producing ability include, for example, a method of modifying a bacterium so that the bacterium has an increased activity or activities of one or more of the L-cysteine biosynthesis enzymes. Examples of such enzymes include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and U.S. Patent Published Application No. 20050112731. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting or enhancing L-cysteine-producing ability also include, for example, a method of modifying a bacterium so that the bacterium has a reduced activity or activities of one or more enzymes that catalyze a reaction branching away from the biosynthesis pathway of L-cysteine to generate a compound other than L-cysteine. Examples of such enzymes include, for example, enzymes involved in decomposition of L-cysteine. Examples of the enzymes involved in decomposition of L-cysteine include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), O-acetylserine sulfhydrylase B (cysM, Japanese Patent Laid-open (Kokai) No. 2005-245311), the malY gene product (Japanese Patent Laid-open (Kokai) No. 2005-245311), and the d0191 gene product of *Pantoea ananatis* (Japanese Patent Laid-open (Kokai) No. 2009-232844).

Furthermore, examples of methods for imparting or enhancing L-cysteine-producing ability also include, for example, a method of enhancing the L-cysteine excretory system, and a method of enhancing the sulfate/thiosulfate transport system. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysPTWAM gene cluster.

Specific examples of L-cysteine-producing bacteria and parental strains that can be used to derive such bacteria include, for example, *E. coli* JM15 transformed with different cysE alleles encoding feedback-resistant serine acetyltransferases (U.S. Pat. No. 6,218,168, Russian patent application 2003121601), *E. coli* W3110 that overexpresses a gene encoding a protein suitable for secretion of a cytotoxic substance (U.S. Pat. No. 5,972,663), *E. coli* strains having a reduced cysteine desulfohydrase activity (JP11155571A2), and *E. coli* W3110 having an increased activity of a positive transcriptional regulator for cysteine regulon encoded by the cysB gene (WO0127307A1).

<L-Methionine-Producing Bacteria>

Examples of L-methionine-producing bacteria and parental strains that can be used to derive such bacteria include L-threonine auxotrophic strains and mutant strains resistant to norleucine (Japanese Patent Laid-open (Kokai) No. 2000-139471). Examples of L-methionine-producing bacteria and parental strains that can be used to derive such bacteria also include a strain containing a mutant homoserine transsuccinylase resistant to feedback inhibition by L-methionine (Japanese Patent Laid-open (Kokai) No. 2000-139471, U.S. Patent Published Application No. 20090029424). Since L-methionine is biosynthesized via L-cysteine as an intermediate, L-methionine-producing ability can also be improved by increasing L-cysteine production (Japanese Patent Laid-open (Kokai) No. 2000-139471, U.S. Patent Published Application No. 20080311632).

Specific examples of L-methionine-producing bacteria and parental strains that can be used to derive such bacteria include, for example, *E. coli* AJ11539 (NRRL B-12399), *E. coli* AJ11540 (NRRL B-12400), *E. coli* AJ11541 (NRRL B-12401), *E. coli* AJ11542 (NRRL B-12402, British Patent No. 2075055), the *E. coli* 218 strain (VKPM B-8125, Russian Patent No. 2209248) and the 73 strain (VKPM B-8126, Russian Patent No. 2215782), which are resistant to norleucine, which is an analogue of L-methionine, and *E. coli* AJ13425 (FERMP-16808, Japanese Patent Laid-open (Kokai) No. 2000-139471). The AJ13425 strain is an L-threonine auxotrophic strain derived from the *E. coli* W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability include, for example, a method of modifying a bacterium so that the bacterium has an increased activity or activities of one or more of the L-leucine biosynthesis enzymes. Examples of such enzymes include, but are not particularly limited to, the enzymes encoded by the genes of the leuABCD operon. Furthermore, for enhancing the activity of such an enzyme, for example, the mutant leuA gene encoding an isopropyl maleate synthase desensitized to feedback inhibition by L-leucine (U.S. Pat. No. 6,403,342) can be used.

Specific examples of L-leucine-producing bacteria and parental strains that can be used to derive such bacteria include, for example, strains belonging to the genus *Escherichia*, such as *E. coli* strains resistant to leucine (for example, the 57 strain (VKPM B-7386, U.S. Pat. No. 6,124,121)), *E. coli* strains resistant to a leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), *E. coli* strains obtained by a gene engineering technique described in WO96/06926, and *E. coli* H-9068 (Japanese Patent Laid-open (Kokai) No. 8-70879).

<L-Isoleucine-Producing Bacteria>

Examples of methods for imparting or enhancing L-isoleucine-producing ability include, for example, a method of modifying a bacterium so that the bacterium has increased activity or activities of one or more of the L-isoleucine biosynthesis enzymes. Examples of such enzymes include, but are not particularly limited to, threonine deaminase and acetohydroxy acid synthase (Japanese Patent Laid-open (Kokai) No. 2-458, FR 0356739, U.S. Pat. No. 5,998,178).

Specific examples of L-isoleucine-producing bacteria and parental strains that can be used to derive such bacteria include, for example, *Escherichia* bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

<L-Valine-Producing Bacteria>

Examples of methods for imparting or enhancing L-valine-producing ability include, for example, a method of modifying a bacterium so that the bacterium has an increased activity or activities of one or more of the L-valine biosynthesis enzymes. Examples of such enzymes include, but are not particularly limited to, the enzymes encoded by the genes of the ilvGMEDA operon and the enzymes encoded by the ilvBNC operon. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, to enhance the activity of such an enzyme, the suppression of expression by the produced L-valine can be released by removing or modifying a region required for the attenuation. Furthermore, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, for L-valine production, the ilvA gene can be, for example, disrupted, and thereby the threonine deaminase activity is decreased.

Examples of methods for imparting or enhancing L-valine-producing ability also include, for example, a method of modifying a bacterium so that the bacterium has a reduced activity or activities of one or more enzymes that catalyze a reaction branching away from the biosynthesis pathway of L-valine to generate a compound other than L-valine. Examples of such enzymes include, but are not particularly limited to, threonine dehydratase involved in the L-leucine synthesis, and the enzymes involved in the D-pantothenic acid synthesis (WO00/50624).

Specific examples of L-valine-producing bacteria and parental strains that can be used to derive such bacteria include, for example, *E. coli* strains modified so as to overexpress the ilvGMEDA operon (U.S. Pat. No. 5,998,178).

Examples of L-valine-producing bacteria and parental strains that can be used to derive such bacteria also include mutant strains having a mutation in amino-acyl t-RNA synthetase (U.S. Pat. No. 5,658,766). Examples of such strains include, for example, *E. coli* VL1970, which has a mutation in the ileS gene encoding isoleucine t-RNA synthetase. *E. coli* VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains that can be used to derive such bacteria also include mutant strains requiring lipoic acid for growth and/or lacking $H^+$-ATPase (WO96/06926).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability include, for example, a method of modifying a bacterium so that the bacterium has an increased activity or activities of one or more of the L-tryptophan, L-phenylalanine, and/or L-tyrosine biosynthesis enzymes.

Examples of enzymes having common biosynthesis systems of these aromatic amino acids include, but not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (European Patent No. 763127). The expressions of the genes encoding these enzymes are controlled by the tyrosine repressor (tyrR), and the activities of these enzymes may be enhanced by deleting the tyrR gene (European Patent No. 763127).

Examples of the L-tryptophan biosynthesis enzymes include, but are not particularly limited to, anthranilate synthase (trpE), tryptophan synthase (trpAB), and phosphoglycerate dehydrogenase (serA). For example, by introducing a DNA containing the tryptophan operon, L-tryptophanproducing ability can be imparted or enhanced. Tryptophan synthase consists of α and β subunits encoded by the trpA and trpB genes, respectively. Since the anthranilate synthase is subject to feedback inhibition by L-tryptophan, a gene encoding this enzyme introduced with a mutation for desensitization to feedback inhibition may be used for enhancing the activity of that enzyme. Since the phosphoglycerate dehydrogenase is subject to feedback inhibition by L-serine, a gene encoding this enzyme introduced with a mutation for desensitization to feedback inhibition may be used for enhancing the activity of that enzyme. Furthermore, by increasing the expression of the operon (ace operon) consisting of the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes encoding these enzymes introduced with a mutation for desensitization to feedback inhibition may be used to enhance the activities of these enzymes.

Examples of the L-tyrosine biosynthesis enzymes include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes encoding these enzymes introduced with a mutation for desensitization to feedback inhibition may be used to enhance the activities of these enzymes.

The L-tryptophan, L-phenylalanine, and/or L-tyrosine-producing bacteria may be modified so that biosynthesis of an aromatic amino acid other than the objective aromatic amino acid is reduced. Furthermore, the L-tryptophan, L-phenylalanine, and/or L-tyrosine-producing bacteria may be modified so that a by-product uptake system is enhanced. Examples of the by-product include aromatic amino acids other than the objective aromatic amino acid. Examples of the gene encoding such a by-product uptake system include, for example, tnaB and mtr, which are genes encoding the L-tryptophan uptake system, pheP, which is a gene encoding the L-phenylalanine uptake system, and tyrP, which is a gene encoding the L-tyrosine uptake system (EP 1484410).

Specific examples of L-tryptophan-producing bacteria and parental strains that can be used to derive such bacteria include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient tryptophanase (U.S. Pat. No. 4,371,614), E. coli AGX17/pGX50, pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (U.S. Patent Published Applications 2003/0148473 A1 and 2003/0157667 A1).

Specific examples of L-phenylalanine-producing bacteria and parental strains that can be used to derive such bacteria include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutant pheA34 gene encoding a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of L-phenylalanine-producing bacteria and parental strains that can be used to derive such bacteria also include, for example, E. coli K-12<W3110 (tyrA)/pPHAB> (FERM BP-3566), E. coli K-12<W3110 (tyrA)/pPHAD> (FERM BP-12659), E. coli K-12<W3110 (tyrA)/pPHATerm> (FERM BP-12662), and E. coli K-12 AJ12604<W3110(tyrA)/pBR-aroG4, pACMAB> (FERM BP-3579), which contains a gene encoding a chorismate mutase-prephenate dehydratase desensitized to feedback inhibition (EP 488424 B1). Specific examples of L-phenylalanine-producing bacteria and parental strains that can be used to derive such bacteria further include, for example, strains belonging to the genus Escherichia having an increased activity of the protein encoded by the yedA gene or the yddG gene (U.S. Patent Published Applications Nos. 2003/0148473 and 2003/0157667, WO03/044192).

Furthermore, examples of methods for imparting or enhancing an L-amino acid-producing ability include, for example, a method of modifying a bacterium so that the bacterium has an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids include, for example, b2682 (ygaZ), b2683 (ygaH), b1242 (ychE), and b3434 (yhgN) (Japanese Patent Laid-open (Kokai) No. 2002-300874).

Furthermore, examples of methods for imparting or enhancing an L-amino acid-producing ability also include, for example, a method of modifying a bacterium so that the bacterium has an increased activity or activities of one or more of the proteins involved in the glycometabolism and energy metabolism.

Examples of the proteins involved in the glycometabolism include proteins involved in uptake of saccharides and the glycolysis system enzymes. Examples of genes encoding a protein involved in glycometabolism include genes encoding glucose-6-phosphate isomerase (pgi, WO01/02542), pyruvate carboxylase (pyc, WO99/18228, European Patent Laid-open No. 1092776), phosphoglucomutase (pgm, WO03/04598), fructose bisphosphate aldolase (pfkB, fbp, WO03/04664), transaldolase (talB, WO03/008611), fumarase (fum, WO01/02545), non-PTS sucrose uptake (csc, European Patent Laid-open No. 149911), and sucrose assimilation (scrAB operon, WO90/04636).

Examples of genes encoding the proteins involved in the energy metabolism include the transhydrogenase gene (pntAB, U.S. Pat. No. 5,830,716) and cytochrome bo-type oxidase gene (cyoB, European Patent Laid-open No. 1070376).

The genes used for the breeding of the aforementioned L-amino acid-producing bacteria are not limited to the genes exemplified above and genes having a known nucleotide sequence, and may include variants of these genes, so long as the original function of the gene is maintained. For example, the genes used for the breeding of the L-amino acid-producing bacteria may be encode a protein having an amino acid sequence of a known protein, but include substitution, deletion, insertion, or addition of one or several amino acid residues at one or several positions. For the variants of genes and proteins, the descriptions concerning variants of aconitase and acetaldehyde dehydrogenase, and genes encoding them mentioned later can be similarly applied.

<1-2> Enhancement of Aconitase Activity and Acetaldehyde Dehydrogenase Activity

The bacterium has been modified so that the activity of aconitase is increased, or both the activities of aconitase and acetaldehyde dehydrogenase are increased. By modifying a bacterium so that the activity of aconitase is increased, or both the activities of aconitase and acetaldehyde dehydrogenase are increased, L-amino acid production by the bacterium using ethanol as a carbon source can be improved.

The bacterium can be obtained by modifying a bacterium having an L-amino acid-producing ability so that the activity of aconitase is increased, or both the activities of aconitase and acetaldehyde dehydrogenase are increased. Furthermore, the bacterium can also be obtained by modifying a bacterium so that the activity of aconitase is increased, or the activities of aconitase and acetaldehyde dehydrogenase are increased, and then imparting an L-amino acid producing ability to the bacterium or enhancing L-amino acid-producing ability of the bacterium. The bacterium may also acquire an L-amino acid-producing ability by being modified so that the activity of aconitase is increased, or both the activities of aconitase and acetaldehyde dehydrogenase are increased. The modifications for constructing the bacterium can be performed in an arbitrary order.

The term "aconitase" refers to a protein having an activity for reversibly catalyzing the isomerization between citrate and isocitrate (EC 4.2.1.3). This activity is also referred to as "aconitase activity". A gene that encodes aconitase is also referred to as "aconitase gene". The aconitase activity can be measured by, for example, measuring generation of cis-aconitate from isocitrate (Gruer M J, Guest J R., Microbiology., 1994, October; 140 (10):2531-41).

Examples of aconitase include the AcnB protein, which is encoded by the acnB gene, and the AcnA protein, which is encoded by the acnA gene. For example, the activity of the AcnA protein may be enhanced, the activity of the AcnB protein may be enhanced, or the activities of both the AcnA protein and AcnB protein may be enhanced. When the bacterium has not been modified so that the activity of acetaldehyde dehydrogenase is increased, at least the activity of the AcnB protein is enhanced.

Examples of the AcnA protein and AcnB protein include, for example, AcnA proteins and AcnB proteins of bacteria belonging to the family Enterobacteriaceae such as *Escherichia coli*, *Pantoea ananatis*, *Pectobacterium atrosepticum* (formerly, Envinia carotovora), and *Salmonella enterica*.

The acnA gene of the *Escherichia coli* K-12 MG1655 strain corresponds to the sequence of the positions 1335831 to 1338506 in the genome sequence registered at the NCBI database as GenBank accession NC_000913 (VERSION NC_000913.3 GI: 556503834). The AcnA protein of the MG1655 strain is registered as GenBank accession NP_415792 (version NP_415792.1 GI: 16129237). The nucleotide sequence of the acnA gene and the amino acid sequence of the AcnA protein of the MG1655 strain are shown as SEQ ID NOS: 21 and 22, respectively.

The acnA gene of the *Pantoea ananatis* AJ13355 strain corresponds to the complementary sequence of the sequence of the positions 1665681 to 1668362 in the genome sequence registered at the NCBI database as GenBank accession NC_017531 (VERSION NC_017531.1 GI: 386014600). The AcnA protein of the AJ13355 strain is registered as GenBank accession YP_005934253 (version YP_005934253.1 GI: 386015968). The nucleotide sequence of the acnA gene and the amino acid sequence of the AcnA protein of the AJ13355 strain are shown as SEQ ID NOS: 23 and 24, respectively.

The acnA gene of the *Pectobacterium atrosepticum* SCRI1043 strain corresponds to the sequence of the positions 2198282 to 2200954 in the genome sequence registered at the NCBI database as GenBank accession NC_004547 (VERSION NC_004547.2 GI: 50119055). The AcnA protein of the SCRI1043 strain is registered as GenBank accession YP_050038 (version YP_050038.1 GI: 50120871). The nucleotide sequence of the acnA gene and the amino acid sequence of the AcnA protein of the SCRI1043 strain are shown as SEQ ID NOS: 25 and 26, respectively.

The acnA gene of the *Salmonella enterica* serovar Typhi CT18 strain corresponds to the sequence of the positions 1298278 to 1300953 in the genome sequence registered at the NCBI database as GenBank accession NC_003198 (VERSION NC_003198.1 GI: 16762629). The AcnA protein of the CT18 strain is registered as GenBank accession NP_455785 (version NP_455785.1 GI: 16760168). The nucleotide sequence of the acnA gene and the amino acid sequence of the AcnA protein of the CT18 strain are shown as SEQ ID NOS: 27 and 28, respectively.

The acnB gene of the *Escherichia coli* K-12 MG1655 strain corresponds to the sequence of the positions 131615 to 134212 in the genome sequence registered at the NCBI database as GenBank accession NC_000913 (VERSION NC_000913.3 GI: 556503834). The AcnB protein of the MG1655 strain is registered as GenBank accession NP_414660 (version NP_414660.1 GI: 16128111). The nucleotide sequence of the acnB gene and the amino acid sequence of the AcnB protein of the MG1655 strain are shown as SEQ ID NOS: 29 and 30, respectively.

The acnB gene of the *Pantoea ananatis* AJ13355 strain corresponds to the sequence of the positions 116856 to 119552 in the genome sequence registered at the NCBI database as GenBank accession NC 017531 (VERSION NC 017531.1 GI: 386014600). The AcnB protein of the AJ13355 strain is registered as GenBank accession YP_005932972 (version YP_005932972.1 GI: 386014695). The nucleotide sequence of the acnB gene and the amino acid sequence of the AcnB protein of the AJ13355 strain are shown as SEQ ID NOS: 31 and 32, respectively.

The acnB gene of the *Pectobacterium atrosepticum* SCRI1043 strain corresponds to the complementary sequence of the sequence of the positions 4218908 to 4221505 in the genome sequence registered at the NCBI database as GenBank accession NC 004547 (VERSION NC_004547.2 GI: 50119055). The AcnB protein of the SCRI1043 strain is registered as GenBank accession YP_051867 (version YP_051867.1 GI: 50122700). The nucleotide sequence of the acnB gene and the amino acid sequence of the AcnB protein of the SCRI1043 strain are shown as SEQ ID NOS: 33 and 34, respectively.

The acnB gene of the *Salmonella enterica* serovar *Typhi* CT18 strain corresponds to the sequence of the positions 189006 to 191603 in the genome sequence registered at the NCBI database as GenBank accession NC_003198 (VERSION NC_003198.1 GI: 16762629). The AcnB protein of the CT18 strain is registered as GenBank accession NP_454772 (version NP_454772.1 GI: 16759155). The nucleotide sequence of the acnB gene and the amino acid sequence of the AcnB protein of the CT18 strain are shown as SEQ ID NOS: 35 and 36, respectively.

The term "acetaldehyde dehydrogenase" refers to a protein that reversibly catalyzes the reaction of generating acetic acid from acetaldehyde by using $NAD^+$ or $NADP^+$ as an electron acceptor (EC 1.2.1.3, EC 1.2.1.4, EC 1.2.1.5, EC 1.2.1.22, etc.). This activity is also referred to as "acetaldehyde dehydrogenase activity". A gene encoding acetaldehyde dehydrogenase is also referred to as "acetaldehyde dehydrogenase gene". The acetaldehyde dehydrogenase activity can be measured by, for example, measuring acetaldehyde-dependent reduction of $NAD^+$ or $NADP^+$ (Ho K K, Weiner H., J. Bacteriol., 2005, February; 187(3): 1067-73).

Acetaldehyde dehydrogenase is also referred to as "CoA-independent acetaldehyde dehydrogenase", and is distinguished from CoA-dependent acetaldehyde dehydrogenase (to be explained later). Acetaldehyde dehydrogenase is also referred to as "aldehyde dehydrogenase", "lactaldehyde dehydrogenase", or the like.

Examples of the acetaldehyde dehydrogenase include A1 dB protein, which is encoded by aldB gene. Examples of the A1 dB protein include, for example, A1 dB proteins of bacteria belonging to the family Enterobacteriaceae such as *Escherichia coli*, *Pantoea ananatis*, *Pectobacterium atrosepticum* (formerly, Envinia *carotovora*), and *Salmonella enterica*.

The aldB gene of the *Escherichia coli* K-12 MG1655 strain corresponds to the complementary sequence of the sequence of the positions 3754973 to 3756511 in the genome sequence registered at the NCBI database as GenBank accession NC_000913 (VERSION NC_000913.3 GI: 556503834). The A1 dB protein of the MG1655 strain is registered as GenBank accession NP_418045 (version NP_418045.4 GI: 90111619). The nucleotide sequence of the aldB gene and the amino acid sequence of the A1 dB protein of the MG1655 strain are shown as SEQ ID NOS: 37 and 38, respectively.

An aldB gene homologue of the *Pantoea ananatis* LMG 20103 strain is registered as one of aldA genes at a database. This aldB gene homologue is regarded as the aldB gene. The aldB gene of the *Pantoea ananatis* LMG 20103 strain corresponds to the complementary sequence of the sequence of the positions 2168098 to 2169570 in the genome sequence registered at the NCBI database as GenBank accession NC_013956 (VERSION NC_013956.2 GI: 332139403). The AldB protein of the LMG 20103 strain is registered as GenBank accession YP_003520235 (version YP_003520235.1 GI: 291617493). The nucleotide sequence of the aldB gene and the amino acid sequence of the A1 dB protein of the LMG 20103 strain are shown as SEQ ID NOS: 39 and 40, respectively.

The aldB gene of the *Pectobacterium atrosepticum* SCRI1043 strain corresponds to the sequence of the positions 111626 to 113161 in the genome sequence registered at the NCBI database as GenBank accession NC_004547 (VERSION NC_004547.2 GI: 50119055). The A1 dB protein of the SCRI1043 strain is registered as GenBank accession YP_048222 (version YP_048222.1 GI: 50119055). The nucleotide sequence of the aldB gene and the amino acid sequence of the A1 dB protein of the SCRI1043 strain are shown as SEQ ID NOS: 41 and 42, respectively.

The aldB gene of the *Salmonella enterica* serovar *Typhi* CT18 strain corresponds to the sequence of the positions 3978586 to 3980124 in the genome sequence registered at the NCBI database as GenBank accession NC_003198 (VERSION NC_003198.1 GI: 16762629). The A1 dB protein of the CT18 strain is registered as GenBank accession NP_458246 (version NP_458246.1 GI: 16762629). The nucleotide sequence of the aldB gene and the amino acid sequence of the A1 dB protein of the CT18 strain are shown as SEQ ID NOS: 43 and 44, respectively.

The result of alignment of these AldB proteins is shown in FIG. 1A-1B. The homologies of the amino acid sequence of the AldB protein of the *Escherichia coli* K-12 MG1655 strain to the amino acid sequences of the AldB proteins of the *Pantoea ananatis* LMG 20103 strain, *Pectobacterium atrosepticum* SCRI1043 strain, and *Salmonella enterica* serovar *Typhi* CT18 strain are 64.7%, 81.4%, and 95.8%, respectively.

That is, the aconitase gene may be, for example, a gene having the nucleotide sequence shown as SEQ ID NO: 21, 23, 25, 27, 29, 31, 33, or 35. Also, aconitase may be, for example, a protein having the amino acid sequence shown as SEQ ID NO: 22, 24, 26, 28, 30, 32, 34, or 36. Also, the acetaldehyde dehydrogenase gene may be, for example, a gene having the nucleotide sequence shown as SEQ ID NO: 37, 39, 41, or 43. Also, acetaldehyde dehydrogenase may be, for example, a protein having the amino acid sequence shown as SEQ ID NO: 38, 40, 42, or 44. The expression "a gene or protein has a nucleotide or amino acid sequence" encompasses cases where a gene or protein comprises the nucleotide or amino acid sequence, and cases where a gene or protein consists of the nucleotide or amino acid sequence.

Aconitase may be a variant of any of the aconitases exemplified above (e.g. AcnA proteins and AcnB proteins exemplified above), so long as the original function thereof is maintained. Similarly, the aconitase gene may be a variant of any of the aconitase genes exemplified above (e.g. acnA genes and acnB genes exemplified above), so long as the original function thereof is maintained. Also, acetaldehyde dehydrogenase may be a variant of any of the acetaldehyde dehydrogenases exemplified above (e.g. AldB proteins exemplified above), so long as the original function thereof is maintained. Similarly, the acetaldehyde dehydrogenase gene may be a variant of any of the acetaldehyde dehydrogenase genes exemplified above (e.g. aldB genes exemplified above), so long as the original function is maintained. Such a variant that maintains the original function is also referred to as a "conservative variant". Examples of the conservative variants include, for example, homologues and artificially modified versions of the aconitases and acetaldehyde dehydrogenases exemplified above and genes encoding them.

The terms "AcnA protein", "AcnB protein", and "AldB protein", include not only the AcnA proteins, AcnB proteins, and AldB proteins exemplified above, respectively, but also includes respective conservative variants thereof. Similarly, the terms "acnA gene", "acnB gene", and "aldB gene" include not only the acnA genes, acnB genes, and aldB genes exemplified above, but also includes respective conservative variants thereof.

The expression "the original function is maintained" means that a variant of gene or protein has a function (such as activity or property) corresponding to the function (such as activity or property) of the original gene or protein. That is, the expression "the original function is maintained" used for aconitase means that a variant of the protein has the aconitase activity, and the expression "the original function is maintained" used for acetaldehyde dehydrogenase means that a variant of the protein has the acetaldehyde dehydrogenase activity. Also, the expression "the original function is maintained" used for the aconitase gene means that a variant of the gene encodes a protein of which the original function is maintained, i.e. a protein having the aconitase activity, and the expression "the original function is maintained" used for the acetaldehyde dehydrogenase gene means that a variant of the gene encodes a protein of which the original function is maintained, i.e. a protein having the acetaldehyde dehydrogenase activity.

Hereafter, examples of the conservative variants will be explained.

Examples of homologues of aconitase and acetaldehyde dehydrogenase include, for example, proteins that can be obtained from public databases by BLAST search or FASTA search using any of the aforementioned amino acid sequences as a query sequence. Furthermore, homologues of the aconitase and acetaldehyde dehydrogenase genes can be obtained by, for example, PCR using a chromosome of various microorganisms as the template, and oligonucleotides prepared on the basis of any of the aforementioned nucleotide sequences as primers.

Aconitase or acetaldehyde dehydrogenase may be a protein having any of the aforementioned amino acid sequences, that is, the amino acid sequence shown as SEQ ID NO: 24, 26, 28, 30, 32, 34, or 36 for aconitase, or the amino acid sequence shown as SEQ ID NO: 38, 40, 42, or 44 for acetaldehyde dehydrogenase, but which includes substitution, deletion, insertion, or addition of one or several amino acid residues at one or several positions, so long as the original function is maintained. Although the number meant by the term "one or several" mentioned above may differ depending on the positions of amino acid residues in the three-dimensional structure of the protein or the types of amino acid residues, specifically, it is, for example, 1 to 50, 1 to 40, or 1 to 30, 1 to 20, 1 to 10, 1 to 5, or 1 to 3.

The aforementioned substitution, deletion, insertion, or addition of one or several amino acid residues is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, inversion, or the like of amino acid residues as mentioned above includes a naturally occurring mutation due to an individual difference, or a difference of species of the organism from which the protein is derived (mutant or variant).

Aconitase or acetaldehyde dehydrogenase may be a protein having an amino acid sequence showing a homology of, for example, 80% or more, 90% or more, 95% or more, 97% or more, 99% or more, to the total amino acid sequence of any of the aforementioned amino acid sequences, so long as the original function is maintained. In this description, "homology" can mean "identity".

Aconitase or acetaldehyde dehydrogenase may be a protein encoded by a DNA that is able to hybridize under stringent conditions with a probe that can be prepared from any of the aforementioned nucleotide sequences, that is, the nucleotide sequence shown as SEQ ID NO: 21, 23, 25, 27, 29, 31, 33, or 35 for aconitase, or the nucleotide sequence shown as SEQ ID NO: 37, 39, 41, or 43 for acetaldehyde dehydrogenase, such as a sequence complementary to a partial or entire sequence of any of the aforementioned nucleotide sequences, so long as the original function is maintained. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, that is, conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization may be, for example, 50° C., 2×SSC and 0.1% SDS.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, for example, alignment, for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

Furthermore, since the degeneracy of codons differs depending on the host, arbitrary codons in the aconitase or acetaldehyde dehydrogenase gene may be replaced with respective equivalent codons. For example, the aconitase or acetaldehyde dehydrogenase gene may be a gene modified so that it has optimal codons according to codon frequencies in the chosen host.

The aforementioned descriptions concerning conservative variants of the genes and proteins can be similarly applied to variants of arbitrary proteins such as L-amino acid biosynthesis system enzymes and ethanol metabolic enzymes and genes encoding them.

<1-3> Ethanol-Utilizing Ability

The bacterium has an ethanol-utilizing ability. The expression that "a bacterium has an ethanol-utilizing ability" means that the bacterium can grow in a minimal medium containing ethanol as the sole carbon source. The bacterium may inherently have an ethanol-utilizing ability, or it may have been modified so that it has an ethanol-utilizing ability. A bacterium having an ethanol-utilizing ability can be obtained by, for example, imparting an ethanol-utilizing ability to any of such bacteria as mentioned above, or enhancing an ethanol-utilizing ability of the same.

An ethanol-utilizing ability can be imparted or enhanced by modifying a bacterium so that the activity or activities of one or more of the ethanol metabolic enzymes are increased. That is, the bacterium may have been modified so that the activity or activities of one or more ethanol metabolic enzymes are increased.

Examples of the ethanol metabolic enzymes include alcohol dehydrogenase and CoA-dependent acetaldehyde dehydrogenase.

The term "alcohol dehydrogenase" refers to a protein having an activity for reversibly catalyzing the reaction of generating acetaldehyde from ethanol by using NAD$^+$ or NADP$^+$ as an electron acceptor (EC 1.1.1.1, EC 1.1.1.2, EC 1.1.1.71, etc.). This activity is also referred to as "alcohol dehydrogenase activity". The alcohol dehydrogenase activity can be measured by, for example, measuring ethanol-dependent reduction of NAD$^+$ (Clark D, Cronan J E Jr., J. Bacteriol., 1980, January; 141(1):177-83).

The term "CoA-dependent acetaldehyde dehydrogenase" refers to a protein having an activity for reversibly catalyzing the reaction of generating acetyl-CoA from acetaldehyde by using NAD$^+$ or NADP$^+$ as an electron acceptor (EC 1.2.1.10). This activity is also referred to as "CoA-dependent acetaldehyde dehydrogenase activity". The CoA-dependent acetaldehyde dehydrogenase activity can be measured by, for example, measuring acetaldehyde- and CoA-dependent reduction of NAD$^+$ (Rudolph F B, Purich D L, Fromm H J., J. Biol. Chem., 1968, Nov. 10; 243 (21):5539-45).

Examples of the ethanol metabolic enzymes include AdhE protein, which is encoded by adhE gene. The AdhE protein is a bi-functional enzyme, and has both the alcohol dehydrogenase activity and CoA-dependent acetaldehyde dehydrogenase activity. Examples of the AdhE protein include, for example, AdhE proteins of bacteria belonging to the family Enterobacteriaceae such as *Escherichia coli, Pantoea ananatis, Pectobacterium atrosepticum* (formerly, Envinia carotovora), and *Salmonella enterica*.

The adhE gene of the *Escherichia coli* K-12 MG1655 strain corresponds to the complementary sequence of the sequence of the positions 1295446 to 1298121 in the genome sequence registered at the NCBI database as GenBank accession NC_000913 (VERSION NC_000913.3 GI: 556503834). The AdhE protein of the MG1655 strain is registered as GenBank accession NP_415757 (version NP_415757.1 GI: 16129202). The nucleotide sequence of the adhE gene and the amino acid sequence of the AdhE protein of the MG1655 strain are shown as SEQ ID NOS: 45 and 46, respectively.

The adhE gene of the *Pantoea ananatis* LMG 20103 strain corresponds to the sequence of the positions 2335387 to 2338071 in the genome sequence registered at the NCBI database as GenBank accession NC_013956 (VERSION NC_013956.2 GI: 332139403). The AdhE protein of the LMG 20103 strain is registered as GenBank accession YP_003520384 (version YP_003520384.1 GI: 291617642). The nucleotide sequence of the adhE gene and the amino acid sequence of the AdhE protein of the LMG 20103 strain are shown as SEQ ID NOS: 47 and 48, respectively.

The adhE gene of the *Pectobacterium atrosepticum* SCRI1043 strain corresponds to the sequence of the positions 2634501 to 2637176 in the genome sequence registered at the NCBI database as GenBank accession NC_004547 (VERSION NC_004547.2 GI: 50119055). The AdhE protein of the SCRI1043 strain is registered as GenBank accession YP_050421 (version YP_050421.1 GI: 50121254). The nucleotide sequence of the adhE gene and the amino acid sequence of the AdhE protein of the SCRI1043 strain are shown as SEQ ID NOS: 49 and 50, respectively.

An adhE gene homologue of the *Salmonella enterica* serovar *Typhi* CT18 strain is registered as adh gene at a database. This adhE gene homologue is regarded as the adhE gene. The adhE gene of the *Salmonella enterica* serovar *Typhi* CT18 strain corresponds to the complementary sequence of the sequence of the positions 1259893 to 1262571 in the genome sequence registered at the NCBI database as GenBank accession NC_003198 (VERSION NC_003198.1 GI: 16762629). The AdhE protein of the CT18 strain is registered as GenBank accession NP_455751 (version NP_455751.1 GI: 16760134). The nucleotide sequence of the adhE gene and the amino acid sequence of AdhE protein of the CT18 strain are shown as SEQ ID NOS: 51 and 52, respectively.

The result of alignment of these AdhE proteins is shown in FIG. 2A-2C. The homologies of the amino acid sequence of the AdhE protein of the *Escherichia coli* K-12 MG1655 strain to the amino acid sequences of the AdhE proteins of the AdhE proteins of the *Pantoea ananatis* LMG 20103 strain, *Pectobacterium atrosepticum* SCRI1043 strain, and *Salmonella enterica* serovar *Typhi* CT18 strain are 89.0%, 89.1%, and 97.2%, respectively.

The ethanol metabolic enzyme may be a conservative variant of any of the ethanol metabolic enzymes exemplified above such as the AdhE proteins of bacteria belonging to the family Enterobacteriaceae exemplified above. For example, the AdhE protein may be a protein having the amino acid sequence shown as SEQ ID NO: 46, 48, 50, or 52, but including substitution, deletion, insertion, or addition of one or several amino acid residues at one or several positions. For the variants of genes and proteins, the descriptions concerning conservative variants of aconitase and acetaldehyde dehydrogenase, and genes encoding them mentioned above can be similarly applied.

The bacterium has an ethanol-utilizing ability under aerobic conditions, that is, it can aerobically utilize ethanol. The expression that "a bacterium has an ethanol-utilizing ability under aerobic conditions" means that the bacterium can grow in a minimal medium containing ethanol as a sole carbon source under aerobic conditions. The expression that "a bacterium has an ethanol-utilizing ability under aerobic conditions" may mean that, for example, the specific activity of alcohol dehydrogenase in a cell-free extract prepared from cells of the bacterium obtained by aerobic culture is, for example, 1.5 U/mg protein or higher, 5 U/mg protein or higher, or 10 U/mg protein or higher. One unit of the alcohol dehydrogenase activity is defined as generation of 1 nmol of NADH in 1 minute under the aforementioned activity measurement conditions (Clark D, Cronan J E Jr., J. Bacteriol., 1980, January; 141(1):177-83). The term "aerobic conditions" refers to culture conditions that oxygen is supplied to the culture system by, for example, aeration, shaking, and/or stirring. The bacterium may inherently have an ethanol-utilizing ability under aerobic conditions, or it may have been modified so that it has an ethanol-utilizing ability under aerobic conditions. For example, although *Escherichia coli* typically cannot aerobically utilize ethanol, *Escherichia coli* may be modified so that it can aerobically utilize ethanol.

An ethanol-utilizing ability under aerobic conditions can be imparted or enhanced by modifying a bacterium so that the activity or activities of one or more kinds of enzymes selected from ethanol metabolic enzymes are increased under aerobic conditions. That is, the bacterium may have been modified so that the activity or activities of one or more ethanol metabolic enzymes are increased under aerobic conditions.

An ethanol-utilizing ability under aerobic conditions can be imparted or enhanced by, for example, modifying a bacterium so that the bacterium has an adhE gene that is expressed under the control of a promoter that functions under aerobic conditions.

Such modification can be attained by, for example, replacing the native promoter of an adhE gene on a bacterial genome with a promoter that functions under aerobic conditions. Alternatively, an adhE gene ligated downstream from a promoter that functions under aerobic conditions may be introduced into a bacterium, or an adhE gene may be introduced downstream from a promoter that is present on the bacterial genome and functions under the aerobic conditions. As for replacement of a promoter or introduction of a gene, the descriptions of "Methods for increasing activity of protein" mentioned later can be referred to.

The promoter that functions under aerobic conditions is not particularly limited, so long as it is able to express the adhE gene under the aerobic conditions to such an extent that the bacterium can utilize ethanol. Examples of the promoter that functions under aerobic conditions include, for example, promoters of genes of the glycolysis system, pentose phosphate pathway, TCA cycle, and amino acid biosynthesis systems, and the $P_{14}$ promoter (SEQ ID NO: 1) used in the Examples section. Examples of the promoter that functions under aerobic conditions also include, for example, such strong promoters as T7 promoter, trp promoter, lac promoter, thr promoter, tac promoter, trc promoter, tet promoter, araBAD promoter, rpoH promoter, PR promoter, and PL promoter.

An ethanol-utilizing ability under aerobic conditions can be imparted or enhanced by, for example, modifying a bacterium so as to harbor an adhE gene encoding an AdhE protein having a mutation for improving resistance to inactivation under aerobic conditions. The "mutation for improving resistance to inactivation under aerobic conditions" is also referred to as "aerobic resistance mutation".

An AdhE protein having an aerobic resistance mutation is also referred to as "mutant AdhE protein". A gene encoding a mutant AdhE protein is also referred to as "mutant adhE gene."

An AdhE protein not having any aerobic resistance mutation is also referred to as "wild-type AdhE protein". A gene encoding a wild-type AdhE protein is also referred to as "wild-type adhE gene". The term "wild-type" is used to distinguish from a "mutant" gene or protein, and a "wild-type" gene or protein is not limited to one obtained from the nature so long as it does not have any aerobic resistance mutation. Examples of the wild-type AdhE protein include, for example, AdhE proteins of the bacteria belonging to the family Enterobacteriaceae exemplified above. Any of conservative variants of AdhE proteins of the bacteria belonging to the family Enterobacteriaceae exemplified above is regarded as a wild-type AdhE protein, so long as it does not have any aerobic resistance mutation.

Examples of the aerobic resistance mutation include a mutation wherein an amino acid residue corresponding to the glutamic acid residue at position 568 in the amino acid sequence of the wild-type AdhE protein, such as SEQ ID NO: 46 of the AdhE protein of *Escherichia coli* K-12 MG1655 strain, is replaced with an amino acid residue other than glutamic acid and aspartic acid (WO2008/010565). Examples of the amino acid residue at that position after the replacement include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), N (Asn), and Q (Gln). The amino acid residue at that position after the replacement may be, for example, lysine. When the amino acid residue at that position after the replacement is lysine residue, the mutation is also referred to as "Glu568Lys" or "E568K" mutation.

The mutant AdhE protein may further have an additional mutation selected from the following mutations:

(A) a mutation that in the amino acid sequence of a wild-type AdhE protein, such as the amino acid sequence of SEQ ID NO: 46, an amino acid residue corresponding to the glutamic acid residue at position 560 is replaced with another amino acid residue, (B) a mutation that in the amino acid sequence of a wild-type AdhE protein, such as the amino acid sequence of SEQ ID NO: 46, an amino acid residue corresponding to the phenylalanine residue at position 566 is replaced with another amino acid residue, (C) a mutation that in the amino acid sequence of a wild-type AdhE protein, such as the amino acid sequence of SEQ ID NO: 46, amino acid residues corresponding to the glutamic acid residue at position 22, methionine residue at position 236, tyrosine residue at position 461, isoleucine residue at position 554, and alanine residue at position 786 are replaced with respective other amino acid residues;

(D) a combination of these mutations.

As for the aforementioned additional mutations, examples of the amino acid residue after the replacement include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), provided that the amino acid residue after the replacement must differ from the amino acid residue before the replacement. In the case of the aforementioned mutation (A), the amino acid residue existing after the replacement may be, for example, lysine residue. In the case of the aforementioned mutation (B), the amino acid residue existing after the replacement may be, for example, valine residue. In the case of the aforementioned mutation (C), the amino acid residues existing after the replacement may be, for example, glycine residue for position 22 (Glu22Gly), valine residue for position 236 (Met236Val), cysteine residue for position 461 (Tyr461Cys), serine residue for position 554 (Ile554Ser), and valine residue for position 786 (Ala786Val).

In the amino acid sequence of an arbitrary wild-type AdhE protein, the term "amino acid residue corresponding to the amino acid residue at position n in the amino acid sequence of SEQ ID NO: 46" refers to an amino acid residue corresponding to the amino acid residue at position n in the amino acid sequence of SEQ ID NO: 46 determined in alignment of the amino acid sequence of the objective wild-type AdhE protein and the amino acid sequence of SEQ ID NO: 46. That is, the positions of amino acid residues defined in the aforementioned mutations do not necessarily represent the absolute positions in the amino acid sequence of a wild-type AdhE protein, but represent the relative positions determined on the basis of the amino acid sequence of SEQ ID NO: 46. For example, when one amino acid residue of the wild-type AdhE protein consisting of the amino acid sequence of SEQ ID NO: 46 is deleted at a position on the N-terminus side of position n, the amino acid residue originally at position n becomes the (n−1)th amino acid residue counted from the N-terminus, but it is still regarded as the "amino acid residue corresponding to the amino acid residue at position n in the amino acid sequence of SEQ ID NO: 46". Similarly, for example, when an amino acid residue at position 567 in the amino acid sequence of an AdhE protein homologue of a certain microorganism corresponds to the amino acid residue at position 568 in the amino acid sequence of SEQ ID NO: 46, that amino acid residue is regarded as the "amino acid residue corresponding to the amino acid residue at position 568 in the amino acid sequence shown as SEQ ID NO: 46" in the AdhE protein homologue.

Such alignment can be performed by, for example, using known gene analysis software. Specific examples of such gene analysis software include DNASIS produced by Hitachi Solutions, GENETYX produced by Genetyx, ClustalW opened to the public by DDBJ, and so forth (Elizabeth C. Tyler et al., Computers and Biomedical Research, 24(1), 72-96, 1991; Barton G J. et al., Journal of Molecular Biology, 198(2), 327-37, 1987; Thompson J D et al., Nucleic Acid Research, 22(22), 4673-80, 1994).

A mutant adhE gene can be obtained by, for example, modifying a wild-type adhE gene so that the AdhE protein encoded by the wild-type adhE gene has an aerobic resistance mutation. The wild-type adhE gene to be modified can be obtained by, for example, cloning from an organism having the wild-type adhE gene, or chemical synthesis. A mutant adhE gene may also be directly obtained by, for example, chemical synthesis, or the like.

Modification of a gene can be performed by a known method. For example, by the site-specific mutagenesis method, an objective mutation can be introduced into a target site of DNA. Examples of the site-specific mutagenesis method include a method of using PCR (Higuchi, R., 61, in PCR Technology, Erlich, H. A. Eds., Stockton Press (1989); Carter P., Meth. in Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

A mutant adhE gene is introduced into the bacterium in such a manner that the gene can be expressed. Specifically, the gene can be introduced into the bacterium so that it is expressed under the control of a promoter that functions under aerobic conditions. As for introduction of a gene, the descriptions of "Methods for increasing activity of protein" mentioned later can be referred to.

<1-4> Other Modifications

The bacterium may also have been modified so that the activity of pyruvate synthase (also referred to as "PS") and/or pyruvate:NADP$^+$ oxidoreductase (also referred to as "PNO") is increased (WO2009/031565).

The term "pyruvate synthase" refers to an enzyme reversibly catalyzing the reaction of generating pyruvic acid from acetyl-CoA and $CO_2$ using the reduced ferredoxin or reduced flavodoxin as an electron donor (EC 1.2.7.1). PS is also referred to as pyruvate oxidoreductase, pyruvate ferredoxin oxidoreductase, or pyruvate flavodoxin oxidoreductase. The activity of PS can be measured according to, for example, the method of Yoon et al. (Yoon, K. S. et al., 1997, Arch. Microbiol., 167:275-279).

Examples of a gene encoding PS (PS gene) include PS genes of bacteria having the reductive TCA cycle such as *Chlorobium tepidum* and *Hydrogenobacter thermophilus*, PS genes of bacteria belonging to the family Enterobacteriaceae such as *Escherichia coli*, and PS genes of autotrophic methanogens such as *Methanococcus maripaludis*, *Methanocaldococcus jannaschii*, and *Methanothermobacter thermautotrophicus*.

The term "pyruvate:NADP$^+$ oxidoreductase" refers to an enzyme reversibly catalyzing the reaction of generating pyruvic acid from acetyl CoA and $CO_2$ using NADPH or NADH as an electron donor (EC 1.2.1.15). The pyruvate:NADP$^+$ oxidoreductase is also referred to as pyruvate dehydrogenase. The activity of PNO can be measured by, for example, the method of Inui et al. (Inui, H., et al., 1987, J. Biol. Chem., 262:9130-9135).

Examples of a gene encoding PNO (PNO gene) include the PNO gene of *Euglena gracilis*, which is a photosynthetic eukaryotic microorganism and is also classified into protozoans (Nakazawa, M. et al., 2000, FEBS Lett., 479:155-156), the PNO gene of a protist, *Cryptosporidium parvum* (Rotte, C. et al., 2001, Mol. Biol. Evol., 18:710-720, GenBank Accession No. AB021127), and a PNO homologous gene of Bacillariophyta, *Tharassiosira pseudonana* (Ctrnacta, V. et al., 2006, J. Eukaryot. Microbiol., 53:225-231).

Enhancement of the PS activity can also be attained by, besides the methods of increasing the activities of proteins such as described later, improving supply of the electron donor required for the PS activity. For example, the PS activity can be enhanced by enhancing the activity of recycling ferredoxin or flavodoxin of the oxidized form to that of the reduced form, enhancing the ability to biosynthesize ferredoxin or flavodoxin, or combination of them (WO2009/031565).

Examples of a protein having the activity of recycling ferredoxin or flavodoxin of the oxidized form to that of the reduced form include ferredoxin $NADP^+$ reductase. The term "ferredoxin $NADP^+$ reductase" refers to an enzyme that reversibly catalyzes the reaction of converting ferredoxin or flavodoxin of the oxidized form to that of the reduced form using NADPH as the electron donor (EC 1.18.1.2). Ferredoxin $NADP^+$ reductase is also referred to as flavodoxin $NADP^+$ reductase. The activity of ferredoxin NADP+ reductase can be measured by, for example, the method of Blaschkowski et al. (Blaschkowski, H. P. et al., 1982, Eur. J. Biochem., 123:563-569).

Examples of a gene encoding ferredoxin $NADP^+$ reductase (ferredoxin $NADP^+$ reductase gene) include the fpr gene of *Escherichia coli*, the ferredoxin NADP+ reductase gene of *Corynebacterium glutamicum*, and the NADPH-putidaredoxin reductase gene of *Pseudomonas putida* (Koga, H. et al., 1989, J. Biochem. (Tokyo) 106:831-836).

The ability to biosynthesize ferredoxin or flavodoxin can be enhanced by enhancing the expression of a gene encoding ferredoxin (ferredoxin gene) or a gene encoding flavodoxin (flavodoxin gene). The ferredoxin gene or flavodoxin gene is not particularly limited, so long as it encodes ferredoxin or flavodoxin that can be utilized by PS and the electron donor recycling system.

Examples of the ferredoxin gene include the fdx gene and yfhL gene of *Escherichia coli*, the fer gene of *Corynebacterium glutamicum*, and ferredoxin genes of bacteria having the reductive TCA cycle such as *Chlorobium tepidum* and *Hydrogenobacter thermophilus*. Examples of the flavodoxin gene include the fldA gene and fldB gene of *Escherichia coli*, and flavodoxin genes of bacteria having the reductive TCA cycle.

The bacterium may also have been modified so that the activity of ribonuclease G is reduced (JP2012-100537A).

The bacterium may also have been modified so as to harbor a mutant ribosome S1 protein (JP2013-074795A).

The bacterium may also have been modified so that the intracellular concentration of hydrogen peroxide is reduced (JP2014-036576A).

The aforementioned genes such as the PS gene, PNO gene, ferredoxin NADP+ reductase gene, ferredoxin gene, and flavodoxin gene are not limited to genes having the aforementioned genetic information and genes having a known nucleotide sequence, and may be a variant thereof, so long as the functions of the encoded proteins are not degraded. For example, the genes may be a gene encoding a protein having an amino acid sequence of a known protein, but including substitution, deletion, insertion, or addition of one or several amino acid residues at one or several positions. For the variants of genes and proteins, the descriptions concerning conservative variants of aconitase and acetaldehyde dehydrogenase, and genes encoding them mentioned above can be similarly applied.

<1-5> Methods for Increasing Activity of Protein

Hereafter, the methods for increasing the activity of a protein such as aconitase and acetaldehyde dehydrogenase will be explained.

The expression "the activity of a protein is increased" means that the activity of the protein per cell is increased as compared with that of a non-modified strain such as a wild-type strain or parental strain. The state that "the activity of a protein is increased" may also be expressed as "the activity of a protein is enhanced". Specifically, the expression "the activity of a protein is increased" means that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Furthermore, the state that "the activity of a protein is increased" includes not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased, for example, 1.5 times or more, 2 times or more, or 3 times or more, as compared with that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" means that the expression amount of the gene per cell is increased as compared with that of a non-modified strain such as a wild-type strain or parental strain. Specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased, for example, 1.5 times or more, 2 times or more, or 3 times or more, as compared with that of a non-modified strain. Furthermore, the phrase that "the expression of a gene is increased" includes not only when the expression amount of an objective gene is increased in a strain that inherently expresses the objective gene, but also when the gene is introduced into a strain that does not inherently express the objective gene, and is then expressed. That is, the phrase "the expression of a gene is increased" may also mean, for example, that an objective gene is introduced into a strain that does not possess the gene, and is then expressed.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pACYC series vectors, and the broad host spectrum vector RSF1010.

When a gene is introduced, it is sufficient that the gene is expressibly harbored by the bacterium. Specifically, it is sufficient that the gene is introduced so that it is expressed under control by a promoter sequence that functions in the chosen bacterium. The promoter may be a promoter derived from the host, or a heterogenous promoter. The promoter may be the native promoter of the gene to be introduced, or a promoter of another gene. Examples of the promoter include promoters of genes of the glycolysis system, pentose phosphate pathway, TCA cycle, and amino acid biosynthesis systems, and the $P_{14}$ promoter (SEQ ID NO: 1) used in the Examples section. As the promoter, for example, such a stronger promoter as mentioned later may also be used.

A terminator for termination of gene transcription may be located downstream of the gene. The terminator is not particularly limited so long as it functions in the bacterium of the present invention. The terminator may be a terminator derived from the host, or a heterogenous terminator. The terminator may be the native terminator of the gene to be introduced, or a terminator of another gene. Specific examples of the terminator include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the bacterium. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The case of "introducing two or more genes" include, for example, cases of introducing respective genes encoding two or more kinds of enzymes, introducing respective genes encoding two or more subunits constituting a single enzyme, and a combination of the foregoing cases.

The gene to be introduced is not particularly limited so long as it encodes a protein that functions in the host. The gene to be introduced may be a gene derived from the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required.

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that encode the subunits may be enhanced. It is usually preferable to enhance the expression of all of the plurality of genes encoding the subunits. Furthermore, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" means a promoter providing an improved transcription of a gene compared with an inherently existing wild-type promoter of the gene. Examples of stronger promoters include, for example, the known high expression promoters such as T7 promoter, trp promoter, lac promoter, thr promoter, tac promoter, trc promoter, tet promoter, araBAD promoter, rpoH promoter, PR promoter, and PL promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. In *Escherichia coli* etc., a clear codon bias exists among the 61 amino acid codons found within the population of mRNA molecules, and the level of cognate tRNA appears directly proportional to the frequency of codon usage (Kane, J. F., Curr. Opin. Biotechnol., 6 (5), 494-500 (1995)). That is, if there is a large amount of mRNA containing an excess amount of rare codons, a translational problem may arise. According to the recent research, it is suggested that clusters of AGG/AGA, CUA, AUA, CGA, or CCC codons may especially reduce both the quantity and quality of a synthesized protein. Such a problem occurs especially at the time of expression of a heterologous gene. Therefore, in the case of heterogenous expression of a gene or the like, the translation efficiency of the gene can be improved by replacing a rare codon present in the gene with a synonymous codon more frequently used. That is, the gene to be introduced may be modified, for example, so as to contain optimal codons according to the frequencies of codons observed in a host to be used. Codons can be replaced by, for example, the site-specific mutation method for introducing an objective mutation into an objective site of DNA. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity also includes desensitization to feedback inhibition. That is, when a protein is subject to feedback inhibition by a metabolite, the activity of the protein can be increased by making the bacterium harbor a gene encoding a mutant protein that has been desensitized to the feedback inhibition. The phrase "desensitization to feedback inhibition" includes attenuation and elimination of the feedback inhibition. A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parental strain. Examples of the method for evaluating the amount of mRNA include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins, besides enhancement of the aconitase and acetaldehyde dehydrogenase activities.

<1-4> Method for Reducing Activity of Protein

Hereafter, the methods for reducing the activity of a protein will be explained.

The expression "the activity of a protein is reduced" means that the activity of the protein per cell is reduced as compared with that of a non-modified strain such as a wild-type strain and parental strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0%, as compared with that of a non-modified strain.

The modification for reducing the activity of a protein can be attained by, for example, reducing the expression of a gene encoding the protein. The expression "the expression of a gene is reduced" means that the expression of the gene per cell is reduced as compared with that of a non-modified strain such as a wild-type strain and parental strain. The expression "the expression of a gene is reduced" may specifically mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0%, as compared with that of a non-modified strain.

The reduction in gene expression may be due to, for example, a reduction in the transcription efficiency, a reduction in the translation efficiency, or a combination of these. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, three or more nucleotides, of the expression control sequence are modified. Furthermore, a part of or the entire expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting a part of or the entire coding region of the gene on a chromosome. Furthermore, the entire gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, reading frames of the sequences upstream and downstream from the region to be deleted may not be the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. Reading frames of the sequences upstream and downstream from the insertion site may not be the same. The other sequence is not particularly limited so long as the chosen sequence reduces or eliminates the activity of the encoded protein, and examples thereof include, for example, a marker gene such as antibiotic resistance genes, and a gene useful for production of an objective sub stance.

Such modification of a gene on a chromosome as described above can be attained by, for example, preparing a deficient type gene modified so that it is unable to produce a protein that normally functions, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. Examples of the deficient type gene include a gene including deletion of all or a part of the gene, gene including a missense mutation, gene including insertion of a transposon or marker gene, gene including a nonsense mutation, and gene including a frame shift mutation. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ, phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, as compared with that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0%, as compared with that of a non-modified strain.

Disruption of a gene can be confirmed by determining nucleotide sequence of a part or the whole of the gene, restriction enzyme map, full length, or the like of the gene depending on the means used for the disruption.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<2> Method for Producing L-Amino Acid of the Present Invention

The method of the present invention is a method for producing an L-amino acid by culturing the bacterium in a medium containing ethanol to generate and accumulate the L-amino acid in the medium or cells of the bacterium, and collecting the L-amino acid from the medium or the cells. One kind of L-amino acid may be produced, or two or more kinds of L-amino acids may be produced.

The medium is not particularly limited, so long as it contains ethanol, the bacterium can proliferate in it, and an L-amino acid can be produced. As the medium, for example, a usual medium used for culture of bacteria and so forth can be used. The medium may contain, in addition to ethanol, carbon source, nitrogen source, phosphate source, and sulfur source, as well as components selected from other various organic components and inorganic components as required.

Types and concentrations of the medium components may be appropriately determined according to various conditions such as type of the chosen bacterium and type of the L-amino acid to be produced.

In the method, ethanol may be or may not be used as a sole carbon source. That is, in the method, in addition to ethanol, another carbon source may be used together. The other carbon source is not particularly limited, so long as the bacterium can utilize, and an L-amino acid can be produced. Specific examples of the other carbon source include, for example, saccharides such as glucose, fructose, sucrose, lactose, galactose, arabinose, blackstrap molasses, hydrolysate of starch, and hydrolysate of biomass, organic acids such as acetic acid, fumaric acid, citric acid, succinic acid, and malic acid, alcohols such as glycerol and crude glycerol, and aliphatic acids. When another carbon source is used, the ratio of ethanol in the total carbon source may be, for example, 5% by weight or more, 10% by weight or more, or 20% by weight or more, 30% by weight or more, 50% by weight or more. As the other carbon source, one kind of carbon source may be used, or two or more kinds of carbon sources may be used in combination.

The concentration of the carbon source in the medium is not particularly limited, so long the bacterium can proliferate in the medium, and an L-amino acid can be produced. The concentration of the carbon source in the medium can be as high as possible in such a range that the production of the L-amino acid is not inhibited. The initial concentration of the carbon source in the medium may be, for example, usually 1 to 30% (W/V), or 3 to 10% (W/V). Along with the consumption of the carbon source that occurs as fermentation advances, the carbon source may be continued to be added.

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires an amino acid or the like for growth thereof is used, a required nutrient can be supplemented to the medium. For example, in many of L-lysine-producing bacteria, the L-lysine biosynthetic pathway is enhanced and the L-lysine degrading ability is attenuated. Therefore, when such an L-lysine-producing bacterium is cultured, for example, one or more amino acids such as L-threonine, L-homoserine, L-isoleucine, and L-methionine can be added to the medium.

Culture conditions are not particularly limited, so long as the bacterium can proliferate, and an L-amino acid can be produced. The culture can be performed with, for example, usual conditions used for bacteria such as *Escherichia coli*. The culture conditions may be appropriately determined depending on various conditions such as the type of chosen bacterium and type of L-amino acid to be produced.

The culture can be performed by using a liquid medium. At the time of the culture, the bacterium cultured on a solid medium such as agar medium may be directly inoculated into a liquid medium, or the bacterium cultured in a liquid medium as seed culture may be inoculated into a liquid medium for main culture. That is, the culture may be performed as separate seed culture and main culture. In such a case, the culture conditions of the seed culture and the main culture may be or may not be the same. Amount of the bacterium present in the medium at the time of the start of the culture is not particularly limited. For example, a seed culture broth showing an OD660 of 4 to 8 may be added to a medium for main culture at a ratio of 0.1 to 30 mass %, or 1 to 10 mass %, at the time of the start of the culture.

The culture can be performed as batch culture, fed-batch culture, continuous culture, or a combination of these. The medium used at the time of the start of the culture is also referred to as "starting medium". The medium supplied to a culture system (fermentation tank) in fed-batch culture or continuous culture is also referred to as "feed medium". Furthermore, to supply a medium to a culture system in fed-batch culture or continuous culture is also referred to as to "feed". Furthermore, when the culture is performed as separate seed culture and main culture, for example, both the seed culture and the main culture may be performed as batch culture. Alternatively, for example, the seed culture may be performed as batch culture, and the main culture may be performed as fed-batch culture or continuous culture.

The medium components each may be contained in the starting medium, feed medium, or the both. The types of the components contained in the starting medium may be or may not be the same as the types of the components contained in the feed medium. The concentration of each component contained in the starting medium may be or may not be the same as the concentration of the component contained in the feed medium. Furthermore, two or more kinds of feed media containing different types and/or different concentrations of components may be used. For example, when medium is intermittently fed a plurality of times, the types and/or concentrations of components contained in the feed media may be or may not be the same.

The concentration of ethanol in the medium is not particularly limited, so long as the bacterium can use ethanol as the carbon source. Ethanol may be contained in the medium at a concentration of, for example, 10 w/v % or lower, 5 w/v % or lower, or 2 w/v % or lower. Also, ethanol may be contained in the medium at a concentration of, for example, 0.2 w/v % or higher, 0.5 w/v % or higher, or 1.0 w/v % or higher. Ethanol may be contained in the starting medium, feed medium, or the both at a concentration within the range exemplified above.

When ethanol is contained in the feed medium, ethanol may be contained in the feed medium at such a concentration that, for example, the ethanol concentration in the medium after feeding is 5 w/v % or lower, 2 w/v % or lower, or 1 w/v % or lower. When ethanol is contained in the feed medium, ethanol may be contained in the feed medium at such a concentration that, for example, the ethanol concentration in the medium after feeding is 0.01 w/v % or higher, 0.02 w/v % or higher, or 0.05 w/v % or higher.

When ethanol is used as the sole carbon source, the ethanol concentration may be within the range exemplified above. When ethanol is used in combination with another carbon source, the ethanol concentration may also be within the range exemplified above. When ethanol is used in combination with another carbon source, the ethanol concentration may also be within a range defined by appropriately modifying the range exemplified above on the basis of, for example, ratio of ethanol in the total carbon source, or the like.

The ethanol concentration may be or may not be within a certain range over the whole period of culture. For example, ethanol may run short during a partial period of culture. The term "run short" means that the amount of ethanol is smaller than the required amount, and it may mean that, for example, the concentration in the medium becomes zero. The term "partial period of culture" may refer to, for example, 1% or less, 5% or less, 10% or less, 20% or less, 30% or less, or 50% or less of the whole period of the culture. When the culture is performed as separate seed culture and main culture, the term "whole period of the culture" may mean the whole period of the main culture. It is preferred that, during a period when ethanol runs short, another carbon source is present in a sufficient amount. Even if ethanol runs short during a partial period of culture as described above, culture performed under such a condition falls within the scope of the expression "culture of a bacterium in a medium containing ethanol", so long as there is a culture period where the culture is performed in a medium containing ethanol.

Concentration of various components such as ethanol can be measured by gas chromatography (Hashimoto, K. et al., Biosci. Biotechnol. Biochem., 1996, 70:22-30) or HPLC (Lin, J. T. et al., J. Chromatogr. A., 1998, 808:43-49).

The culture can be, for example, aerobically performed. For example, the culture can be performed as aeration culture or shaking culture. The oxygen concentration can be controlled to be, for example, 5 to 50%, or about 10%, of the saturated oxygen concentration. pH of the medium may be, for example, 3 to 10, or 4.0 to 9.5. During the culture, pH of the medium can be adjusted as required. pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture period may be, for example, 10 to 120 hours. The culture may be continued, for example, until the carbon source contained in the medium is consumed, or until the bacterium loses the activity. By culturing the bacterium under such conditions as described above, an L-amino acid is accumulated in cells of the bacterium and/or the medium.

In the fed-batch culture or continuous culture, feeding of the feed medium may be continued over the whole period of the culture or only during a partial period of the culture. In the fed-batch culture or continuous culture, feeding may be intermittently performed a plurality of times.

When feeding is intermittently performed a plurality of times, the feeding may be repeatedly started and stopped so that the period for one time of feeding is, for example, 30% or shorter, 20% or shorter, or 10% or shorter, of the total period of the feeding of the plurality of times.

Furthermore, when feeding is intermittently performed a plurality of times, the carbon source concentration in the fermentation medium can also be automatically maintained at a low level by controlling the feeding so that the second and following feedings are started when the carbon source in the fermentation medium is depleted in the non-feeding periods immediately before the respective feedings (U.S. Pat. No. 5,912,113). Depletion of the carbon source can be detected on the basis of, for example, elevation of pH, or elevation of dissolved oxygen concentration.

In the continuous culture, extraction of the culture medium may be continued over the whole period of the culture or only during a partial period of the culture. Furthermore, in the continuous culture, extraction of the culture medium may be intermittently performed a plurality of times. Extraction and feeding of the culture medium may be or may not be simultaneously performed. For example, after extracting the culture medium, feeding may be performed, or after performing feeding, the culture medium may be extracted. It is preferred that the volume of the culture medium to be extracted is equal to the volume of the medium to be fed. The expression "the volume of the culture medium to be extracted is equal to the volume of the medium to be fed equal volume" may mean that the volume of the culture medium to be extracted is, for example, 93 to 107% of the volume of the medium to be fed.

When the culture medium is continuously extracted, the extraction can be started at the same time as or after the start of the feeding. For example, within 5 hours, 3 hours, or 1 hour, after the start of the feeding, the extraction can be started.

When the culture medium is intermittently extracted, it is preferred that, when the concentration of the L-amino acid reaches a predetermined level, a part of the culture medium is extracted to collect the L-amino acid, and then a fresh medium is fed to continue the culture.

Furthermore, after the L-amino acid is collected from the extracted culture medium, the cells can be reused by recycling filtration residue containing the cells into the fermentation tank (French Patent No. 2669935).

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated include, for example, pH 5.0 to 3.0, pH 4.9 to 3.5, pH 4.9 to 4.0, or around pH 4.7 (EP 1078989 A). The culture may be performed at a pH value within the aforementioned ranges over the whole period of culture, or only during a partial period of culture. The term "partial period of culture" may refer to, for example, 50% or more, 70% or more, 80% or more, 90% or more, 95% or more, or 99% or more, of the whole period of culture.

When a basic amino acid such as L-lysine is produced, there may be employed a method in which the basic amino acid is produced by fermentation using bicarbonate ions and/or carbonate ions as major counter ions for the basic amino acid (Japanese Patent Laid-open (Kokai) No. 2002-65287, U.S. Patent Published Application No. 20020025564, EP 1813677 A). By such a method, a basic amino acid can be produced while reducing the amounts of sulfate ions and/or chloride ions to be used, which have been conventionally used as counter ions for a basic amino acid.

In such a method, pH of the medium is controlled to be 6.5 to 9.0, 6.5 to 8.0, during the culture, and 7.2 to 9.0 at the end of the culture, so that there is a culture period where 20 mM or more, 30 mM or more, 40 mM or more, of bicarbonate ions and/or carbonate ions are present in the medium. In order to ensure bicarbonate and/or carbonate ions exist in the medium in an amount required as counter ions of the basic amino acid, the internal pressure of the fermentation tank can be controlled to be positive during the fermentation, carbon dioxide gas can be supplied into the culture medium, or both.

The internal pressure of the fermentation tank during fermentation can be controlled to be positive by, for example, making the gas supply pressure higher than the exhaust pressure. If the internal pressure of the fermentation tank is made positive, the carbon dioxide gas generated by fermentation dissolves in the culture medium to generate bicarbonate ions and/or carbonate ions, and these can serve as counter ions of the basic amino acid. The internal pressure of the fermentation tank can be, specifically, 0.03 to 0.2 MPa, 0.05 to 0.15 MPa, 0.1 to 0.3 MPa, in terms of the gage pressure (pressure difference with respect to the atmospheric pressure). When carbon dioxide gas is supplied to the medium, for example, pure carbon dioxide gas or a mixed gas containing 5 volume % or more of carbon dioxide gas can be bubbled in the medium. The internal pressure in the fermentation tank, supply volume of carbon dioxide gas, and limited aeration volume can be determined by, for example, measuring pH of the medium, bicarbonate and/or carbonate ion concentration in the medium, or ammonia concentration in the medium.

In the conventional methods for producing a basic amino acid, a sufficient amount of ammonium sulfate and/or ammonium chloride is usually added to the medium in order to use sulfate ions and/or chloride ions as counter ions of the basic amino acid, or sulfuric acid decomposition products and/or hydrochloric acid decomposition products of proteins etc. are added to the medium as nutrient components. Therefore, large amounts of sulfate ions and/or chloride ions are present in the medium, and the concentration of the weakly acidic carbonate ions is extremely low, i.e., it is at a ppm order.

On the other hand, the aforementioned method (Japanese Patent Laid-open (KOKAI) No. 2002-65287, U.S. Patent Published Application No. 20020025564A, EP 1813677 A) is characterized in that the amounts of these sulfate ions and chloride ions to be used are reduced so that the carbon dioxide gas released by microorganism during fermentation is dissolved in the medium, and used as counter ions.

That is, to reduce the amounts of sulfate ions and/or chloride ions to be used is one of the objects of the aforementioned method, and therefore the total molar concentration of sulfate ions or chloride ions contained in the medium is usually 700 mM or lower, 500 mM or lower, 300 mM or lower, 200 mM or lower, or 100 mM or lower. By lowering the concentrations of sulfate ions and/or chloride ions, it is easier to ensure the presence of bicarbonate and/or carbonate ions in the medium. That is, in the aforementioned method, the pH of the medium to ensure the presence of bicarbonate and/or carbonate ions in the medium in an amount required as counter ions of the basic amino acid can be suppressed to be lower compared with the conventional methods.

Furthermore, in the aforementioned method, lower concentrations of anions other than bicarbonate ions and/or carbonate ions (also referred to as other anions) in the medium are preferred so long as they are present in amounts required for the growth of the basic amino acid-producing bacterium. Examples of the other anions include chloride ions, sulfate ions, phosphate ions, ionized organic acids, and hydroxide ions. The total molar concentration of these other anions is usually 900 mM or lower, 700 mM or lower, 500 mM or lower, 300 mM or lower, 200 mM or lower.

In the aforementioned method, it is not necessary to add sulfate ions or chloride ions to the medium in an amount larger than that required for growth of the basic amino acid-producing bacterium. It is preferred that appropriate amounts of ammonium sulfate etc. are fed to the medium at an early stage of the culture, and the feeding is terminated in the middle of the culture. Alternatively, ammonium sulfate etc. may be fed to the medium with maintaining the balance with respect to the amounts of carbonate ions and/or bicarbonate ions dissolved in the medium. Furthermore, ammonia may be fed to the medium as a nitrogen source of the basic amino acid. For example, when pH is controlled with ammonia, ammonia supplied in order to elevate pH may be used as a nitrogen source of the basic amino acid. Ammonia can be supplied to the medium independently or together with another gas.

In the aforementioned method, it is also preferable to control the total ammonia concentration in the medium to such a concentration that production of the basic amino acid is not inhibited. Examples of such a total ammonia concentration that "production of the basic amino acid is not inhibited" include, for example, a total ammonia concentration providing yield and/or productivity corresponding to 50% or more, 70% or more, 90% or more, of the yield and/or productivity obtainable in the production of the basic amino acid under optimal conditions. Specifically, for example, the total ammonia concentration in the medium may be 300 mM or lower, 250 mM or lower, or 200 mM or lower. The dissociation degree of ammonia decreases as the pH becomes higher. Non-dissociating ammonia is more toxic to bacteria compared with ammonium ions. Therefore, the upper limit of the total ammonia concentration also depends on the pH of the culture medium. That is, as the pH of the culture medium increases, the acceptable total ammonia concentration decreases. Therefore, the total ammonia concentration at which "production of the basic amino acid is not inhibited" is preferably determined for each specific pH value. However, the total ammonia concentration range that is acceptable at the highest pH level during the culture can be used as the total ammonia concentration range throughout the entire culture period.

On the other hand, the total concentration of ammonia as a source of nitrogen required for growth of the basic amino acid-producing bacterium and production of the basic amino acid is not particularly limited, and can be appropriately determined, so long as depletion of ammonia does not continue during the culture, and decrease in the productivity of the objective substance by the microorganism due to the shortage of the nitrogen source does not occur. For example, the ammonia concentration can be measured over time during the culture, and if ammonia in the medium is depleted, a small amount of ammonia can be added to the medium. Although the ammonia concentration after the addition of ammonia is not particularly limited, the total ammonia concentration can be, for example, 1 mM or higher, 10 mM or higher, 20 mM or higher.

Furthermore, in the aforementioned method, the medium may contain cations other than the basic amino acid. Examples of cations other than the basic amino acid include K, Na, Mg, and Ca originating in medium components. The total molar concentration of the cations other than those of the basic amino acid can be 50% or lower of the molar concentration of the total cations.

Production of the L-amino acid can be confirmed by known methods used for detection or identification of compounds. Examples of such methods include, for example, HPLC, LC/MS, GC/MS, and NMR. These methods can be used in an appropriate combination.

The produced L-amino acid can be collected by known methods used for separation and purification of compounds. Examples of such methods include, for example, ion-exchange resin method, membrane treatment, precipitation, and crystallization. These methods can be used in an appropriate combination. When the L-amino acid is accumulated in bacterial cells, the bacterial cells can be disrupted with, for example, ultrasonic waves or the like, and then the L-amino acid can be collected by the ion-exchange resin method or the like from the supernatant obtained by removing the cells from the cell-disrupted suspension by centrifugation. The L-amino acid to be collected may be a free compound, a salt thereof, or a mixture thereof. Examples of the salt include, for example, sulfate, hydrochloride, carbonate, ammonium salt, sodium salt, and potassium salt. For example, L-lysine may be free L-lysine, L-lysine sulfate, L-lysine hydrochloride, L-lysine carbonate, or a mixture of these. Also, for example, L-glutamic acid may be free L-glutamic acid, sodium L-glutamate (monosodium L-glutamate, MSG), ammonium L-glutamate (monoammonium L-glutamate), or a mixture of these. For example, in the case of L-glutamic acid, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5).

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The purity of the collected L-amino acid may be, for example, 30% (w/w) or higher, 50% (w/w) or higher, 70% (w/w) or higher, 80% (w/w) or higher, 90% (w/w) or higher, or 95% (w/w) or higher.

EXAMPLES

The present invention will be more specifically explained with reference to the following examples.

Example 1: Impartation of Ethanol-Utilizing Ability to L-Lysine-Producing Bacterium, AJIK01 Strain (NITE BP-01520)

By using an L-lysine-producing bacterium, *Escherichia coli* AJIK01 strain (NITE BP-01520), as a parental strain, an L-lysine-producing bacterium imparted with an ethanol-utilizing ability, AJIK01m2 strain, was constructed.

First, P1 lysate was obtained from the *Escherichia coli* MG1655-att-tet-$P_{L\text{-}tac}$adhE* strain (WO2011/096554) in a conventional manner, and P1 transduction was performed by using the AJIK01 strain (NITE BP-01520) as the host to obtain the AJIK01 att-tet-$P_{L\text{-}tac}$adhE* strain, into which a cassette containing the adhE* gene was introduced. The adhE* gene is a mutant adhE gene encoding a mutant AdhE protein corresponding to the wild-type AdhE protein of the *Escherichia coli* K-12 MG1655 strain shown as SEQ ID NO: 46 introduced with six mutations of Glu568Lys, Glu22Gly, Met236Val, Tyr461Cys, Ile554Ser, and Ala786Val (WO2008/010565).

Then, in order to remove the att-tet sequence introduced upstream of the $P_{L\text{-}tac}$ promoter, a helper plasmid pMW-intxis-ts (refer to U.S. Published Patent Application No. 2006/0141586) was used. The plasmid pMW-intxis-ts is a plasmid carrying a gene encoding the integrase (Int) of λ phage and a gene encoding excisionase (Xis) of λ, phage, and having temperature-sensitive replication ability. Competent cells of the AJIK01 att-tet-$P_{L\text{-}tac}$adhE* strain obtained above were produced in a conventional manner, transformed with the helper plasmid pMW-intxis-ts, and cultured at 30° C. on the LB agar medium containing 100 mg/L of ampicillin, and ampicillin resistant strains were selected. In order to remove the pMW-intxis-ts plasmid, transformants were cultured at 42° C. on the LB agar medium. Ampicillin resistance and tetracycline resistance of the obtained colonies were examined to obtain a strain sensitive to ampicillin and tetracycline. The obtained strain is a $P_{L\text{-}tac}$adhE*-introduced strain in which the att-tet sequence was removed from the genome of chromosome, and pMW-intxis-ts was eliminated. This strain was designated as AJIK01m2 strain.

Example 2: Construction of L-Lysine-Producing Bacterium Having Enhanced Expression of acnB Gene (1) Construction of Expression Plasmid pMW119-attR-Cat-attL-$P_{14}$ Containing Promoter $P_{14}$ PCR was performed by using the synthetic oligonucleotides shown as SEQ ID NOS: 2 and 3 as the primers, and the chromosomal DNA of the *Escherichia coli* MG1655 strain as the template to amplify the sequence of the gdhA gene containing the promoter $P_{14}$, which is shown as SEQ ID NO: 1. The PCR product was purified, treated by using Takara BKL Kit (Takara Bio), and ligated with pMW219 (NIPPON GENE) digested with SmaI and treated by using Takara BKL Kit to obtain a plasmid pMW219-$P_{14}$-gdhA.

PCR was performed by using the synthetic oligonucleotides shown as SEQ ID NOS: 4 and 5 as the primers, and pMW219-$P_{14}$-gdhA as the template to amplify the sequence of the promoter $P_{14}$ moiety ($P_{14}$ sequence).

PCR was performed by using the synthetic oligonucleotides shown as SEQ ID NOS: 6 and 7 as the primers, and a plasmid pMW118-attL-Cm-attR (WO2005/010175) as the template to amplify the attR-cat-attL sequence having the chloramphenicol resistance gene cat between the sequences attR and attL of the attachment site of λ phage.

The attR-cat-attL sequence and $P_{14}$ sequence were ligated to pMW119 (NIPPON GENE) digested with HindIII and SalI by using In-Fusion HD Cloning Kit (Takara Bio) to construct an expression plasmid containing the promoter $P_{14}$, pMW119-attR-cat-attL-$P_{14}$.

(2) Construction of Plasmid pMW119-attR-Cat-attL-$P_{14}$-acnB for Enhancing Expression of acnB Gene PCR was performed by using the synthetic oligonucleotides shown as SEQ ID NOS: 8 and 9 as the primers, and the chromosomal DNA of the *Escherichia coli* MG1655 strain as the template to amplify a sequence containing the acnB gene. PCR was performed by using the synthetic oligonucleotides shown as SEQ ID NOS: 10 and 11 as the primers, and the plasmid pMW119-attR-cat-attL-$P_{14}$ as the template to amplify linear pMW119-attR-cat-attL-$P_{14}$. The sequence containing the acnB gene and linear pMW119-attR-cat-attL-$P_{14}$ were ligated by using In-Fusion HD Cloning Kit (Takara Bio) to construct a plasmid pMW119-attR-cat-attL-$P_{14}$-acnB, which expresses the acnB gene under the control of the promoter $P_{14}$.

The constructed plasmid pMW119-attR-cat-attL-$P_{14}$-acnB was introduced into the AJIK01m2 strain in a conventional manner to obtain a strain AJIK01m2/pMW119-attR-cat-attL-$P_{14}$-acnB. The obtained strain was cultured at 37° C. in the LB medium containing 100 mg/L of ampicillin until OD600 became about 0.6. Then, a 40% glycerol solution in the same volume as the culture broth was added to the culture broth, and the mixture was stirred, then divided into appropriate volumes, and preserved at −80° C. This is referred to as glycerol stock of the AJIK01m2/pMW119-attR-cat-attL-$P_{14}$-acnB strain.

Example 3: Construction of L-Lysine-Producing Bacterium Having Enhanced Expression of acnB and aldB Genes (1) Construction of Plasmid pMW119-attR-Cat-attL-$P_{14}$-aldB for Enhancing expression of aldB gene PCR was performed by using the synthetic oligonucleotides shown as SEQ ID NOS: 12 and 13 as the primers, and the chromosomal DNA of the *Escherichia coli* MG1655 strain as the template to amplify a sequence containing the aldB gene. PCR was performed by using the synthetic oligonucleotides shown as SEQ ID NOS: 10 and 11 as the primers, and the plasmid pMW119-attR-cat-attL-$P_{14}$ as the template to amplify linear pMW119-attR-cat-attL-$P_{14}$. The sequence containing the aldB gene and linear pMW119-attR-cat-attL-$P_{14}$ were ligated by using In-Fusion HD Cloning Kit (Takara Bio) to construct a plasmid pMW119-attR-cat-attL-$P_{14}$-aldB, which expresses the aldB gene under the control of the promoter $P_{14}$.

(2) Construction of Plasmid pMW119-attR-Cat-attL-$P_{14}$-acnB-$P_{14}$-aldB for Enhancing Expression of acnB Gene and aldB Gene PCR was performed by using the synthetic oligonucleotides shown as SEQ ID NOS: 14 and 15 as the primers, and the plasmid pMW119-attR-cat-attL-$P_{14}$-acnB as the template to amplify a sequence containing $P_{14}$-acnB. PCR was performed by using the synthetic oligonucleotides shown as SEQ ID NOS: 16 and 17 as the primers, and the plasmid pMW119-attR-cat-attL-$P_{14}$-aldB as the template to amplify linear pMW119-attR-cat-attL-$P_{14}$-aldB. The sequence containing $P_{14}$-acnB and linear pMW119-attR-cat-attL-$P_{14}$-aldB were ligated by using In-Fusion HD Cloning Kit (Takara Bio) to construct a plasmid pMW119-attR-cat-attL-$P_{14}$-acnB-$P_{14}$-aldB, which expresses the acnB gene and aldB gene under the control of the promoter $P_{14}$.

The constructed plasmid pMW119-attR-cat-attL-$P_{14}$-acnB-$P_{14}$-aldB was introduced into the AJIK01m2 strain in a conventional manner to obtain a strain AJIK01m2/pMW119-attR-cat-attL-$P_{14}$-acnB-$P_{14}$-aldB. The obtained strain was cultured at 37° C. in the LB medium containing 100 mg/L of ampicillin until OD600 became about 0.6. Then, a 40% glycerol solution of the same volume as the culture broth was added to the culture broth, and the mixture was stirred, then divided into appropriate volumes, and preserved at −80° C. This is referred to as glycerol stock of the AJIK01m2/pMW119-attR-cat-attL-$P_{14}$-acnB-$P_{14}$-aldB strain.

Example 4: Construction of L-Lysine-Producing Bacterium Having Enhanced Expression of acnA and aldB Genes (1) Construction of Plasmid pMW119-attR-Cat-attL-$P_{14}$-acnA for Enhancing Expression of acnA Gene PCR was performed by using the synthetic oligonucleotides shown as SEQ ID NOS: 18 and 19 as the primers, and the chromosomal DNA of the *Escherichia coli* MG1655 strain as the template to amplify a sequence containing the acnA gene. PCR was performed by using the synthetic oligonucleotides shown as SEQ ID NOS: 10 and 11 as the primers, and the plasmid pMW119-attR-cat-attL-$P_{14}$ as the template to amplify linear pMW119-attR-cat-attL-$P_{14}$. The sequence containing the acnA gene and linear pMW119-attR-cat-attL-$P_{14}$ were ligated by using In-Fusion HD Cloning Kit (Takara Bio) to construct a plasmid pMW119-attR-cat-attL-$P_{14}$-acnA, which expresses the acnA gene under the control of the promoter $P_{14}$.

(2) Construction of Plasmid pMW119-attR-Cat-attL-$P_{14}$-acnA-$P_{14}$-aldB for Enhancing Expression of acnA Gene and aldB Gene PCR was performed by using the synthetic oligonucleotides shown as SEQ ID NOS: 14 and 20 as the primers, and the plasmid pMW119-attR-cat-attL-$P_{14}$-acnA as the template to amplify a sequence containing $P_{14}$-acnA. PCR was performed by using the synthetic oligonucleotides shown as SEQ ID NOS: 16 and 17 as the primers, and the plasmid pMW119-attR-cat-attL-$P_{14}$-aldB as the template to amplify linear pMW119-attR-cat-attL-$P_{14}$-aldB. The sequence containing $P_{14}$-acnA and linear pMW119-attR-cat-attL-$P_{14}$-aldB were ligated by using In-Fusion HD Cloning Kit (Takara Bio) to construct a plasmid pMW119-attR-cat-attL-$P_{14}$-acnA-$P_{14}$-aldB, which expresses the acnA gene and aldB gene under the control of the promoter $P_{14}$.

The constructed plasmid pMW119-attR-cat-attL-$P_{14}$-acnA-$P_{14}$-aldB was introduced into the AJIK01m2 strain in a conventional manner to obtain a strain AJIK01m2/pMW119-attR-cat-attL-$P_{14}$-acnA-$P_{14}$-aldB. The obtained strain was cultured at 37° C. in the LB medium containing 100 mg/L of ampicillin until OD600 became about 0.6. Then, a 40% glycerol solution in the same volume as the culture broth was added to the culture broth, and the mixture was stirred, then divided into appropriate volumes, and preserved at −80° C. This is referred to as glycerol stock of the AJIK01m2/pMW119-attR-cat-attL-$P_{14}$-acnA-$P_{14}$-aldB strain.

Example 5: Evaluation of L-Lysine-Producing Abilities of L-Lysine-Producing Bacteria The glycerol stocks obtained in Examples 2, 3, and 4 were each thawed, and about 100 μL of each was uniformly applied to an L plate containing 100 mg/L of ampicillin, and incubated at 37° C. for 16 hours as static culture. After the static culture, the obtained cells were suspended in 0.85% aqueous sodium chloride, inoculated into 25 mL of a fermentation medium (described below) containing 100 mg/L of ampicillin contained in a 500 mL-volume Sakaguchi flask so that the turbidity at a wavelength of 600 nm (OD600) became 0.2, and cultured at 37° C. for 24 hours under a condition of stirring at 120 rpm on a reciprocal shaking culture apparatus. After the shaking culture for 24 hours, 125 µL of ethanol was added to each flask, and shaking culture was continued for further 17 hours under the same condition.

Composition of the fermentation medium is shown below.

| | |
|---|---|
| Ethanol | 10 ml/L |
| $(NH_4)_2SO_4$ | 24 g/L |
| $KH_2PO_4$ | 1.0 g/L |
| $MgSO_4 \cdot 7H_2O$ | 1.0 g/L |
| $FeSO_4 \cdot 7H_2O$ | 0.01 g/L |
| $MnSO_4 \cdot 5H_2O$ | 0.082 g/L |
| Yeast extract (Difco) | 2.0 g/L |
| $CaCO_3$ (Japanese Pharmacopoeia) | 40 g/L |
| Distilled water | To the final volume of 1 L |

After the end of the culture, the amount of L-lysine accumulated in the medium was measured by using Biotech Analyzer AS310 (Sakura Seiki). Complete consumption of the carbon source (ethanol) added to the medium was confirmed by using Biotech Analyzer BF-5 (Oji Scientific Instruments). The amount of the cells at the end of the culture was measured by measuring the turbidity at a wavelength of 600 nm (OD600) of the culture broth appropriately diluted with 0.2 N dilute hydrochloric acid using a spectrophotometer U-2000 (Hitachi) immediately after the end of the culture.

The results are shown in Table 1. In Table 1, the names of the strains are mentioned in the column of "Strain", and the amounts of L-lysine accumulated in the medium are shown in the column of "Lys (g/L)". The strain having an enhanced expression of the acnB gene (AJIK01m2/pMW119-attR-cat-attL-$P_{14}$-acnB strain) showed significantly higher L-lysine production compared with the control strain (AJIK01m2/pMW119-attR-cat-attL-$P_{14}$ strain). That is, it was demonstrated that enhancement of the expression of the acnB gene improves L-lysine-producing ability. Furthermore, the strain having an enhanced expression of both the acnB and aldB genes (AJIK01m2/pMW119-attR-cat-attL-$P_{14}$-acnB-$P_{14}$-aldB strain) showed significantly higher L-lysine production compared with the control strain (AJIK01m2/pMW119-attR-cat-attL-$P_{14}$ strain). That is, it was demonstrated that simultaneous enhancement of the expressions of both the acnB gene and aldB gene improves L-lysine-producing ability. Furthermore, the strain having an enhanced expression of both the acnA and aldB genes (AJIK01m2/pMW119-attR-cat-attL-$P_{14}$-acnA-$P_{14}$-aldB strain) showed significantly higher L-lysine production compared with the control strain (AJIK01m2/pMW119-attR-cat-attL-$P_{14}$ strain). That is, it was demonstrated that simultaneous enhancement of the expressions of both the acnA gene and aldB gene improves L-lysine-producing ability.

TABLE 1

Evaluation of L-lysine-producing abilities of L-lysine-producing bacteria

| Strain | $OD_{600}$ | Lys (g/L) |
|---|---|---|
| AJIK01m2/pMW119-attR-cat-attL-$P_{14}$ | 12.1 | 6.98 |
| AJIK01m2/pMW119-attR-cat-attL-$P_{14}$-acnB | 12.6 | 7.12 |
| AJIK01m2/pMW119-attR-cat-attL-$P_{14}$-acnB-$P_{14}$-aldB | 12.0 | 7.25 |
| AJIK01m2/pMW119-attR-cat-attL-$P_{14}$-acnA-$P_{14}$-aldB | 13.3 | 7.25 |

INDUSTRIAL APPLICABILITY

According to the present invention, an L-amino acid-producing ability of a bacterium can be improved, and an L-amino acid can be efficiently produced.

EXPLANATION OF SEQUENCE LISTING

SEQ ID NOS:
1: Nucleotide sequence of promoter $P_{14}$
2-20: Primers
21: Nucleotide sequence of acnA gene of *Escherichia coli* K-12 MG1655
22: Amino acid sequence of AcnA protein of *Escherichia coli* K-12 MG1655
23: Nucleotide sequence of acnA gene of *Pantoea ananatis* AJ13355
24: Amino acid sequence of AcnA protein of *Pantoea ananatis* AJ13355
25: Nucleotide sequence of acnA gene of *Pectobacterium atrosepticum* SCRI1043
26: Amino acid sequence of AcnA protein of *Pectobacterium atrosepticum* SCRI1043
27: Nucleotide sequence of acnA gene of *Salmonella enterica* serovar *Typhi* CT18
28: Amino acid sequence of AcnA protein of *Salmonella enterica* serovar *Typhi* CT18
29: Nucleotide sequence of acnB gene of *Escherichia coli* K-12 MG1655
30: Amino acid sequence of AcnB protein of *Escherichia coli* K-12 MG1655
31: Nucleotide sequence of acnB gene of *Pantoea ananatis* AJ13355
32: Amino acid sequence of AcnB protein of *Pantoea ananatis* AJ13355
33: Nucleotide sequence of acnB gene of *Pectobacterium atrosepticum* SCRI1043
34: Amino acid sequence of AcnB protein of *Pectobacterium atrosepticum* SCRI1043
35: Nucleotide sequence of acnB gene of *Salmonella enterica* serovar *Typhi* CT18
36: Amino acid sequence of AcnB protein of *Salmonella enterica* serovar *Typhi* CT18
37: Nucleotide sequence of aldB gene of *Escherichia coli* K-12 MG1655
38: Amino acid sequence of A1 dB protein of *Escherichia coli* K-12 MG1655
39: Nucleotide sequence of aldB gene of *Pantoea ananatis* LMG 20103
40: Amino acid sequence of A1 dB protein of *Pantoea ananatis* LMG 20103
41: Nucleotide sequence of aldB gene of *Pectobacterium atrosepticum* SCRI1043
42: Amino acid sequence of A1 dB protein of *Pectobacterium atrosepticum* SCRI1043
43: Nucleotide sequence of aldB gene of *Salmonella enterica* serovar *Typhi* CT18
44: Amino acid sequence of A1 dB protein of *Salmonella enterica* serovar *Typhi* CT18
45: Nucleotide sequence of adhE gene of *Escherichia coli* K-12 MG1655
46: Amino acid sequence of AdhE protein of *Escherichia coli* K-12 MG1655
47: Nucleotide sequence of adhE gene of *Pantoea ananatis* LMG 20103
48: Amino acid sequence of AdhE protein of *Pantoea ananatis* LMG 20103

49: Nucleotide sequence of adhE gene of *Pectobacterium atrosepticum* SCRI1043
50: Amino acid sequence of AdhE protein of *Pectobacterium atrosepticum* SCRI1043
51: Nucleotide sequence of adhE gene of *Salmonella enterica* serovar *Typhi* CT18
52: Amino acid sequence of AdhE protein of *Salmonella enterica* serovar *Typhi* CT18

The invention claimed is:

1. A method for producing an L-amino acid, the method comprising:
   A) culturing an Enterobacteriaceae bacterium in a medium comprising ethanol as a carbon source, resulting in production and accumulation of the L-amino acid in the medium or cells of the bacterium, and
   B) collecting the L-amino acid from the medium or the cells of the bacterium;
   wherein the bacterium has been modified to increase the activities of aconitase and acetaldehyde dehydrogenase B (AldB) as compared with a corresponding non-modified Enterobacteriaceae bacterium,
   wherein the activity of the aconitase is increased by increasing the copy number of a gene encoding the aconitase, by modifying an expression control sequence of the gene encoding the aconitase, or by a combination thereof,
   wherein the activity of the AldB is increased by increasing the copy number of a gene encoding the AldB, by modifying an expression control sequence of the gene encoding the AldB, or by a combination thereof, and
   wherein the bacterium has an L-amino acid-producing ability in a medium comprising ethanol and is able to aerobically utilize ethanol as a carbon source.

2. The method according to claim 1, wherein the aconitase is an aconitase A (AcnA) protein or aconitase B (AcnB) protein.

3. The method according to claim 2, wherein the AcnA protein is a protein selected from the group consisting of:
   (a) a protein comprising the amino acid sequence of SEQ ID NO: 22, 24, 26, or 28,
   (b) a protein comprising the amino acid sequence of SEQ ID NO: 22, 24, 26, or 28, but wherein said sequence includes substitution, deletion, insertion, or addition of at least 1 and no more than 10 amino acid residues, and wherein said protein has aconitase activity, and
   (c) a protein comprising an amino acid sequence having an identity of 90% or higher to the amino acid sequence of SEQ ID NO: 22, 24, 26, or 28, and wherein said protein has aconitase activity.

4. The method according to claim 2, wherein the AcnB protein is a protein selected from the group consisting of:
   (a) a protein comprising the amino acid sequence of SEQ ID NO: 30, 32, 34, or 36,
   (b) a protein comprising the amino acid sequence of SEQ ID NO: 30, 32, 34, or 36, but wherein said sequence includes substitution, deletion, insertion, or addition of at least 1 and no more than 10 amino acid residues, and wherein said protein has aconitase activity, and
   (c) a protein comprising an amino acid sequence having an identity of 90% or higher to the amino acid sequence of SEQ ID NO: 30, 32, 34, or 36, and wherein said protein has aconitase activity.

5. The method according to claim 1, wherein the AldB protein is a protein selected from the group consisting of:
   (a) a protein comprising the amino acid sequence of SEQ ID NO: 38, 40, 42, or 44,
   (b) a protein comprising the amino acid sequence of SEQ ID NO: 38, 40, 42, or 44, but wherein said sequence includes substitution, deletion, insertion, or addition of at least 1 and no more than 10 amino acid residues, and wherein said protein has acetaldehyde dehydrogenase B activity, and
   (c) a protein comprising an amino acid sequence having an identity of 90% or higher to the amino acid sequence of SEQ ID NO: 38, 40, 42, or 44, and wherein said protein has acetaldehyde dehydrogenase B activity.

6. The method according to claim 1,
   wherein the bacterium has been further modified to increase an activity of an ethanol metabolic enzyme as compared with a corresponding non-modified Enterobacteriaceae bacterium by increasing the copy number of a gene encoding the ethanol metabolic enzyme, by modifying an expression control sequence of a gene encoding the ethanol metabolic enzyme, or by a combination thereof, and
   wherein the ethanol metabolic enzyme is selected from the group consisting of alcohol dehydrogenase, CoA-dependent acetaldehyde dehydrogenase, and combinations thereof.

7. The method according to claim 1,
   wherein the bacterium has been transformed with a polynucleotide encoding
   a mutant alcohol dehydrogenase E (AdhE) protein, and
   wherein the mutant AdhE protein has alcohol dehydrogenase activity and CoA-dependent acetaldehyde dehydrogenase activity and comprises the amino acid sequence of SEQ ID NO: 46, except for replacement of an amino acid residue corresponding to the glutamic acid residue at position 568 in the amino acid sequence of SEQ ID NO: 46 with an amino acid residue other than glutamic acid and aspartic acid, and optionally an additional mutation selected from the group consisting of:
   (A) replacement of an amino acid residue corresponding to the glutamic acid residue at position 560 in the amino acid sequence of SEQ ID NO: 46 with another amino acid residue,
   (B) replacement of an amino acid residue corresponding to the phenylalanine residue at position 566 in the amino acid sequence of SEQ ID NO: 46 with another amino acid residue,
   (C) replacement of amino acid residues corresponding to the glutamic acid residue at position 22, methionine residue at position 236, tyrosine residue at position 461, isoleucine residue at position 554, and alanine residue at position 786 in the amino acid sequence of SEQ ID NO: 46 with other amino acid residues, and
   (D) combinations thereof.

8. The method according to claim 7, wherein the replacement of an amino acid residue corresponding to the glutamic acid residue at position 568 in the amino acid sequence of SEQ ID NO: 46 is with lysine.

9. The method according to claim 1, wherein the bacterium is an *Escherichia* bacterium.

10. The method according to claim 9, wherein the bacterium is *Escherichia coli*.

11. The method according to claim 1, wherein the L-amino acid is L-lysine.

12. The method according to claim 11, wherein the bacterium further has a characteristic selected from the group consisting of:
    (A) the bacterium has been modified to increase activity or activities of an enzyme selected from the group consisting of dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, succinyldiaminopimelate deacylase, and combinations thereof as compared with a corresponding non-modified Enterobacteriaceae bacterium by increasing the copy number of a gene encoding the selected enzyme, by modifying an expression control sequence of the selected enzyme, or by a combination thereof,
(B) the bacterium has been modified to reduce activity of lysine decarboxylase as compared with a corresponding non-modified Enterobacteriaceae bacterium by disrupting a gene encoding the lysine decarboxylase, and
(C) combinations thereof.

* * * * *

SEQUENCE LISTING

<160> NUMBER OF SEQ ID NOS: 52

<210> SEQ ID NO 1
<211> LENGTH: 119
<212> TYPE: DNA
<213> ORGANISM: Artificial Sequence
<220> FEATURE:
<223> OTHER INFORMATION: promoter P14

<400> SEQUENCE: 1
cctgggtcat ttttttcttg acaaccgtca cattcttgat ggtatagtcg aaaactgcaa     60
aagcacatga cataaacaac ataagcacaa tcgtattaat atataagggt tttatatct    119

<210> SEQ ID NO 2
<211> LENGTH: 64
<212> TYPE: DNA
<213> ORGANISM: Artificial Sequence
<220> FEATURE:
<223> OTHER INFORMATION: primer

<400> SEQUENCE: 2
gcgggtaccg cggccgccct gggtcatttt tttcttgaca accgtcacat tcttgatggt     60
atag                                                                 64

<210> SEQ ID NO 3
<211> LENGTH: 47
<212> TYPE: DNA
<213> ORGANISM: Artificial Sequence
<220> FEATURE:
<223> OTHER INFORMATION: primer

<400> SEQUENCE: 3
gcgcgcgcgc gagctcgcgg ccgctcataa acgcctgaaa ttttgcc                   47

<210> SEQ ID NO 4
<211> LENGTH: 56
<212> TYPE: DNA
<213> ORGANISM: Artificial Sequence
<220> FEATURE:
<223> OTHER INFORMATION: primer

<400> SEQUENCE: 4
caggcttcaa gatctcctgg gtcatttttt tcttgacaac cgtcacattc ttgatg         56

<210> SEQ ID NO 5
<211> LENGTH: 67
<212> TYPE: DNA
<213> ORGANISM: Artificial Sequence
<220> FEATURE:
<223> OTHER INFORMATION: primer

<400> SEQUENCE: 5
atcctctaga gtcgacgcgg ccgctacggc aaaaacgcat cacttcacct tcgcttttc     60 ctttcgg                                                              67

<210> SEQ ID NO 6
<211> LENGTH: 67
<212> TYPE: DNA
<213> ORGANISM: Artificial Sequence

```
<220> FEATURE:
<223> OTHER INFORMATION: primer

<400> SEQUENCE: 6
tgattacgcc aagcttagga ggttaatcta gacgctcaag ttagtataaa aaagctgaac      60
gagaaac                                                               67

<210> SEQ ID NO 7
<211> LENGTH: 51
<212> TYPE: DNA
<213> ORGANISM: Artificial Sequence
<220> FEATURE:
<223> OTHER INFORMATION: primer

<400> SEQUENCE: 7
agatcttgaa gcctgctttt ttatactaag ttggcattat aaaaaagcat t               51

<210> SEQ ID NO 8
<211> LENGTH: 54
<212> TYPE: DNA
<213> ORGANISM: Artificial Sequence
<220> FEATURE:
<223> OTHER INFORMATION: primer

<400> SEQUENCE: 8
taagggtttt atatctatgc tagaagaata ccgtaagcac gtagctgagc gtgc            54

<210> SEQ ID NO 9
<211> LENGTH: 54
<212> TYPE: DNA
<213> ORGANISM: Artificial Sequence
<220> FEATURE:
<223> OTHER INFORMATION: primer

<400> SEQUENCE: 9
atcctctaga gtcgacttaa accgcagtct ggaaaatcac cccatcggct ttct            54

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
agatataaaa cccttatata ttaatacgat t                                     31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
gtcgactcta gaggatcccc gggtaccgag c                                     31

<210> SEQ ID NO 12
<211> LENGTH: 56
<212> TYPE: DNA
<213> ORGANISM: Artificial Sequence
<220> FEATURE:
<223> OTHER INFORMATION: primer
```

<400> SEQUENCE: 12
taagggtttt atatctatga ccaataatcc cccttcagca cagattaagc ccggcg        56

<210> SEQ ID NO 13
<211> LENGTH: 55
<212> TYPE: DNA
<213> ORGANISM: Artificial Sequence
<220> FEATURE:
<223> OTHER INFORMATION: primer

<400> SEQUENCE: 13
atcctctaga gtcgactcag aacagcccca acggtttatc cgagtagctc accag         55

<210> SEQ ID NO 14
<211> LENGTH: 50
<212> TYPE: DNA
<213> ORGANISM: Artificial Sequence
<220> FEATURE:
<223> OTHER INFORMATION: primer

<400> SEQUENCE: 14
gcaggcttca agatctcctg ggtcattttt ttcttgacaa ccgtcacatt              50

<210> SEQ ID NO 15
<211> LENGTH: 50
<212> TYPE: DNA
<213> ORGANISM: Artificial Sequence
<220> FEATURE:
<223> OTHER INFORMATION: primer

<400> SEQUENCE: 15
aaaaaaatga cccaggttaa accgcagtct ggaaaatcac cccatcggct              50

<210> SEQ ID NO 16
<211> LENGTH: 35
<212> TYPE: DNA
<213> ORGANISM: Artificial Sequence
<220> FEATURE:
<223> OTHER INFORMATION: primer

<400> SEQUENCE: 16
cctgggtcat tttttcttg acaaccgtca cattc                               35

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17
agatcttgaa gcctgctttt ttatactaag ttggc                              35

<210> SEQ ID NO 18
<211> LENGTH: 49
<212> TYPE: DNA
<213> ORGANISM: Artificial Sequence
<220> FEATURE:
<223> OTHER INFORMATION: primer

<400> SEQUENCE: 18
taagggtttt atatctatgt cgtcaaccct acgagaagcc agtaaggac               49

<210> SEQ ID NO 19
<211> LENGTH: 49
<212> TYPE: DNA
<213> ORGANISM: Artificial Sequence
<220> FEATURE:
<223> OTHER INFORMATION: primer

<400> SEQUENCE: 19

```
atcctctaga gtcgacttac ttcaacatat tacgaatgac ataatgcaa              49
```

<210> SEQ ID NO 20
<211> LENGTH: 52
<212> TYPE: DNA
<213> ORGANISM: Artificial Sequence
<220> FEATURE:
<223> OTHER INFORMATION: primer

<400> SEQUENCE: 20

```
aaaaaaatga cccaggttac ttcaacatat tacgaatgac ataatgcaaa at          52
```

<210> SEQ ID NO 21
<211> LENGTH: 2676
<212> TYPE: DNA
<213> ORGANISM: Escherichia coli

<400> SEQUENCE: 21

```
atgtcgtcaa ccctacgaga agccagtaag gacacgttgc aggccaaaga taaaacttac        60
cactactaca gcctgccgct tgctgctaaa tcactgggcg atatcacccg tctacccaag       120
tcactcaaag ttttgctcga aacctgctg cgctggcagg atggtaactc ggttaccgaa        180
gaggatatcc acgcgctggc aggatggctg aaaaatgccc atgctgaccg tgaaattgcc      240
taccgcccgg caagggtgct gatgcaggac tttaccggcg tacctgccgt tgttgatctg      300
gcggcaatgc gcgaagcggt taacgcctc ggcggcgata ctgcaaaggt taacccgctc       360
tcaccggtcg acctggtcat tgaccactcg gtgaccgtcg atcgttttgg tgatgatgag      420
gcatttgaag aaaacgtacg cctggaaatg gagcgcaacc acgaacgtta tgtgttcctg      480
aaatggggaa agcaagcgtt cagtcggttt agcgtcgtgc cgccaggcac aggcatttgc      540
catcaggtta acctcgaata tctcggcaaa gcagtgtgga gtgaattgca ggacggtgaa      600
tggattgctt atccggatac actcgttggt actgactcgc acaccaccat gatcaacggc      660
cttggcgtgc tggggtgggg cgttggtggg atcgaagcag aagccgcaat gttaggccag      720
ccggtttcca tgcttatccc ggatgtagtg ggcttcaaac ttaccggaaa attacgtgaa      780
ggtattaccg ccacagacct ggttctcact gttacccaaa tgctgcgcaa acatggcgtg      840
gtggggaaat cgtcgaatt ttatggtgat ggtctggatt cactaccgtt ggcggatcgc       900
gccaccattg ccaatatgtc gccagaatat ggtgccacct gtggcttctt cccaatcgat      960
gctgtaaccc tcgattacat gcgtttaagc gggcgcagcg aagatcaggt cgagttggtc     1020
gaaaaatatg ccaaagcgca gggcatgtgg cgtaacccgg gcgatgaacc aatttttacc     1080
agtacgttag aactggatat gaatgacgtt gaagcgagcc tggcagggcc taaacgccca     1140
caggatcgcg ttgcactgcc cgatgtacca aaagcatttg ccgccagtaa cgaactggaa     1200
gtgaatgcca cgcataaaga tcgccagccg gtcgattatg ttatgaacgg acatcagtat     1260
cagttacctg atggcgctgt ggtcattgct gcgataacct cgtgcaccaa cacctctaac     1320
ccaagtgtgc tgatggccgc aggcttgctg gcgaaaaaag ccgtaactct gggcctcaag     1380
cggcaaccat gggtcaaagc gtcgctggca ccgggttcga aagtcgtttc tgattatctg     1440
```

-continued

```
gcaaaagcga aactgacacc gtatctcgac gaactggggt ttaaccttgt gggatacggt    1500
tgtaccacct gtattggtaa ctctgggccg ctgcccgatc ctatcgaaac ggcaatcaaa    1560
aaaagcgatt taaccgtcgg tgcggtgctg tccggcaacc gtaactttga aggccgtatc    1620
catccgctgg ttaaaactaa ctggctggcc tcgccgccgc tggtggttgc ctatgcgctg    1680
gcgggaaata tgaatatcaa cctggcttct gagcctatcg ccatgatcg caaaggcgat     1740
ccggtttatc tgaaagatat ctggccatcg cacaagaaa ttgcccgtgc ggtagaacaa     1800
gtctccacag aaatgttccg caaagagtac gcagaagttt ttgaaggcac agcagagtgg    1860
aagggaatta acgtcacacg atccgatacc tacggttggc aggaggactc aacctatatt    1920
cgcttatcgc ctttctttga tgaaatgcag gcaacaccag caccagtgga agatattcac    1980
ggtgcgcgga tcctcgcaat gctgggggat tcagtcacca ctgaccatat ctctccggcg    2040
ggcagtatta agcccgacag cccagcgggt cgatatctac aaggtcgggg tgttgagcga    2100
aaagactta actcctacgg ttcgcggcgt ggtaaccatg aagtgatgat gcgcggcacc     2160
ttcgccaata ttcgcatccg taatgaaatg gtgcctggcg ttgaagggg gatgacgcgg     2220
catttacctg acagcgacgt agtctctatt tatgatgctg cgatgcgcta taagcaggag    2280
caaacgccgc tggcggtgat tgccgggaaa gagtatggac aggctccag tcgtgactgg     2340
gcggcaaaag tccgcgtctg cttggtatt cgtgtggtga ttgccgaatc gtttgaacga     2400
attaccgtt cgaatttaat tggcatgggc atcctgccgc tggaatttcc gcaaggcgta     2460
acgcgtaaaa cgttagggct aaccggggaa gagaagattg atattggcga tctgcaaaac    2520
ctacaacccg gcgcgacggt tccggtgacg cttacgcgcg cggatggtag ccaggaagtc    2580
gtaccctgcc gttgtcgtat cgacaccgcg acggagttga cctactacca gaacgacggc    2640
attttgcatt atgtcattcg taatatgttg aagtaa                               2676
```

<210> SEQ ID NO 22
<211> LENGTH: 891
<212> TYPE: PRT
<213> ORGANISM: Escherichia coli

<400> SEQUENCE: 22

```
Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
                20                  25                  30

Gly Asp Ile Thr Arg Leu Pro Lys Ser Leu Lys Val Leu Leu Glu Asn
            35                  40                  45

Leu Leu Arg Trp Gln Asp Gly Asn Ser Val Thr Glu Glu Asp Ile His
    50                  55                  60

Ala Leu Ala Gly Trp Leu Lys Asn Ala His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
                100                 105                 110

Asp Thr Ala Lys Val Asn Pro Leu Ser Pro Val Asp Leu Val Ile Asp
            115                 120                 125

His Ser Val Thr Val Asp Arg Phe Gly Asp Asp Glu Ala Phe Glu Glu
    130                 135                 140

Asn Val Arg Leu Glu Met Glu Arg Asn His Glu Arg Tyr Val Phe Leu
145                 150                 155                 160
```

```
Lys Trp Gly Lys Gln Ala Phe Ser Arg Phe Ser Val Pro Pro Gly
            165                 170                 175

Thr Gly Ile Cys His Gln Val Asn Leu Glu Tyr Leu Gly Lys Ala Val
        180                 185                 190

Trp Ser Glu Leu Gln Asp Gly Glu Trp Ile Ala Tyr Pro Asp Thr Leu
    195                 200                 205

Val Gly Thr Asp Ser His Thr Thr Met Ile Asn Gly Leu Gly Val Leu
    210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Asp Ser Leu Pro Leu Ala Asp Arg Ala Thr Ile Ala
    290                 295                 300

Asn Met Ser Pro Glu Tyr Gly Ala Thr Cys Gly Phe Phe Pro Ile Asp
305                 310                 315                 320

Ala Val Thr Leu Asp Tyr Met Arg Leu Ser Gly Arg Ser Glu Asp Gln
                325                 330                 335

Val Glu Leu Val Glu Lys Tyr Ala Lys Ala Gln Gly Met Trp Arg Asn
            340                 345                 350

Pro Gly Asp Glu Pro Ile Phe Thr Ser Thr Leu Glu Leu Asp Met Asn
        355                 360                 365

Asp Val Glu Ala Ser Leu Ala Gly Pro Lys Arg Pro Gln Asp Arg Val
    370                 375                 380

Ala Leu Pro Asp Val Pro Lys Ala Phe Ala Ala Ser Asn Glu Leu Glu
385                 390                 395                 400

Val Asn Ala Thr His Lys Asp Arg Gln Pro Val Asp Tyr Val Met Asn
                405                 410                 415

Gly His Gln Tyr Gln Leu Pro Asp Gly Ala Val Val Ile Ala Ala Ile
            420                 425                 430

Thr Ser Cys Thr Asn Thr Ser Asn Pro Ser Val Leu Met Ala Ala Gly
        435                 440                 445

Leu Leu Ala Lys Lys Ala Val Thr Leu Gly Leu Lys Arg Gln Pro Trp
    450                 455                 460

Val Lys Ala Ser Leu Ala Pro Gly Ser Lys Val Val Ser Asp Tyr Leu
465                 470                 475                 480

Ala Lys Ala Lys Leu Thr Pro Tyr Leu Asp Glu Leu Gly Phe Asn Leu
                485                 490                 495

Val Gly Tyr Gly Cys Thr Thr Cys Ile Gly Asn Ser Gly Pro Leu Pro
            500                 505                 510

Asp Pro Ile Glu Thr Ala Ile Lys Lys Ser Asp Leu Thr Val Gly Ala
        515                 520                 525

Val Leu Ser Gly Asn Arg Asn Phe Glu Gly Arg Ile His Pro Leu Val
    530                 535                 540

Lys Thr Asn Trp Leu Ala Ser Pro Pro Leu Val Val Ala Tyr Ala Leu
545                 550                 555                 560

Ala Gly Asn Met Asn Ile Asn Leu Ala Ser Glu Pro Ile Gly His Asp
                565                 570                 575

Arg Lys Gly Asp Pro Val Tyr Leu Lys Asp Ile Trp Pro Ser Ala Gln
            580                 585                 590
```

Glu Ile Ala Arg Ala Val Glu Gln Val Ser Thr Glu Met Phe Arg Lys
                595                 600                 605

Glu Tyr Ala Glu Val Phe Glu Gly Thr Ala Glu Trp Lys Gly Ile Asn
            610                 615                 620

Val Thr Arg Ser Asp Thr Tyr Gly Trp Gln Glu Asp Ser Thr Tyr Ile
625                 630                 635                 640

Arg Leu Ser Pro Phe Phe Asp Glu Met Gln Ala Thr Pro Ala Pro Val
                645                 650                 655

Glu Asp Ile His Gly Ala Arg Ile Leu Ala Met Leu Gly Asp Ser Val
            660                 665                 670

Thr Thr Asp His Ile Ser Pro Ala Gly Ser Ile Lys Pro Asp Ser Pro
        675                 680                 685

Ala Gly Arg Tyr Leu Gln Gly Arg Gly Val Glu Arg Lys Asp Phe Asn
690                 695                 700

Ser Tyr Gly Ser Arg Arg Gly Asn His Glu Val Met Met Arg Gly Thr
705                 710                 715                 720

Phe Ala Asn Ile Arg Ile Arg Asn Glu Met Val Pro Gly Val Glu Gly
                725                 730                 735

Gly Met Thr Arg His Leu Pro Asp Ser Asp Val Val Ser Ile Tyr Asp
            740                 745                 750

Ala Ala Met Arg Tyr Lys Gln Glu Gln Thr Pro Leu Ala Val Ile Ala
        755                 760                 765

Gly Lys Glu Tyr Gly Ser Gly Ser Ser Arg Asp Trp Ala Ala Lys Gly
770                 775                 780

Pro Arg Leu Leu Gly Ile Arg Val Val Ile Ala Glu Ser Phe Glu Arg
785                 790                 795                 800

Ile His Arg Ser Asn Leu Ile Gly Met Gly Ile Leu Pro Leu Glu Phe
                805                 810                 815

Pro Gln Gly Val Thr Arg Lys Thr Leu Gly Leu Thr Gly Glu Glu Lys
            820                 825                 830

Ile Asp Ile Gly Asp Leu Gln Asn Leu Gln Pro Gly Ala Thr Val Pro
835                 840                 845

Val Thr Leu Thr Arg Ala Asp Gly Ser Gln Glu Val Val Pro Cys Arg
850                 855                 860

Cys Arg Ile Asp Thr Ala Thr Glu Leu Thr Tyr Tyr Gln Asn Asp Gly
865                 870                 875                 880

Ile Leu His Tyr Val Ile Arg Asn Met Leu Lys
                885                 890

<210> SEQ ID NO 23
<211> LENGTH: 2682
<212> TYPE: DNA
<213> ORGANISM: Pantoea ananatis

<400> SEQUENCE: 23
atgtcgtcaa ccctacgcga gcagagtcag gaaacactgc aggtagataa tcaaaactat      60
cacatcttca gtctacctcg cgcatcacaa catctcggca acattgatcg tttgcctaaa     120
tccatgaaag ttctgctgga aaacctgctg cgctggcagg acggtgattc agtcacggaa     180
gaggatatcc aggcactggt cgactggcag aaaacggccc atggcgatcg ggaaattgcc     240
tatcgccctg cgcgtgtatt aatgcaggac ttcactggcg tgcctgccgt ggtggatttg     300
gccgccatgc gtgaggcggt gagtcgtctt ggcggcgacg tcgccaaagt gaatcctctg     360

```
tcgccggtcg atctggttat cgaccactct gtcacggttg accatttcgg cgacgataac    420
gcatttgaag aaaacgtgcg gctggaaatg gagcgcaacc atgaacgcta cgttttcctg    480
cgctggggcc aaaaggcttt tgatcagttt cgggtggtac cgccaggcac aggtatctgt    540
catcaggtga acctggaata cctgggcaaa gcgatctggc agcagaacat taacggtgaa    600
cgttacgcct ggcctgatac gttagtcgga accgattctc ataccaccat gatcaatgcc    660
ctgggtgtac tcggctgggg cgtgggcggg attgaggcag aggccgccat gcttggccag    720
ccggtttcta tgctgatccc cgacgtcgtg ggtttcaagc taaccgggaa actgcgtgcg    780
ggcatcaccg caaccgacct tgtacttacc gtcacgcaaa tgctgcgtaa gcacggcgtt    840
gtcgggaagt tgtcgagtt ctatggcgat ggcctggctg atctgccgct ggccgaccgt    900
gccaccattg ctaatatggc accagaatat ggcgcaacct gcggatttt cccggttgat    960 gaagttacac tcagctatat gacgctaacc ggacgcgatg ccgagcaggt ggcactggtt   1020
gaacactatg ctaagcgaca gggcctgtgg cgtaatgcgg gcgatgaacc gatttcacc    1080 agtagccttg cgctcgatat gaatgaagtc gagtcgagcc tggccggacc gaaacgtccg   1140
caggatcgcg tctcgctggg ggatgtgccc gccgctttcg atgccagcaa tgagctggaa   1200
gtgaaccatg cacagaaacc gcataagcag gtcgactata ccgacagcga accggcctg    1260 agccacacgc tgaccgatgg cgcggtggcg attgcggcga ttacctcctg taccaacacc   1320 tctaaccca gcgtgctgat ggccgcaggg ttactgcga aaaagcggt tgagcgggga    1380 ttaaaacgcc agccgtgggt caaagcgtcg ctggctccgg ttctaaagt ggtctccgac    1440 tatctcgcgg tcgcgcagct gacacctcat ctcgataaac tgggttttaa ccttgtgggc   1500
tacggttgta cgacctgtat cggtaactcg ggtccgctgc cggatgagat tgaatcggcc   1560
atcaaagaag gggatttaac ggtaggggcc gtcctgtccg gtaaccgcaa cttcgagggc   1620
cgtattcatc cgctgattaa aaccaactgg ctggcatcgc caccgctggt cgtcgcctat   1680
gcgctggcag gtaatatgaa aatcaacctg caaaccgacc cgctcggtca cgatcatcag   1740
ggcaagccgg tatttctgaa agacatctgg ccttcacctg aagagattgc gaccgccgtc   1800
cagcaggtca ccagcgatat gtatcacaaa gagtacgctg aggtatttaa cggcacgcca   1860
gagtggcagg ccattaaggt aagtgaagcg gctacctacg actgggatga aggatcaacc   1920
tacattcgcc tgtcgccct ctttgacgac atggaaaaag aacctaagcc ggttcaggat   1980
attcatggcg cgcgcctgct ggcgattctt ggcgattcgg tcaccactga ccacatctcg   2040
cctgccggta gcatcaaagc ggaaagtccg gccggtcgct atctgctgtc ccacggcgtg   2100
gagcggaatg attttaactc ctacggttca cggcgcggca accacgaagt gatgatgcgc   2160
gggacctttg cgaatatccg tattcgaaat gaaatggtgc ccggcgtgga aggggttac    2220 accaaacact accccagcgg tgagcagttg gccatttatg acgcggcgat gaaatatcag   2280
gctgacggca tttccctggc ggtgattgcg ggtaaagagt acggttcagg atcgagccgt   2340
gactgggcgg cgaaagggcc gcgtttgcaa ggcgtccgcg tggtaattgc ggaatccttc   2400
gaacgtattc accgttccaa cctgattggt atggggattt gccgctgga gttccctcag   2460 ggcgtaacgc gtaaaacgtt aggtctgaaa ggggatgagg cgatagatgt ggaaaacctg   2520
gcgcagctta aacccggatg caccgttttct gtcacgctaa cgcgcgcaga tggcagtcag   2580
gagaagctga atacgcgttg ccgtattgat accggtaatg aactgaccta ttaccgaaac   2640
gacggtattc tgcactacgt gattcgtaac atgctgaact ga                      2682
```

<210> SEQ ID NO 24
<211> LENGTH: 893
<212> TYPE: PRT
<213> ORGANISM: Pantoea ananatis

<400> SEQUENCE: 24

Met Ser Ser Thr Leu Arg Glu Gln Ser Gln Glu Thr Leu Gln Val Asp
1               5                   10                  15

Asn Gln Asn Tyr His Ile Phe Ser Leu Pro Arg Ala Ser Gln His Leu
            20                  25                  30

Gly Asn Ile Asp Arg Leu Pro Lys Ser Met Lys Val Leu Leu Glu Asn
        35                  40                  45

Leu Leu Arg Trp Gln Asp Gly Asp Ser Val Thr Glu Glu Asp Ile Gln
50                  55                  60

Ala Leu Val Asp Trp Gln Lys Thr Ala His Gly Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Ser Arg Leu Gly Gly
            100                 105                 110

Asp Val Ala Lys Val Asn Pro Leu Ser Pro Val Asp Leu Val Ile Asp
        115                 120                 125

His Ser Val Thr Val Asp His Phe Gly Asp Asp Asn Ala Phe Glu Glu
130                 135                 140

Asn Val Arg Leu Glu Met Glu Arg Asn His Glu Arg Tyr Val Phe Leu
145                 150                 155                 160

Arg Trp Gly Gln Lys Ala Phe Asp Gln Phe Arg Val Val Pro Pro Gly
                165                 170                 175

Thr Gly Ile Cys His Gln Val Asn Leu Glu Tyr Leu Gly Lys Ala Ile
            180                 185                 190

Trp Gln Gln Asn Ile Asn Gly Glu Arg Tyr Ala Trp Pro Asp Thr Leu
        195                 200                 205

Val Gly Thr Asp Ser His Thr Thr Met Ile Asn Ala Leu Gly Val Leu
210                 215                 220

Gly Trp Gly Val Gly Ile Glu Ala Glu Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Ala Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Ala Asp Leu Pro Leu Ala Asp Arg Ala Thr Ile Ala
290                 295                 300

Asn Met Ala Pro Glu Tyr Gly Ala Thr Cys Gly Phe Phe Pro Val Asp
305                 310                 315                 320

Glu Val Thr Leu Ser Tyr Met Thr Leu Thr Gly Arg Asp Ala Glu Gln
                325                 330                 335

Val Ala Leu Val Glu His Tyr Ala Lys Arg Gln Gly Leu Trp Arg Asn
            340                 345                 350

Ala Gly Asp Glu Pro Ile Phe Thr Ser Ser Leu Ala Leu Asp Met Asn
        355                 360                 365

Glu Val Glu Ser Ser Leu Ala Gly Pro Lys Arg Pro Gln Asp Arg Val
370                 375                 380

```
Ser Leu Gly Asp Val Pro Ala Ala Phe Asp Ala Ser Asn Glu Leu Glu
385                 390                 395                 400

Val Asn His Ala Gln Lys Pro His Lys Gln Val Asp Tyr Thr Asp Ser
            405                 410                 415

Glu Thr Gly Leu Ser His Thr Leu Thr Asp Gly Ala Val Ala Ile Ala
            420                 425                 430

Ala Ile Thr Ser Cys Thr Asn Thr Ser Asn Pro Ser Val Leu Met Ala
            435                 440                 445

Ala Gly Leu Leu Ala Lys Lys Ala Val Glu Arg Gly Leu Lys Arg Gln
    450                 455                 460

Pro Trp Val Lys Ala Ser Leu Ala Pro Gly Ser Lys Val Val Ser Asp
465                 470                 475                 480

Tyr Leu Ala Val Ala Gln Leu Thr Pro His Leu Asp Lys Leu Gly Phe
                485                 490                 495

Asn Leu Val Gly Tyr Gly Cys Thr Thr Cys Ile Gly Asn Ser Gly Pro
                500                 505                 510

Leu Pro Asp Glu Ile Glu Ser Ala Ile Lys Glu Gly Asp Leu Thr Val
            515                 520                 525

Gly Ala Val Leu Ser Gly Asn Arg Asn Phe Glu Gly Arg Ile His Pro
    530                 535                 540

Leu Ile Lys Thr Asn Trp Leu Ala Ser Pro Pro Leu Val Val Ala Tyr
545                 550                 555                 560

Ala Leu Ala Gly Asn Met Lys Ile Asn Leu Gln Thr Asp Pro Leu Gly
                565                 570                 575

His Asp His Gln Gly Lys Pro Val Phe Leu Lys Asp Ile Trp Pro Ser
            580                 585                 590

Pro Glu Glu Ile Ala Thr Ala Val Gln Gln Val Thr Ser Asp Met Tyr
            595                 600                 605

His Lys Glu Tyr Ala Glu Val Phe Asn Gly Thr Pro Glu Trp Gln Ala
    610                 615                 620

Ile Lys Val Ser Glu Ala Ala Thr Tyr Asp Trp Asp Glu Gly Ser Thr
625                 630                 635                 640

Tyr Ile Arg Leu Ser Pro Phe Phe Asp Asp Met Glu Lys Glu Pro Lys
                645                 650                 655

Pro Val Gln Asp Ile His Gly Ala Arg Leu Leu Ala Ile Leu Gly Asp
            660                 665                 670

Ser Val Thr Thr Asp His Ile Ser Pro Ala Gly Ser Ile Lys Ala Glu
    675                 680                 685

Ser Pro Ala Gly Arg Tyr Leu Leu Ser His Gly Val Glu Arg Asn Asp
    690                 695                 700

Phe Asn Ser Tyr Gly Ser Arg Arg Gly Asn His Glu Val Met Met Arg
705                 710                 715                 720

Gly Thr Phe Ala Asn Ile Arg Ile Arg Asn Glu Met Val Pro Gly Val
                725                 730                 735

Glu Gly Gly Tyr Thr Lys His Tyr Pro Ser Gly Glu Gln Leu Ala Ile
            740                 745                 750

Tyr Asp Ala Ala Met Lys Tyr Gln Ala Asp Gly Ile Pro Leu Ala Val
            755                 760                 765

Ile Ala Gly Lys Glu Tyr Gly Ser Gly Ser Ser Arg Asp Trp Ala Ala
    770                 775                 780

Lys Gly Pro Arg Leu Gln Gly Val Arg Val Val Ile Ala Glu Ser Phe
785                 790                 795                 800

Glu Arg Ile His Arg Ser Asn Leu Ile Gly Met Gly Ile Leu Pro Leu
                805                 810                 815
```

```
Glu Phe Pro Gln Gly Val Thr Arg Lys Thr Leu Gly Leu Lys Gly Asp
                820                 825                 830

Glu Ala Ile Asp Val Glu Asn Leu Ala Gln Leu Lys Pro Gly Cys Thr
            835                 840                 845

Val Ser Val Thr Leu Thr Arg Ala Asp Gly Ser Gln Glu Lys Leu Asp
        850                 855                 860

Thr Arg Cys Arg Ile Asp Thr Gly Asn Glu Leu Thr Tyr Tyr Arg Asn
865                 870                 875                 880

Asp Gly Ile Leu His Tyr Val Ile Arg Asn Met Leu Asn
                885                 890

<210> SEQ ID NO 25
<211> LENGTH: 2673
<212> TYPE: DNA
<213> ORGANISM: Pectobacterium atrosepticum

<400> SEQUENCE: 25
atgtcatcac accttcgcga cacttgtctg gacacactga cggttcgaca gcagatttac      60
cattactaca gcctgccgaa ggcggcgaaa acgcttggca atatcgataa attaccgaag     120
tcactcaagg tattgctgga aaatttattg cgtcatcagg acggcgacac ggtcgagcag     180
gacgatcttc aggcggtcgt ggactggctg aaaatcggtc acgccgatcg ggaaatcgcc     240
tatcggccag cgcgcgtact gatgcaggac tttaccggcg tgcccgccgt ggtcgatctg     300
gcggcgatgc gtgcagcggt gaaacggttg gcggcgatg ttaataaggt caacccgctg     360
tcgccggtcg atctggttat tgaccactcg gttacggttg atcacttcgg cgatcgtcag     420
gcgctagcgg ataacacgca gttggaaatg cgcgtaacc gtgaacgtta tgagtttttg     480
cgctggggac aaaatgcctt tagccacttc agcgtcgtgc cgccgggaac cgggatctgc     540
catcaggtga atctggagta tctcgccaag gccatctggt acgaaaaaca gggcgacaaa     600
cagtttgcct accctgatac gctggtagga accgattcgc acaccaccat gattaacggt     660
ttgggcgtgc tcggctgggg tgtcggtggg atagaagcag aagccgcgat gttggggcaa     720
cctgtttcga tgctgattcc cgatgtggtt ggcgtcaaat taagcggcaa aatgcaagaa     780
gggatcacgc aaccgatttg gttctgacg gtaacgcaga tgctgcgtaa acacggcgtt     840
gtcggcaaat ttgtggaatt ttacggtgat gggctggatt ctctaccgtt ggcagatcgc     900
gcgactatcg ccaacatggc accggaatat ggtgcaacct gtggcttttt ccctatcgat     960
cacatcacgc tggattacat gcggttgacc aaccgcgccg aagaacagat tgcactggtg    1020
gaagcctaca gtaagcaaca ggggctgtgg cgcaatgctg agatgagcc ggtattcacc    1080 agccagctag cgctggattt ggcaacggtg gaaaccagtc tggcagggcc gaaacgccca    1140
caggatcgcg tgcctttagc gggtgtgccg gaagccttta agccagccg ggaactggat    1200 gtcagctcgg tgaagaaccg ctctgactat gaagagttca cgttggaagg tgagacgcat    1260
cgcttgcatc aggggcgt cgtgatcgcg gcgatcacct cttgtactaa tacctccaac    1320
cctagcgtgc tgatgacggc tgggctactg gcaaaaaatg ccgtagagcg tggtcttaaa    1380
accaagccgt gggtcaaaac ctcgttggca ccgggctcac gggtcgtcac ggattactat    1440
gctaaagcgg aattaacgcc atacctcgac gagttggggt caatctggt ggggtacggc    1500 tgtaccacct gtatcggtaa ctccggcccc ctgccggatg cgattgaagc gcgataaa    1560 gaaggcgact tgacggtcgg cgccgtgttg tcaggtaacc gtaactttga aggccgtatt    1620
catccgctgg tgaagactaa ctggctggcg tcaccgccgc tggtggtcgc ctacgcgctg    1680
```

```
gcgggaaata tgaatgtcga tctgacgcaa caaccgctgg gtgaagatcg tgacggaaaa    1740
gccgtttatc tgaaagacat ctggccctcg acgaaagcgg tggcggacgc ggtattgaat    1800
gtcaacgctg gcatgttcca caaacaatat gccgcagtgt ttgaaggtac gcaggagtgg    1860
caagatatcg aggtcgacga taatcctacc tatcagtggc cggaagaatc gacctatatt    1920
cgccagacgc ctttcttttct ggatatgggg aaagaaccgg agccggttca ggatatccac    1980
aaggcgcgca ttctggcgat gctgggcgat tcggttacaa ccgaccacat ctcgccagca    2040
ggcaacatca agcgtgatag ccctgcaggg aaatatttgc tggaacgcgg cgttgaaacc    2100
acggagttca actcttacgg ttcacggcgg ggcaaccacg aagtgatgat gcgcgggacg    2160
tttgccaaca tccgtatccg taatgaaatg gtgccgggta agagggcgg ttatacccgt    2220 cacattccgt cgcagaatga gatgacgatc tatgacgcgg caatgcgcta caaggaagaa    2280
ggtgtctcac tggcgctgtt tgctgggaaa gagtacggtt cgggttctag ccgagactgg    2340
gccgcgaaag gcccacgttt gctgggtgtt cgcgtggtga tcgccgaatc gttcgagcgt    2400
attcaccgct ctaacctgat tgggatgggg attctgccgc tggaatttcc cgacggtgtg    2460
acgcgtaaaa cgctgcaatt aaccggggat gagcagattt cgattacggg attaaatcaa    2520
ctggcacctg cgccacggt tgaggtaaat atcacggatg ctgatggtaa tacgcaggtg    2580
atcaacaccc gctgccgcat cgacacccgt aatgaactga cctattacca gaacgacggt    2640
atccttcatt acgttatccg taatatgttg taa                                 2673
```

<210> SEQ ID NO 26
<211> LENGTH: 890
<212> TYPE: PRT
<213> ORGANISM: Pectobacterium atrosepticum

<400> SEQUENCE: 26

```
Met Ser Ser His Leu Arg Asp Thr Cys Leu Asp Thr Leu Thr Val Arg
1               5                   10                  15

Gln Gln Ile Tyr His Tyr Tyr Ser Leu Pro Lys Ala Ala Lys Thr Leu
            20                  25                  30

Gly Asn Ile Asp Lys Leu Pro Lys Ser Leu Lys Val Leu Leu Glu Asn
        35                  40                  45

Leu Leu Arg His Gln Asp Gly Asp Thr Val Glu Gln Asp Asp Leu Gln
    50                  55                  60

Ala Val Val Asp Trp Leu Lys Ile Gly His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Ala Ala Val Lys Arg Leu Gly Gly
            100                 105                 110

Asp Val Asn Lys Val Asn Pro Leu Ser Pro Val Asp Leu Val Ile Asp
        115                 120                 125

His Ser Val Thr Val Asp His Phe Gly Asp Arg Gln Ala Leu Ala Asp
    130                 135                 140

Asn Thr Gln Leu Glu Met Ala Arg Asn Arg Glu Arg Tyr Glu Phe Leu
145                 150                 155                 160

Arg Trp Gly Gln Asn Ala Phe Ser His Phe Ser Val Val Pro Pro Gly
                165                 170                 175

Thr Gly Ile Cys His Gln Val Asn Leu Glu Tyr Leu Ala Lys Ala Ile
            180                 185                 190
```

```
Trp Tyr Glu Lys Gln Gly Asp Lys Gln Phe Ala Tyr Pro Asp Thr Leu
            195                 200                 205

Val Gly Thr Asp Ser His Thr Thr Met Ile Asn Gly Leu Gly Val Leu
        210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Val Lys Leu Ser Gly
                245                 250                 255

Lys Met Gln Glu Gly Ile Thr Ala Thr Asp Leu Val Leu Thr Val Thr
                260                 265                 270

Gln Met Leu Arg Lys His Gly Val Val Gly Lys Phe Val Glu Phe Tyr
            275                 280                 285

Gly Asp Gly Leu Asp Ser Leu Pro Leu Ala Asp Arg Ala Thr Ile Ala
290                 295                 300

Asn Met Ala Pro Glu Tyr Gly Ala Thr Cys Gly Phe Phe Pro Ile Asp
305                 310                 315                 320

His Ile Thr Leu Asp Tyr Met Arg Leu Thr Asn Arg Ala Glu Glu Gln
                325                 330                 335

Ile Ala Leu Val Glu Ala Tyr Ser Lys Gln Gln Gly Leu Trp Arg Asn
                340                 345                 350

Ala Gly Asp Glu Pro Val Phe Thr Ser Gln Leu Ala Leu Asp Leu Ala
            355                 360                 365

Thr Val Glu Thr Ser Leu Ala Gly Pro Lys Arg Pro Gln Asp Arg Val
            370                 375                 380

Pro Leu Ala Gly Val Pro Glu Ala Phe Lys Ala Ser Arg Glu Leu Asp
385                 390                 395                 400

Val Ser Ser Val Lys Asn Arg Ser Asp Tyr Glu Glu Phe Thr Leu Glu
                405                 410                 415

Gly Glu Thr His Arg Leu His Gln Gly Ala Val Val Ile Ala Ala Ile
                420                 425                 430

Thr Ser Cys Thr Asn Thr Ser Asn Pro Ser Val Leu Met Thr Ala Gly
            435                 440                 445

Leu Leu Ala Lys Asn Ala Val Glu Arg Gly Leu Lys Thr Lys Pro Trp
            450                 455                 460

Val Lys Thr Ser Leu Ala Pro Gly Ser Arg Val Val Thr Asp Tyr Tyr
465                 470                 475                 480

Ala Lys Ala Glu Leu Thr Pro Tyr Leu Asp Glu Leu Gly Phe Asn Leu
                485                 490                 495

Val Gly Tyr Gly Cys Thr Thr Cys Ile Gly Asn Ser Gly Pro Leu Pro
                500                 505                 510

Asp Ala Ile Glu Ala Ala Ile Lys Glu Gly Asp Leu Thr Val Gly Ala
            515                 520                 525

Val Leu Ser Gly Asn Arg Asn Phe Glu Gly Arg Ile His Pro Leu Val
            530                 535                 540

Lys Thr Asn Trp Leu Ala Ser Pro Pro Leu Val Val Ala Tyr Ala Leu
545                 550                 555                 560

Ala Gly Asn Met Asn Val Asp Leu Thr Gln Gln Pro Leu Gly Glu Asp
                565                 570                 575

Arg Asp Gly Lys Ala Val Tyr Leu Lys Asp Ile Trp Pro Ser Thr Lys
            580                 585                 590

Ala Val Ala Asp Ala Val Leu Asn Val Asn Ala Gly Met Phe His Lys
            595                 600                 605
```

Gln Tyr Ala Ala Val Phe Glu Gly Thr Gln Glu Trp Gln Asp Ile Glu
            610                 615                 620

Val Asp Asp Asn Pro Thr Tyr Gln Trp Pro Glu Glu Ser Thr Tyr Ile
625                 630                 635                 640

Arg Gln Thr Pro Phe Phe Leu Asp Met Gly Lys Glu Pro Glu Pro Val
                645                 650                 655

Gln Asp Ile His Lys Ala Arg Ile Leu Ala Met Leu Gly Asp Ser Val
            660                 665                 670

Thr Thr Asp His Ile Ser Pro Ala Gly Asn Ile Lys Arg Asp Ser Pro
        675                 680                 685

Ala Gly Lys Tyr Leu Leu Glu Arg Gly Val Glu Thr Thr Glu Phe Asn
690                 695                 700

Ser Tyr Gly Ser Arg Arg Gly Asn His Glu Val Met Met Arg Gly Thr
705                 710                 715                 720

Phe Ala Asn Ile Arg Ile Arg Asn Glu Met Val Pro Gly Lys Glu Gly
                725                 730                 735

Gly Tyr Thr Arg His Ile Pro Ser Gln Asn Glu Met Thr Ile Tyr Asp
            740                 745                 750

Ala Ala Met Arg Tyr Lys Glu Glu Gly Val Ser Leu Ala Leu Phe Ala
        755                 760                 765

Gly Lys Glu Tyr Gly Ser Gly Ser Ser Arg Asp Trp Ala Ala Lys Gly
770                 775                 780

Pro Arg Leu Leu Gly Val Arg Val Val Ile Ala Glu Ser Phe Glu Arg
785                 790                 795                 800

Ile His Arg Ser Asn Leu Ile Gly Met Gly Ile Leu Pro Leu Glu Phe
                805                 810                 815

Pro Asp Gly Val Thr Arg Lys Thr Leu Gln Leu Thr Gly Asp Glu Gln
            820                 825                 830

Ile Ser Ile Thr Gly Leu Asn Gln Leu Ala Pro Gly Ala Thr Val Glu
        835                 840                 845

Val Asn Ile Thr Asp Ala Asp Gly Asn Thr Gln Val Ile Asn Thr Arg
850                 855                 860

Cys Arg Ile Asp Thr Arg Asn Glu Leu Thr Tyr Tyr Gln Asn Asp Gly
865                 870                 875                 880

Ile Leu His Tyr Val Ile Arg Asn Met Leu
                885                 890

<210> SEQ ID NO 27
<211> LENGTH: 2676
<212> TYPE: DNA
<213> ORGANISM: Salmonella enterica

<400> SEQUENCE: 27
atgtcgtcaa ccctacgaga agccagtaag gatacattgc aggccaaaga taaaacgtat      60
cattactaca gtctgccgct ggctgccaaa tccctgggcg atatcgcccg tttgcccaaa     120
tcacttaaag tgttactgga aaacctgttg cgctggcagg acggcgaatc tgtgactgat     180
gaagatattc aggcgctggc cggttggctt aaaaatgccc atgccgatcg tgaaattgct     240
tggcggcccg cccgtgtcct gatgcaggac tttaccggcg tgcctgccgt tgtcgacctg     300
gcggcgatgc gtgaagccgt taaacgcctc ggcggcgata cgtcgaaagt gaacccgtta     360
tcgccggttg atctggttat tgaccactct gtgacggtcg atcatttcgg cgatgatgat     420
gcgtttgaag aaaacgtgcg gctggaaatg aacgtaacc atgagcgtta tatgttcctg     480
aaatggggaa agcaggcatt cagccgtttc agcgtggtgc cgcccggcac cggcatttgc     540

```
catcaggtta acctggaata cctgggtaaa gccatctgga gcgaattaca ggacggggag      600
tggattgctt acccggactc gctggtgggg actgactccc atacgaccat gattaatggt      660
ctgggcgtat tggggtgggg cgtgggtggt attgaagcgg aagcggcgat gcttggtcag      720
cccgtgtcga tgcttatccc ggatgtcgtc ggctttaagt taaccggtaa acttcgggag      780
gggatcactg ccactgacct ggtgctaacc gtcacgcaaa tgctgcgtaa gcatggcgtc      840
gtgggtaaat tgttgaatt ttatggtgac ggtctggatt cgctgccgtt ggcggatcgc       900
gcgactatcg ctaatatgtc gccggaatat ggcgccacct gtggtttctt ccccattgac      960
gccatcacct tggaatatat gcgattaagc ggacgtagcg acgatctgat cgagctggtt     1020
gaaacctacg cgaaggcgca gggaatgtgg cgtaatcccg gtgacgaacc ggtatttacc     1080
agtacgctgg aactggatat gggcgatgtc gaggccagcc tggccgggcc gaaacgcccg     1140
caggatcgcg tggcgttagg cgatgtgccg aaagcctttg ccgccagcgc cgagctggag     1200
ctgaataccg cgcaaagaga tcgccagccg gttgactata cgatgaacgg acagccatat     1260
cagcttccgg atggcgctgt cgtcattgcc gccatcacct cctgtacgaa tacctcgaat     1320
cccagcgtgc tgatggcggc gggattactg gcgaaaaagg cagtaacgct ggggttgaag     1380
cgtcaaccgt gggtcaaggc ttctctggcg ccggggtcaa aagtggtatc tgactatctg     1440
gcgcaggcca aacttacgcc ttatctggat gagctcggtt ttaacctggt cggctatggc     1500
tgtacgacct gtatcgggaa ctccggtccg ttgccggagc ctattgagac cgcgattaaa     1560
aaaggcgatc tgacggtagg ggccgtgctt tccggtaacc gaaattttga agggcgtatc     1620
catccgctgg tgaaaacgaa ctggctggtg tcgccgccgc tggtggtcgc gtatgcgctg     1680
gccggaaaca tgaatattaa cctcgcgaca gacccgctgg ggtacgatcg taaaggcgat     1740
ccggtatacc tgaaggatat ctggccttcg gcgcaggaaa ttgcccgcgc cgttgaactg     1800
gtatcatcgg atatgttccg taaagagtat gcggaagtgt ttgagggcac ggaagaatgg     1860
aaatcgattc aggttgaatc gtccgatacc tacggctggc agtcggattc aacctatatc     1920
cgcctgtcgc cttttctttga tgaaatgcag gcccagcctg cacccgtcaa agatatccac     1980
ggcgcgcgta tcctggcgat gctgggcgat tcggtgacga ccgaccatat ttcccccggcc     2040 ggcagtatca agccggacag tcccgccgga cgctatctgc aaaaccacgg cgttgagcgg     2100
aaggatttta actcctatgg atcacggcgc ggcaaccatg aagtgatgat gcgcggtacg     2160
ttcgccaata ttcgtattcg caacgaaatg ctgcccggcg tcgaaggtgg gatgacgcgg     2220
catttgccgg gtacggaagc gatgtcgatt tatgatgccg cgatgctcta ccagcaggaa     2280
aaaacgccgc tggcggtaat tgccgggaaa gagtatgggt cggatcgag ccgtgactgg      2340 gcggcaaaag gtccgcggct gttaggtatt cgcgtggtga tcgccgagtc gttcgaacgt     2400
atccatcgct caagcctgat tgggatgggg atcctgccgc tggagtttcc acagggcgta     2460
acgcgtaaaa cgctgggact gaccggggaa gaggtgattg atatcgcgga tctgcaaaat     2520
ctgcgccctg gcgcgaccat tccggttatg ttaacgagag cggacggcag caaagaaacg     2580
gtgccttgtc gctgtcgcat tgataccgcc accgagctga cttactacca gaatgacggc     2640
atattgcact atgtcattag aaatatgctg aactaa                                2676
```

<210> SEQ ID NO 28
<211> LENGTH: 891
<212> TYPE: PRT
<213> ORGANISM: Salmonella enterica

```
<400> SEQUENCE: 28

Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
            20                  25                  30

Gly Asp Ile Ala Arg Leu Pro Lys Ser Leu Lys Val Leu Leu Glu Asn
                35                  40                  45

Leu Leu Arg Trp Gln Asp Gly Glu Ser Val Thr Asp Glu Asp Ile Gln
    50                  55                  60

Ala Leu Ala Gly Trp Leu Lys Asn Ala His Ala Asp Arg Glu Ile Ala
65                  70                  75                  80

Trp Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
            100                 105                 110

Asp Thr Ser Lys Val Asn Pro Leu Ser Pro Val Asp Leu Val Ile Asp
                115                 120                 125

His Ser Val Thr Val Asp His Phe Gly Asp Asp Ala Phe Glu Glu
            130                 135                 140

Asn Val Arg Leu Glu Met Glu Arg Asn His Glu Arg Tyr Met Phe Leu
145                 150                 155                 160

Lys Trp Gly Lys Gln Ala Phe Ser Arg Phe Ser Val Val Pro Pro Gly
                165                 170                 175

Thr Gly Ile Cys His Gln Val Asn Leu Glu Tyr Leu Gly Lys Ala Ile
            180                 185                 190

Trp Ser Glu Leu Gln Asp Gly Glu Trp Ile Ala Tyr Pro Asp Ser Leu
    195                 200                 205

Val Gly Thr Asp Ser His Thr Thr Met Ile Asn Gly Leu Gly Val Leu
    210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Asp Ser Leu Pro Leu Ala Asp Arg Ala Thr Ile Ala
    290                 295                 300

Asn Met Ser Pro Glu Tyr Gly Ala Thr Cys Gly Phe Phe Pro Ile Asp
305                 310                 315                 320

Ala Ile Thr Leu Glu Tyr Met Arg Leu Ser Gly Arg Ser Asp Asp Leu
                325                 330                 335

Ile Glu Leu Val Glu Thr Tyr Ala Lys Ala Gln Gly Met Trp Arg Asn
            340                 345                 350

Pro Gly Asp Glu Pro Val Phe Thr Ser Thr Leu Glu Leu Asp Met Gly
        355                 360                 365

Asp Val Glu Ala Ser Leu Ala Gly Pro Lys Arg Pro Gln Asp Arg Val
    370                 375                 380

Ala Leu Gly Asp Val Pro Lys Ala Phe Ala Ala Ser Ala Glu Leu Glu
385                 390                 395                 400

Leu Asn Thr Ala Gln Arg Asp Arg Gln Pro Val Asp Tyr Thr Met Asn
                405                 410                 415
```

```
Gly Gln Pro Tyr Gln Leu Pro Asp Gly Ala Val Ile Ala Ala Ile
                420                 425                 430

Thr Ser Cys Thr Asn Thr Ser Asn Pro Ser Val Leu Met Ala Ala Gly
    435                 440                 445

Leu Leu Ala Lys Lys Ala Val Thr Leu Gly Leu Lys Arg Gln Pro Trp
450                 455                 460

Val Lys Ala Ser Leu Ala Pro Gly Ser Lys Val Val Ser Asp Tyr Leu
465                 470                 475                 480

Ala Gln Ala Lys Leu Thr Pro Tyr Leu Asp Glu Leu Gly Phe Asn Leu
                485                 490                 495

Val Gly Tyr Gly Cys Thr Thr Cys Ile Gly Asn Ser Gly Pro Leu Pro
                500                 505                 510

Glu Pro Ile Glu Thr Ala Ile Lys Lys Gly Asp Leu Thr Val Gly Ala
                515                 520                 525

Val Leu Ser Gly Asn Arg Asn Phe Glu Gly Arg Ile His Pro Leu Val
                530                 535                 540

Lys Thr Asn Trp Leu Val Ser Pro Pro Leu Val Val Ala Tyr Ala Leu
545                 550                 555                 560

Ala Gly Asn Met Asn Ile Asn Leu Ala Thr Asp Pro Leu Gly Tyr Asp
                565                 570                 575

Arg Lys Gly Asp Pro Val Tyr Leu Lys Asp Ile Trp Pro Ser Ala Gln
                580                 585                 590

Glu Ile Ala Arg Ala Val Glu Leu Val Ser Ser Asp Met Phe Arg Lys
                595                 600                 605

Glu Tyr Ala Glu Val Phe Glu Gly Thr Glu Gly Trp Lys Ser Ile Gln
                610                 615                 620

Val Glu Ser Ser Asp Thr Tyr Gly Trp Gln Ser Asp Ser Thr Tyr Ile
625                 630                 635                 640

Arg Leu Ser Pro Phe Phe Asp Glu Met Gln Ala Gln Pro Ala Pro Val
                645                 650                 655

Lys Asp Ile His Gly Ala Arg Ile Leu Ala Met Leu Gly Asp Ser Val
                660                 665                 670

Thr Thr Asp His Ile Ser Pro Ala Gly Ser Ile Lys Pro Asp Ser Pro
                675                 680                 685

Ala Gly Arg Tyr Leu Gln Asn His Gly Val Glu Arg Lys Asp Phe Asn
                690                 695                 700

Ser Tyr Gly Ser Arg Arg Gly Asn His Glu Val Met Met Arg Gly Thr
705                 710                 715                 720

Phe Ala Asn Ile Arg Ile Arg Asn Glu Met Leu Pro Gly Val Glu Gly
                725                 730                 735

Gly Met Thr Arg His Leu Pro Gly Thr Glu Ala Met Ser Ile Tyr Asp
                740                 745                 750

Ala Ala Met Leu Tyr Gln Gln Glu Lys Thr Pro Leu Ala Val Ile Ala
                755                 760                 765

Gly Lys Glu Tyr Gly Ser Gly Ser Ser Arg Asp Trp Ala Ala Lys Gly
770                 775                 780

Pro Arg Leu Leu Gly Ile Arg Val Val Ile Ala Glu Ser Phe Glu Arg
785                 790                 795                 800

Ile His Arg Ser Ser Leu Ile Gly Met Gly Ile Leu Pro Leu Glu Phe
                805                 810                 815

Pro Gln Gly Val Thr Arg Lys Thr Leu Gly Leu Thr Gly Glu Glu Val
                820                 825                 830
```

```
Ile Asp Ile Ala Asp Leu Gln Asn Leu Arg Pro Gly Ala Thr Ile Pro
            835                 840                 845

Val Met Leu Thr Arg Ala Asp Gly Ser Lys Glu Thr Val Pro Cys Arg
    850                 855                 860

Cys Arg Ile Asp Thr Ala Thr Glu Leu Thr Tyr Tyr Gln Asn Asp Gly
865                 870                 875                 880

Ile Leu His Tyr Val Ile Arg Asn Met Leu Asn
                885                 890

<210> SEQ ID NO 29
<211> LENGTH: 2598
<212> TYPE: DNA
<213> ORGANISM: Escherichia coli

<400> SEQUENCE: 29
```

| | | | | | |
|---|---|---|---|---|---|
| gtgctagaag | aataccgtaa | gcacgtagct | gagcgtgccg | ctgagggat | tgcgcccaaa | 60 |
| cccctggatg | caaaccaaat | ggccgcactt | gtagagctgc | tgaaaaaccc | gcccgcgggc | 120 |
| gaagaagaat | tcctgttaga | tctgttaacc | aaccgtgttc | ccccaggcgt | cgatgaagcc | 180 |
| gcctatgtca | aagcaggctt | cctggctgct | atcgcgaaag | gcgaagccaa | atcccctctg | 240 |
| ctgactccgg | aaaaagccat | cgaactgctg | gcaccatgc | agggtggtta | caacattcat | 300 |
| ccgctgatcg | acgcgctgga | tgatgccaaa | ctggcaccta | ttgctgccaa | agcactttct | 360 |
| cacacgctgc | tgatgttcga | taacttctat | gactagaaag | agaaagcgaa | agcaggcaac | 420 |
| gaatatgcga | agcaggttat | gcagtcctgg | gcggatgccg | aatggttcct | gaatcgcccg | 480 |
| gcgctggctg | aaaaactgac | cgttactgtc | ttcaaagtca | ctggcgaaac | taacaccgat | 540 |
| gacctttctc | cggcaccgga | tgcgtggtca | cgcccggata | tcccactgca | cgcgctggcg | 600 |
| atgctgaaaa | acgcccgtga | aggtattgag | ccagaccagc | ctggtgttgt | tggtccgatc | 660 |
| aagcaaatcg | aagctctgca | acagaaaggt | ttcccgctgg | cgtacgtcgg | tgacgttgtg | 720 |
| ggtacgggtt | cttcgcgtaa | atccgccact | aactccgttc | tgtggtttat | gggcgatgat | 780 |
| attccacatg | tgccgaacaa | acgcggcggt | ggtttgtgcc | tcggcggtaa | aattgcaccc | 840 |
| atcttcttta | acacgatgga | agacgcgggt | gcactgccaa | tcgaagtcga | cgtctctaac | 900 |
| ctgaacatgg | gcgacgtgat | tgacgtttac | ccgtacaaag | gtgaagtgcg | taaccacgaa | 960 |
| accggcgaac | tgctggcgac | cttcgaactg | aaaaccgacg | tgctgattga | tgaagtgcgt | 1020 |
| gctggtggcc | gtattccgct | gattatcggg | cgtggcctga | ccaccaaagc | gcgtgaagca | 1080 |
| cttggtctgc | cgcacagtga | tgtgttccgt | caggcgaaag | atgtcgctga | gagcgatcgc | 1140 |
| ggcttctcgc | tggcgcaaaa | aatggtaggc | cgtgcctgtg | gcgtgaaagg | cattcgtccg | 1200 |
| ggcgcgtact | gtgaaccgaa | aatgacttct | gtaggttccc | aggacaccac | cggcccgatg | 1260 |
| acccgtgatg | aactgaaaga | cctggcgtgc | ctgggcttct | cggctgacct | ggtgatgcag | 1320 |
| tctttctgcc | acaccgcggc | gtatccgaag | ccagttgacg | tgaacacgca | ccacgctctg | 1380 |
| ccggacttca | ttatgaaccg | tggcggtgtg | tcgctgcgtc | cgggtgacgg | cgtcattcac | 1440 |
| tcctggctga | accgtatgct | gctgccggat | accgtcggta | ccggtggtga | ctcccatacc | 1500 |
| cgtttcccga | tcggtatctc | ttttccggcg | gttctggtc | tggtggcgtt | tgctgccgca | 1560 |
| actggcgtaa | tgccgcttga | tatgccggaa | tccgttctgg | tgcgcttcaa | aggcaaaatg | 1620 |
| cagccgggca | tcaccctgcg | cgatctggta | cacgctattc | cgctgtatgc | gatcaaacaa | 1680 |
| ggtctgctga | ccgttgagaa | gaaaggcaag | aaaaacatct | ctctggccg | catcctggaa | 1740 |
| attgaaggtc | tgccggatct | gaaagttgag | caggcctttg | agctaaccga | tgcgtccgcc | 1800 |

-continued

```
gagcgttctg ccgctggttg taccatcaag ctgaacaaag aaccgatcat cgaatacctg    1860
aactctaaca tcgtcctgct gaagtggatg atcgcggaag gttacggcga tcgtcgtacc    1920
ctggaacgtc gtattcaggg catggaaaaa tggctggcga atcctgagct gctggaagcc    1980
gatgcagatg cggaatacgc ggcagtgatc gacatcgatc tggcggatat taaagagcca    2040
atcctgtgtg ctccgaacga cccggatgac gcgcgtccgc tgtctgcggt acagggtgag    2100
aagatcgacg aagtgtttat cggttcctgc atgaccaaca tcggtcactt ccgtgctgcg    2160
ggtaaactgc tggatgcgca taaaggtcag ttgccgaccc gcctgtgggt ggcaccgcca    2220
acccgtatgg acgccgcaca gttgaccgaa gaaggctact acagcgtctt cggtaagagt    2280
ggtgcgcgta tcgagatccc tggctgttcc ctgtgtatgg gtaaccaggc gcgtgtggcg    2340
gacggtgcaa cggtggtttc cacctctacc cgtaacttcc cgaaccgtct gggtactggc    2400
gcgaatgtct tcctggcttc tgcggaactg gcggctgttg cggcgctgat ggcaaactg    2460 ccgacgccgg aagagtacca gacctacgtg gcgcaggtag ataaaacagc cgttgatact    2520
taccgttatc tgaacttcaa ccagctttct cagtacaccg agaaagccga tggggtgatt    2580
ttccagactg cggtttaa                                                 2598
```

<210> SEQ ID NO 30
<211> LENGTH: 865
<212> TYPE: PRT
<213> ORGANISM: Escherichia coli

<400> SEQUENCE: 30

```
Met Leu Glu Glu Tyr Arg Lys His Val Ala Glu Arg Ala Ala Glu Gly
1               5                   10                  15

Ile Ala Pro Lys Pro Leu Asp Ala Asn Gln Met Ala Ala Leu Val Glu
            20                  25                  30

Leu Leu Lys Asn Pro Pro Ala Gly Glu Glu Glu Phe Leu Leu Asp Leu
        35                  40                  45

Leu Thr Asn Arg Val Pro Pro Gly Val Asp Glu Ala Ala Tyr Val Lys
    50                  55                  60

Ala Gly Phe Leu Ala Ile Ala Lys Gly Glu Ala Lys Ser Pro Leu
65                  70                  75                  80

Leu Thr Pro Glu Lys Ala Ile Glu Leu Leu Gly Thr Met Gln Gly Gly
                85                  90                  95

Tyr Asn Ile His Pro Leu Ile Asp Ala Leu Asp Ala Lys Leu Ala
            100                 105                 110

Pro Ile Ala Ala Lys Ala Leu Ser His Thr Leu Leu Met Phe Asp Asn
        115                 120                 125

Phe Tyr Asp Val Glu Glu Lys Ala Lys Ala Gly Asn Glu Tyr Ala Lys
    130                 135                 140

Gln Val Met Gln Ser Trp Ala Asp Ala Glu Trp Phe Leu Asn Arg Pro
145                 150                 155                 160

Ala Leu Ala Glu Lys Leu Thr Val Thr Val Phe Lys Val Thr Gly Glu
                165                 170                 175

Thr Asn Thr Asp Asp Leu Ser Pro Ala Pro Asp Ala Trp Ser Arg Pro
            180                 185                 190

Asp Ile Pro Leu His Ala Leu Ala Met Leu Lys Asn Ala Arg Glu Gly
        195                 200                 205

Ile Glu Pro Asp Gln Pro Gly Val Val Gly Pro Ile Lys Gln Ile Glu
    210                 215                 220
```

-continued

```
Ala Leu Gln Gln Lys Gly Phe Pro Leu Ala Tyr Val Gly Asp Val Val
225                 230                 235                 240

Gly Thr Gly Ser Ser Arg Lys Ser Ala Thr Asn Ser Val Leu Trp Phe
            245                 250                 255

Met Gly Asp Asp Ile Pro His Val Pro Asn Lys Arg Gly Gly Gly Leu
        260                 265                 270

Cys Leu Gly Gly Lys Ile Ala Pro Ile Phe Phe Asn Thr Met Glu Asp
    275                 280                 285

Ala Gly Ala Leu Pro Ile Glu Val Asp Val Ser Asn Leu Asn Met Gly
290                 295                 300

Asp Val Ile Asp Val Tyr Pro Tyr Lys Gly Glu Val Arg Asn His Glu
305                 310                 315                 320

Thr Gly Glu Leu Leu Ala Thr Phe Glu Leu Lys Thr Asp Val Leu Ile
            325                 330                 335

Asp Glu Val Arg Ala Gly Gly Arg Ile Pro Leu Ile Gly Arg Gly
        340                 345                 350

Leu Thr Thr Lys Ala Arg Glu Ala Leu Gly Leu Pro His Ser Asp Val
            355                 360                 365

Phe Arg Gln Ala Lys Asp Val Ala Glu Ser Asp Arg Gly Phe Ser Leu
    370                 375                 380

Ala Gln Lys Met Val Gly Arg Ala Cys Gly Val Lys Gly Ile Arg Pro
385                 390                 395                 400

Gly Ala Tyr Cys Glu Pro Lys Met Thr Ser Val Gly Ser Gln Asp Thr
                405                 410                 415

Thr Gly Pro Met Thr Arg Asp Glu Leu Lys Asp Leu Ala Cys Leu Gly
            420                 425                 430

Phe Ser Ala Asp Leu Val Met Gln Ser Phe Cys His Thr Ala Ala Tyr
    435                 440                 445

Pro Lys Pro Val Asp Val Asn Thr His His Thr Leu Pro Asp Phe Ile
450                 455                 460

Met Asn Arg Gly Gly Val Ser Leu Arg Pro Gly Asp Gly Val Ile His
465                 470                 475                 480

Ser Trp Leu Asn Arg Met Leu Leu Pro Asp Thr Val Gly Thr Gly Gly
            485                 490                 495

Asp Ser His Thr Arg Phe Pro Ile Gly Ile Ser Phe Pro Ala Gly Ser
        500                 505                 510

Gly Leu Val Ala Phe Ala Ala Thr Gly Val Met Pro Leu Asp Met
    515                 520                 525

Pro Glu Ser Val Leu Val Arg Phe Lys Gly Lys Met Gln Pro Gly Ile
530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Lys Asn Ile Phe Ser Gly
            565                 570                 575

Arg Ile Leu Glu Ile Glu Gly Leu Pro Asp Leu Lys Val Glu Gln Ala
        580                 585                 590

Phe Glu Leu Thr Asp Ala Ser Ala Glu Arg Ser Ala Ala Gly Cys Thr
    595                 600                 605

Ile Lys Leu Asn Lys Glu Pro Ile Ile Glu Tyr Leu Asn Ser Asn Ile
    610                 615                 620

Val Leu Leu Lys Trp Met Ile Ala Glu Gly Tyr Gly Asp Arg Arg Thr
625                 630                 635                 640
```

```
Leu Glu Arg Arg Ile Gln Gly Met Glu Lys Trp Leu Ala Asn Pro Glu
            645                 650                 655

Leu Leu Glu Ala Asp Ala Asp Ala Glu Tyr Ala Ala Val Ile Asp Ile
    660                 665                 670

Asp Leu Ala Asp Ile Lys Glu Pro Ile Leu Cys Ala Pro Asn Asp Pro
        675                 680                 685

Asp Asp Ala Arg Pro Leu Ser Ala Val Gln Gly Lys Ile Asp Glu
    690                 695                 700

Val Phe Ile Gly Ser Cys Met Thr Asn Ile Gly His Phe Arg Ala Ala
705                 710                 715                 720

Gly Lys Leu Leu Asp Ala His Lys Gly Gln Leu Pro Thr Arg Leu Trp
                725                 730                 735

Val Ala Pro Pro Thr Arg Met Asp Ala Ala Gln Leu Thr Glu Glu Gly
            740                 745                 750

Tyr Tyr Ser Val Phe Gly Lys Ser Gly Ala Arg Ile Glu Ile Pro Gly
        755                 760                 765

Cys Ser Leu Cys Met Gly Asn Gln Ala Arg Val Ala Asp Gly Ala Thr
770                 775                 780

Val Val Ser Thr Ser Thr Arg Asn Phe Pro Asn Arg Leu Gly Thr Gly
785                 790                 795                 800

Ala Asn Val Phe Leu Ala Ser Ala Glu Leu Ala Ala Val Ala Ala Leu
                805                 810                 815

Ile Gly Lys Leu Pro Thr Pro Glu Glu Tyr Gln Thr Tyr Val Ala Gln
            820                 825                 830

Val Asp Lys Thr Ala Val Asp Thr Tyr Arg Tyr Leu Asn Phe Asn Gln
        835                 840                 845

Leu Ser Gln Tyr Thr Glu Lys Ala Asp Gly Val Ile Phe Gln Thr Ala
    850                 855                 860

Val
865

<210> SEQ ID NO 31
<211> LENGTH: 2697
<212> TYPE: DNA
<213> ORGANISM: Pantoea ananatis

<400> SEQUENCE: 31
atgctgcccc acgcggaacc gggcaccttg ccctactcat ggaatgcgtt gtcatcaggg      60
tgcaccggaa acccatacaa tgagagcgag gagaacgtcg tgctagaaga ataccgtaag     120
cacgttgccg agcgtgctgc ccaagggatc gtacctaagc cattagatgc ttcccaaatg     180
gccgcgctgg ttgaactgct aaaaaatcca cctgcgggtg aagaagaatt tttgaccgat     240 tgttggtca accgcgtacc acccggcgtc gatgaagcgg cgtatgttaa agcaggtttc     300
ctggctgctg tcgccaaagg cgaaacaacc tctcctctgg tatctcctga aaaagctgtt     360
gaactgctcg gtaccatgca gggcggctac aacatccatc ctctgattga agcattagat     420
gatgcgaaac tcgcaccgat tgcggcaaaa gcgctttccc acacgttgct gatgtttgac     480
agcttttacg acgttgaaga aaaagccaaa gcaggcaatc cacacgcgaa gcaggtgatg     540
cagtcgtggg cggatgccga atggtatctg tcacgtcctg agctggctga aaaaattacc     600
gttacggttt tcaaagtcac gggtgaaacc aacaccgatg acctgtctcc ggcaccggat     660
gcctggtcac gtccggatat cccactgcat gccctggcga tgctgaaaaa tgcccgtgaa     720
ggcattgagc cgaatgaggc aggcaacatc ggtccgatta gcagatcga agcactgcag     780
```

```
gccaaaggtt tcccgctggc ctatgtgggc gacgttgtgg gcacaggttc atcccgtaaa    840
tcggccacca actcggtgct gtggtttatg ggcgatgaca tccctaacgt gccgaataag    900
aaaggcggtg gtgttgttct gggcggcaag attgcgccta tcttcttcaa caccatggaa    960
gatgccggcg cgctgccgat cgaagtggat gtgaacgacc tgaatatggg tgatgtcatt   1020
gatatctatc ctttaaagg cgaagtgcgc aatcacgaaa ccggcgatct gctggccagt   1080
tttgaactga aaccgacgt gctgattgat gaagtgcgtg ccggtggccg tattccactg   1140
atcatcggtc gtggcctgac cagcaaagcg cgtgaatccc tggggctgcc tgtcagcacc   1200
gtgttccgta tcgcgaaaga cgtggcgaaa agctcacgcg gctactcact ggcgcagaaa   1260
atggttggcc gcgcctgtgg cgtggacggc gtccgtccgg gtgcctattg cgaaccgaaa   1320
atgacctcgg tgggctcgca ggataccacc ggtcctatga cccgcgacga gctgaaagac   1380
ctggcatgtc tgggcttctc tgccgatctg gtgatgcagt cgttctgtca cacggcggct   1440
tatcctaagc cagtcgatgt gaacacgcac cacacgctgc cagacttcat catgaaccgt   1500
ggcggcgttt ccctgcgtcc ggggatggc gtgattcact cctggctgaa ccgtatgctg   1560
ctgccggata ccgtcggcac cggtggcgat tcccacaccc gcttcccaat cggtatttcc   1620
ttcccggcag gttcgggtct ggttgccttt gcggcagcga ccggcgttat gccactggat   1680
atgccggaat cggtactggt acgtttcaaa ggtaaaatgc agcccggcat tacgctgcgc   1740
gatctggttc acgccattcc gctgtatgcg attaagcagg gcctgttaac cgttgagaag   1800
aaaggtaaga gaacatctct ctccggtcgc atccttgaaa ttgaaggtct gcccgatctg   1860 aaagtgggagc aggcgttcga actgaccgat gcctctgctg agcgttctgc tgcaggctgt   1920
accatcaagc tggatcaggc gccgatcaaa gagtatctga catctaacat tgtcctgctg   1980
aaatggatga tctcagaagg ctacggcgat cgtcgtacgc ttgagcgccg tatcgaaggc   2040
atggagaaat ggctggcaga tccacagctg ctcgaagccg acgccgatgc agaatatgct   2100
gcggtgattg acatcgatct ggcggagatc aaagagccga ttctgtgcgc gccaaacgat   2160
cccgacgatg cgcgtctgct gtcagatgtg cagggcgaga agattgatga agtctttatc   2220
ggttcgtgca tgaccaacat cggtcacttc gcgcggcag taagttgct ggacagccac   2280 aaaggccaac tgccaacccg tttatgggtc gcaccaccga ccaaaatgga tgcggcacag   2340
ctgacggaag aaggctacta cagcgtgttc ggtaagagcg gtgcgcgtat tgagatcccg   2400
ggttgttcac tgtgcatggg taaccaggca cgtgtcgccg atggcgcaac ggtcgtttcg   2460
acctcaaccc gtaacttccc gaaccgtttg ggtacagggg ctaacgtcta cctggcttct   2520
gcggagctgg cggcggtctc atcactgtta ggtaagctgc caacgccaga tgagtatcag   2580
cagtttatgg cgcaggtgga taaaacggct agcgatacct atcgctatct caactttgac   2640
cagttgagcc agtacactga aaaagcggat ggcgtgattt tccagaccgc cgtctga     2697
```

<210> SEQ ID NO 32
<211> LENGTH: 898
<212> TYPE: PRT
<213> ORGANISM: Pantoea ananatis

<400> SEQUENCE: 32

Met Leu Pro His Ala Glu Pro Gly Thr Leu Pro Tyr Ser Trp Asn Ala
1               5                   10                  15

Leu Ser Ser Gly Cys Thr Gly Asn Pro Tyr Asn Glu Ser Glu Glu Asn
            20                  25                  30

Val Val Leu Glu Glu Tyr Arg Lys His Val Ala Glu Arg Ala Ala Gln
            35                  40                  45

Gly Ile Val Pro Lys Pro Leu Asp Ala Ser Gln Met Ala Ala Leu Val
 50                  55                  60

Glu Leu Leu Lys Asn Pro Pro Ala Gly Glu Glu Phe Leu Thr Asp
 65                  70                  75                  80

Leu Leu Val Asn Arg Val Pro Pro Gly Val Asp Glu Ala Ala Tyr Val
                 85                  90                  95

Lys Ala Gly Phe Leu Ala Ala Val Ala Lys Gly Glu Thr Thr Ser Pro
                100                 105                 110

Leu Val Ser Pro Glu Lys Ala Val Glu Leu Leu Gly Thr Met Gln Gly
                115                 120                 125

Gly Tyr Asn Ile His Pro Leu Ile Glu Ala Leu Asp Asp Ala Lys Leu
            130                 135                 140

Ala Pro Ile Ala Ala Lys Ala Leu Ser His Thr Leu Leu Met Phe Asp
145                 150                 155                 160

Ser Phe Tyr Asp Val Glu Glu Lys Ala Lys Ala Gly Asn Pro His Ala
                165                 170                 175

Lys Gln Val Met Gln Ser Trp Ala Asp Ala Glu Trp Tyr Leu Ser Arg
                180                 185                 190

Pro Glu Leu Ala Glu Lys Ile Thr Val Thr Val Phe Lys Val Thr Gly
                195                 200                 205

Glu Thr Asn Thr Asp Asp Leu Ser Pro Ala Pro Asp Ala Trp Ser Arg
            210                 215                 220

Pro Asp Ile Pro Leu His Ala Leu Ala Met Leu Lys Asn Ala Arg Glu
225                 230                 235                 240

Gly Ile Glu Pro Asn Glu Ala Gly Asn Ile Gly Pro Ile Lys Gln Ile
                245                 250                 255

Glu Ala Leu Gln Ala Lys Gly Phe Pro Leu Ala Tyr Val Gly Asp Val
                260                 265                 270

Val Gly Thr Gly Ser Ser Arg Lys Ser Ala Thr Asn Ser Val Leu Trp
            275                 280                 285

Phe Met Gly Asp Asp Ile Pro Asn Val Pro Asn Lys Lys Gly Gly Gly
290                 295                 300

Val Val Leu Gly Gly Lys Ile Ala Pro Ile Phe Phe Asn Thr Met Glu
305                 310                 315                 320

Asp Ala Gly Ala Leu Pro Ile Glu Val Asp Val Asn Asp Leu Asn Met
                325                 330                 335

Gly Asp Val Ile Asp Ile Tyr Pro Phe Lys Gly Glu Val Arg Asn His
            340                 345                 350

Glu Thr Gly Asp Leu Leu Ala Ser Phe Glu Leu Lys Thr Asp Val Leu
            355                 360                 365

Ile Asp Glu Val Arg Ala Gly Gly Arg Ile Pro Leu Ile Ile Gly Arg
            370                 375                 380

Gly Leu Thr Ser Lys Ala Arg Glu Ser Leu Gly Leu Pro Val Ser Thr
385                 390                 395                 400

Val Phe Arg Ile Ala Lys Asp Val Ala Glu Ser Ser Arg Gly Tyr Ser
                405                 410                 415

Leu Ala Gln Lys Met Val Gly Arg Ala Cys Gly Val Asp Gly Val Arg
                420                 425                 430

Pro Gly Ala Tyr Cys Glu Pro Lys Met Thr Ser Val Gly Ser Gln Asp
            435                 440                 445

```
Thr Thr Gly Pro Met Thr Arg Asp Glu Leu Lys Asp Leu Ala Cys Leu
    450                 455                 460
Gly Phe Ser Ala Asp Leu Val Met Gln Ser Phe Cys His Thr Ala Ala
465                 470                 475                 480
Tyr Pro Lys Pro Val Asp Val Asn Thr His His Thr Leu Pro Asp Phe
                485                 490                 495
Ile Met Asn Arg Gly Val Ser Leu Arg Pro Gly Asp Gly Val Ile
                500                 505                 510
His Ser Trp Leu Asn Arg Met Leu Leu Pro Asp Thr Val Gly Thr Gly
            515                 520                 525
Gly Asp Ser His Thr Arg Phe Pro Ile Gly Ile Ser Phe Pro Ala Gly
530                 535                 540
Ser Gly Leu Val Ala Phe Ala Ala Thr Gly Val Met Pro Leu Asp
545                 550                 555                 560
Met Pro Glu Ser Val Leu Val Arg Phe Lys Gly Lys Met Gln Pro Gly
                565                 570                 575
Ile Thr Leu Arg Asp Leu Val His Ala Ile Pro Leu Tyr Ala Ile Lys
                580                 585                 590
Gln Gly Leu Leu Thr Val Glu Lys Lys Gly Lys Lys Asn Ile Phe Ser
        595                 600                 605
Gly Arg Ile Leu Glu Ile Glu Gly Leu Pro Asp Leu Lys Val Glu Gln
        610                 615                 620
Ala Phe Glu Leu Thr Asp Ala Ser Ala Glu Arg Ser Ala Ala Gly Cys
625                 630                 635                 640
Thr Ile Lys Leu Asp Gln Ala Pro Ile Lys Glu Tyr Leu Thr Ser Asn
                645                 650                 655
Ile Val Leu Leu Lys Trp Met Ile Ser Glu Gly Tyr Gly Asp Arg Arg
                660                 665                 670
Thr Leu Glu Arg Arg Ile Glu Gly Met Glu Lys Trp Leu Ala Asp Pro
            675                 680                 685
Gln Leu Leu Glu Ala Asp Ala Asp Ala Glu Tyr Ala Ala Val Ile Asp
        690                 695                 700
Ile Asp Leu Ala Glu Ile Lys Glu Pro Ile Leu Cys Ala Pro Asn Asp
705                 710                 715                 720
Pro Asp Asp Ala Arg Leu Leu Ser Asp Val Gln Gly Glu Lys Ile Asp
                725                 730                 735
Glu Val Phe Ile Gly Ser Cys Met Thr Asn Ile Gly His Phe Arg Ala
                740                 745                 750
Ala Gly Lys Leu Leu Asp Ser His Lys Gly Gln Leu Pro Thr Arg Leu
            755                 760                 765
Trp Val Ala Pro Pro Thr Lys Met Asp Ala Ala Gln Leu Thr Glu Glu
        770                 775                 780
Gly Tyr Tyr Ser Val Phe Gly Lys Ser Gly Ala Arg Ile Glu Ile Pro
785                 790                 795                 800
Gly Cys Ser Leu Cys Met Gly Asn Gln Ala Arg Val Ala Asp Gly Ala
                805                 810                 815
Thr Val Val Ser Thr Ser Thr Arg Asn Phe Pro Asn Arg Leu Gly Thr
                820                 825                 830
Gly Ala Asn Val Tyr Leu Ala Ser Ala Glu Leu Ala Ala Val Ser Ser
            835                 840                 845
Leu Leu Gly Lys Leu Pro Thr Pro Asp Glu Tyr Gln Gln Phe Met Ala
850                 855                 860
```

Gln Val Asp Lys Thr Ala Ser Asp Thr Tyr Arg Tyr Leu Asn Phe Asp
865                 870                 875                 880

Gln Leu Ser Gln Tyr Thr Glu Lys Ala Asp Gly Val Ile Phe Gln Thr
                885                 890                 895

Ala Val

<210> SEQ ID NO 33
<211> LENGTH: 2598
<212> TYPE: DNA
<213> ORGANISM: Pectobacterium atrosepticum

<400> SEQUENCE: 33

| | | | | |
|---|---|---|---|---|
| gtgctagaag | aatatcgtaa | gcacgtagcc | gagcgggctg | cgcaggggat | tgttcctaaa | 60 |
| ccgttagatg | ccacgcagat | ggccgcgctg | gttgagtcac | tcaagaatcc | cccggcaggc | 120 |
| gaagaggaag | tattgcttga | tctgctgatt | aaccgcgttc | cacccggtgt | tgatgaagcc | 180 |
| gcctacgtga | aggccggttt | tttggctgct | gtcgctaaag | gcgaagccac | ttcccccttg | 240 |
| gttacccagg | aaaaagcgat | tgagctgctg | ggcaccatgc | aaggtggtta | taatattcat | 300 |
| ccgctaattg | atgcattaga | cagcgacacg | ctggcaccga | ttgccgcgaa | agcgttgtcc | 360 |
| cagacgctgc | tgatgtttga | taacttctat | gatgtggaag | aaaaagcgaa | agcaggcaat | 420 |
| gcacacgcca | agaaagtgat | tcaatcctgg | gctgatgccg | agtggttcct | gtcccgcccg | 480 |
| aaactggcgg | aaaaaattac | cgttaccgtc | tttaaagtca | ctggtgaaac | taacactgat | 540 |
| gacctgtctc | cggcacctga | tgcctggtcg | cgccctgata | tcccgctgca | cgcgttggcg | 600 |
| atgctgaaaa | atgcccgtga | aggcattgat | cccgatcagc | ctggcaacgt | gggtccgatc | 660 |
| aaacagatcg | aagaactgaa | caagaaaggc | ttcccgctgg | cgtacgtcgg | tgacgtcgtt | 720 |
| ggtacgggat | cgtcgcgtaa | atctgcaacc | aactccgtgc | tgtggttcat | gggtgaagac | 780 |
| attcctcatg | ttccgaacaa | cgcggcggt | ggtgtggtgc | tgggcggcaa | gattgcccca | 840 |
| atcttcttca | acaccatgga | agatgccggt | gcgttgccga | tcgaagtcga | tgttaacgat | 900 |
| ctgaatatgg | gcgatgtgat | cgacatctac | ccgtatgaag | gtgaagttcg | ccgtcatgac | 960 |
| acgaatgaag | tgctggcgac | gtttgcgctg | aagaccgacg | tattactgga | tgaagtgcgc | 1020 |
| gccggtggcc | gtattccgtt | gatcatcgga | cgtgggttga | cgtctaaagc | gcgtgagtca | 1080 |
| ctggacttgc | cgcacagcga | tgtcttccgt | atttctaaag | ccattgaagc | cagcaaaaaa | 1140 |
| ggcttctcac | tggcgcagaa | aatggtcggt | cgcgcctgcg | gcgtcgcggg | tattcgccct | 1200 |
| gatgaatact | gcgaacctaa | gatgacatcc | gtgggttcac | aggacaccac | cgggccgatg | 1260 |
| actcgtgatg | agctgaaaga | tctggcttgt | ctcggcttct | ccgctgactt | ggtgatgcag | 1320 |
| tcgttctgtc | acactgcggc | ctatcctaag | ccggttgacg | tgaccacgca | ccacacgctg | 1380 |
| cctgatttca | tcatgaaccg | tggcggcgta | tcgctacgtc | cgggcgatgg | cgttatccac | 1440 |
| tcctggctga | accgtatgct | gctgccggat | accgttggta | caggcggtga | ctcccacacc | 1500 |
| cgtttcccaa | tcggtatctc | tttccctgca | ggttctgggc | tggtgcgtt | tgctgcggct | 1560 |
| acgggcgtga | tgccgctgga | tatgccggaa | tctattctgg | tgcgcttcaa | aggcaaaatg | 1620 |
| cagccgggta | ttactctgcg | cgatctggtt | cacgccattc | cgctgtatgc | catcaaacaa | 1680 |
| ggtctgctga | ccgttgagaa | gaaaggtaag | aagaacatct | ctctggtcg | tattctggaa | 1740 |
| atcgaaggcc | tgccggatct | gaaagtcgag | caggcgtttg | aactgaccga | cgcctcggcg | 1800 |
| gaacgttctg | cggctggttg | tacgatcaag | ctggataaag | cgccgatcat | cgagtatttg | 1860 |
| aactccaaca | tcgttctgct | gaagtggatg | atctccgaag | gttatggcga | tcgccgtacg | 1920 |

-continued

```
ctggaacgtc gtgttcaagg tatggaaaaa tggctggccg atccgcaact gctggaagcc      1980
gatgccgatg ccgagtatgc ggcggtgatc gacatcgatc tggctgacat caaagagccg      2040
atcctgtgtg cgccgaacga tccagacgat gcgcgctggc tgtctgacgt gcagggcgag      2100
aagattgatg aagtcttcat cggttcctgt atgaccaaca tcggacactt ccgtgcggcg      2160
ggtaaactgc tggatagcca caaggccag ctgccgaccc gtttgtgggt tgcgccgccg       2220
accaaaatgg acgcggcaca gctgacggaa gaaggctatt acagcgtgtt tggtaagagc      2280
ggagcgcgta tcgagatccc aggttgctcg ctgtgcatgg gtaatcaggc gcgcgtggcg      2340
gatggcgcga cggtcgtttc tacgtcgacc cgtaacttcc cgaaccgttt gggaaccggt      2400
gctaacgtgt atcttgcgtc tgctgaactg gctgcggttg cctcgctgtt gggccgtttg      2460
ccgacgcctg aagagtacca gacctacatg tcgcaggtgg ataaaaccgc gcaggacacc      2520
tatcgctatc tgaattttga ccagttaggt caatatactg agaaagccga tggcgtgatc      2580
ttccagacga ctgtctaa                                                    2598
```

<210> SEQ ID NO 34
<211> LENGTH: 865
<212> TYPE: PRT
<213> ORGANISM: Pectobacterium atrosepticum

<400> SEQUENCE: 34

```
Met Leu Glu Glu Tyr Arg Lys His Val Ala Glu Arg Ala Ala Gln Gly
1               5                   10                  15

Ile Val Pro Lys Pro Leu Asp Ala Thr Gln Met Ala Ala Leu Val Glu
            20                  25                  30

Ser Leu Lys Asn Pro Pro Ala Gly Glu Glu Val Leu Leu Asp Leu
        35                  40                  45

Leu Ile Asn Arg Val Pro Pro Gly Val Asp Glu Ala Ala Tyr Val Lys
    50                  55                  60

Ala Gly Phe Leu Ala Ala Val Ala Lys Gly Glu Ala Thr Ser Pro Leu
65                  70                  75                  80

Val Thr Gln Glu Lys Ala Ile Glu Leu Leu Gly Thr Met Gln Gly Gly
                85                  90                  95

Tyr Asn Ile His Pro Leu Ile Asp Ala Leu Asp Ser Asp Thr Leu Ala
            100                 105                 110

Pro Ile Ala Ala Lys Ala Leu Ser Gln Thr Leu Leu Met Phe Asp Asn
        115                 120                 125

Phe Tyr Asp Val Glu Glu Lys Ala Lys Ala Gly Asn Ala His Ala Lys
    130                 135                 140

Lys Val Ile Gln Ser Trp Ala Asp Ala Glu Trp Phe Leu Ser Arg Pro
145                 150                 155                 160

Lys Leu Ala Glu Lys Ile Thr Val Thr Val Phe Lys Val Thr Gly Glu
                165                 170                 175

Thr Asn Thr Asp Asp Leu Ser Pro Ala Pro Asp Ala Trp Ser Arg Pro
            180                 185                 190

Asp Ile Pro Leu His Ala Leu Ala Met Leu Lys Asn Ala Arg Glu Gly
        195                 200                 205

Ile Asp Pro Asp Gln Pro Gly Asn Val Gly Pro Ile Lys Gln Ile Glu
    210                 215                 220

Glu Leu Asn Lys Lys Gly Phe Pro Leu Ala Tyr Val Gly Asp Val Val
225                 230                 235                 240

Gly Thr Gly Ser Ser Arg Lys Ser Ala Thr Asn Ser Val Leu Trp Phe
                245                 250                 255
```

```
Met Gly Glu Asp Ile Pro His Val Pro Asn Lys Arg Gly Gly Val
            260                 265                 270

Val Leu Gly Gly Lys Ile Ala Pro Ile Phe Phe Asn Thr Met Glu Asp
        275                 280                 285

Ala Gly Ala Leu Pro Ile Glu Val Asp Val Asn Asp Leu Asn Met Gly
    290                 295                 300

Asp Val Ile Asp Ile Tyr Pro Tyr Glu Gly Glu Val Arg Arg His Asp
305                 310                 315                 320

Thr Asn Glu Val Leu Ala Thr Phe Ala Leu Lys Thr Asp Val Leu Leu
                325                 330                 335

Asp Glu Val Arg Ala Gly Gly Arg Ile Pro Leu Ile Ile Gly Arg Gly
            340                 345                 350

Leu Thr Ser Lys Ala Arg Glu Ser Leu Asp Leu Pro His Ser Asp Val
        355                 360                 365

Phe Arg Ile Ser Lys Ala Ile Glu Ala Ser Lys Lys Gly Phe Ser Leu
    370                 375                 380

Ala Gln Lys Met Val Gly Arg Ala Cys Gly Val Ala Gly Ile Arg Pro
385                 390                 395                 400

Asp Glu Tyr Cys Glu Pro Lys Met Thr Ser Val Gly Ser Gln Asp Thr
                405                 410                 415

Thr Gly Pro Met Thr Arg Asp Glu Leu Lys Asp Leu Ala Cys Leu Gly
            420                 425                 430

Phe Ser Ala Asp Leu Val Met Gln Ser Phe Cys His Thr Ala Ala Tyr
    435                 440                 445

Pro Lys Pro Val Asp Val Thr Thr His His Thr Leu Pro Asp Phe Ile
450                 455                 460

Met Asn Arg Gly Gly Val Ser Leu Arg Pro Gly Asp Gly Val Ile His
465                 470                 475                 480

Ser Trp Leu Asn Arg Met Leu Leu Pro Asp Thr Val Gly Thr Gly Gly
                485                 490                 495

Asp Ser His Thr Arg Phe Pro Ile Gly Ile Ser Phe Pro Ala Gly Ser
            500                 505                 510

Gly Leu Val Ala Phe Ala Ala Ala Thr Gly Val Met Pro Leu Asp Met
        515                 520                 525

Pro Glu Ser Ile Leu Val Arg Phe Lys Gly Lys Met Gln Pro Gly Ile
    530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Lys Asn Ile Phe Ser Gly
                565                 570                 575

Arg Ile Leu Glu Ile Glu Gly Leu Pro Asp Leu Lys Val Glu Gln Ala
            580                 585                 590

Phe Glu Leu Thr Asp Ala Ser Ala Glu Arg Ser Ala Ala Gly Cys Thr
        595                 600                 605

Ile Lys Leu Asp Lys Ala Pro Ile Ile Glu Tyr Leu Asn Ser Asn Ile
    610                 615                 620

Val Leu Leu Lys Trp Met Ile Ser Glu Gly Tyr Gly Asp Arg Arg Thr
625                 630                 635                 640

Leu Glu Arg Arg Val Gln Gly Met Glu Lys Trp Leu Ala Asp Pro Gln
                645                 650                 655

Leu Leu Glu Ala Asp Ala Asp Ala Glu Tyr Ala Ala Val Ile Asp Ile
            660                 665                 670
```

```
          Asp Leu Ala Asp Ile Lys Glu Pro Ile Leu Cys Ala Pro Asn Asp Pro
                  675                 680                 685

Asp Asp Ala Arg Trp Leu Ser Asp Val Gln Gly Glu Lys Ile Asp Glu
          690                 695                 700

Val Phe Ile Gly Ser Cys Met Thr Asn Ile Gly His Phe Arg Ala Ala
          705                 710                 715                 720

Gly Lys Leu Leu Asp Ser His Lys Gly Gln Leu Pro Thr Arg Leu Trp
                          725                 730                 735

Val Ala Pro Pro Thr Lys Met Asp Ala Ala Gln Leu Thr Glu Gly
                      740                 745                 750

Tyr Tyr Ser Val Phe Gly Lys Ser Gly Ala Arg Ile Glu Ile Pro Gly
                      755                 760                 765

Cys Ser Leu Cys Met Gly Asn Gln Ala Arg Val Ala Asp Gly Ala Thr
                  770                 775                 780

Val Val Ser Thr Ser Thr Arg Asn Phe Pro Asn Arg Leu Gly Thr Gly
          785                 790                 795                 800

Ala Asn Val Tyr Leu Ala Ser Ala Glu Leu Ala Ala Val Ala Ser Leu
                          805                 810                 815

Leu Gly Arg Leu Pro Thr Pro Glu Glu Tyr Gln Thr Tyr Met Ser Gln
                      820                 825                 830

Val Asp Lys Thr Ala Gln Asp Thr Tyr Arg Tyr Leu Asn Phe Asp Gln
                      835                 840                 845

Leu Gly Gln Tyr Thr Glu Lys Ala Asp Gly Val Ile Phe Gln Thr Thr
                      850                 855                 860

Val
          865

<210> SEQ ID NO 35
<211> LENGTH: 2598
<212> TYPE: DNA
<213> ORGANISM: Salmonella enterica

<400> SEQUENCE: 35
gtgctagaag aataccgtaa gcacgtagct gagcgtgctg cccagggat tgtgccgaaa      60 cctttagacg caacccaaat ggctgcgctt gtcgagctgc tgaagacccc gcctgtgggc    120
gaagaagaat tcctgttaga cctgttgatc aaccgcgttc ctcctggcgt cgatgaagcc    180
gcttatgtta aagccggttt tctcgctgct gtcgcgaaag cgacaccac ctccccgctg     240 gtctccccag aaaaagccat tgaactgctg ggcaccatgc agggtggtta caacattcat    300
ccgctgattg acgcgctgga cgatgcgaaa ctggcgccga ttgcggccaa agcgctgtct    360
cacaccctgc tgatgttcga taacttctac gactagaag agaaagccaa agcgggcaat     420
gaatatgcca acaggtgat gcaatcttgg gccgacgccg aatggttcct gagccgtccg     480
ccgctggcgg aaaaaatcac cgtcaccgtt ttcaaagtga ccggcgaaac gaataccgac    540
gatctctctc cggcgccgga tgcgtggtcg agaccggata tcccgttaca tgcgcaggcg    600
atgctgaaaa acgcccgtga aggcattgag ccggatcagc caggcgttgt cggcccgatc    660
aaacaaatcg aagcattgca gaaaaaaggc tacccgctgg cctacgtggg tgacgtggtg    720
ggcaccggtt cttcccgtaa atccgcgacc aactccgtgc tgtggttcat gggcgatgac    780
atcccgaacg tgccgaacaa gcgcggcggc ggtctgtgcc tcggcggcaa aattgcgcct    840
atcttcttta acaccatgga agatgcgggc gcgctgccga ttgaagttga cgtttctaac    900
ctgaacatgg gcgatgtaat tgacgtctac ccgtacaaag gcgaagtgcg caatcatgaa    960
```

-continued

```
accgatgaac tgctggcaac cttcgaactg aaaaccgacg tgctgatcga cgaagtacgc    1020
gccggtggcc gtattccgct gattatcgga cgtggcctga ccaccaaagc gcgtgaagcg    1080
ctgggtctgc cgcactctga cgttttccgt caggcaaaag acgtggcaga aagcagccgt    1140
ggcttctctc tggcgcagaa aatggtcggt cgcgcctgcg cgtgaaaggc attcgtccg     1200
ggcgcgtact gcgaaccgaa atgacctcc gtcggttctc aggatactac tggcccgatg     1260
accgtgatg agctgaaaga cctggcctgt ctgggattct ccgccgatct ggtcatgcag     1320
tcgttctgtc acaccgcagc ctatccgaag cccgttgacg tcaccacgca ccacgcgctg    1380
ccggacttca ttatgaaccg cggcggtgtc tccctgcgtc cgggcgacgg cgtgatccac    1440
tcctggctga accgtatgct gctgccggac accgtcggta ccggcggtga ctcccatacc    1500
cgtttcccga ttggtatctc tttcccggcg ggttctggtc tggtggcgtt tgccgccgcg    1560
accggcgtga tgccgctgga tatgccggaa tcggtgctgg tgcgcttcaa aggcaaaatg    1620
cagccgggca tcaccctgcg cgatctggtc catgccatcc cgctgtacgc catcaaacag    1680
ggcctgctga ccgttgagaa gaaaggcaag aaaaacatct tctctggccg catcctggaa    1740
atcgaaggtc tgccggatct gaaagtcgag caggcgtttg agctgaccga tgcttctgcc    1800
gagcgttccg ctgccggttg taccatcaag ctgaacaaag agccgatcgt tgaatacctg    1860
acctccaaca tcgtcctgct gaagtggatg atcgccgaag ctacggcga ccgtcgtacg    1920
ctgaacgtc gtatccaggg tatggaaaaa tggctggcgg acccgcagct gctggaagcc     1980
gatgctgacg cggaatacgc agcggtgatc gacatcgatc tggcggatat caaagagcca    2040
atcctctgtg cgccgaacga tccggacgac gcgcgtctgc tgtctgacgt gcagggcgag    2100
aagatcgacg aagtgttcat cggttcctgc atgaccaaca tcggccactt ccgcgcggct    2160
ggtaagctgc tggatagcca caaggccag ttgccaaccc gcctgtgggt agcgccgcca     2220
acccgtatgg acgctgcgca gctgaccgaa gaaggttact acagcgtgtt tggtaagagc    2280
ggtgcgcgta tcgaaatccc gggttgttcc ctgtgtatgg gtaaccaggc gcgtgtggct    2340
gacggcgcga cggtggtttc cacttctacc cgtaacttcc cgaaccgttt aggtactggt    2400
gcgaacgtct tcctggcttc tgcggagctg cggcgcgttg cagcgcttat ggcaaactg     2460
ccgacgccgg aagagtacca gacctttgtg gcgcaggtgg ataagacggc ggtggatacc    2520
taccgttatc tgaacttcga ccagctctct cagtacactg agaaagcgga tggggtgatt    2580
ttccagactg cggtataa                                                  2598
```

<210> SEQ ID NO 36
<211> LENGTH: 865
<212> TYPE: PRT
<213> ORGANISM: Salmonella enterica

<400> SEQUENCE: 36

```
Met Leu Glu Glu Tyr Arg Lys His Val Ala Glu Arg Ala Ala Gln Gly
1               5                   10                  15

Ile Val Pro Lys Pro Leu Asp Ala Thr Gln Met Ala Ala Leu Val Glu
            20                  25                  30

Leu Leu Lys Thr Pro Pro Val Gly Glu Glu Glu Phe Leu Leu Asp Leu
        35                  40                  45

Leu Ile Asn Arg Val Pro Pro Gly Val Asp Glu Ala Ala Tyr Val Lys
    50                  55                  60

Ala Gly Phe Leu Ala Ala Val Ala Lys Gly Asp Thr Thr Ser Pro Leu
65                  70                  75                  80
```

```
Val Ser Pro Glu Lys Ala Ile Glu Leu Leu Gly Thr Met Gln Gly Gly
            85                  90                  95

Tyr Asn Ile His Pro Leu Ile Asp Ala Leu Asp Ala Lys Leu Ala
        100                 105                 110

Pro Ile Ala Ala Lys Ala Leu Ser His Thr Leu Leu Met Phe Asp Asn
            115                 120                 125

Phe Tyr Asp Val Glu Glu Lys Ala Lys Ala Gly Asn Glu Tyr Ala Lys
        130                 135                 140

Gln Val Met Gln Ser Trp Ala Asp Ala Glu Trp Phe Leu Ser Arg Pro
145                 150                 155                 160

Pro Leu Ala Glu Lys Ile Thr Val Thr Val Phe Lys Val Thr Gly Glu
                165                 170                 175

Thr Asn Thr Asp Asp Leu Ser Pro Ala Pro Asp Ala Trp Ser Arg Pro
            180                 185                 190

Asp Ile Pro Leu His Ala Gln Ala Met Leu Lys Asn Ala Arg Glu Gly
        195                 200                 205

Ile Glu Pro Asp Gln Pro Gly Val Val Gly Pro Ile Lys Gln Ile Glu
    210                 215                 220

Ala Leu Gln Lys Lys Gly Tyr Pro Leu Ala Tyr Val Gly Asp Val Val
225                 230                 235                 240

Gly Thr Gly Ser Ser Arg Lys Ser Ala Thr Asn Ser Val Leu Trp Phe
                245                 250                 255

Met Gly Asp Asp Ile Pro Asn Val Pro Asn Lys Arg Gly Gly Gly Leu
            260                 265                 270

Cys Leu Gly Gly Lys Ile Ala Pro Ile Phe Phe Asn Thr Met Glu Asp
        275                 280                 285

Ala Gly Ala Leu Pro Ile Glu Val Asp Val Ser Asn Leu Asn Met Gly
    290                 295                 300

Asp Val Ile Asp Val Tyr Pro Tyr Lys Gly Glu Val Arg Asn His Glu
305                 310                 315                 320

Thr Asp Glu Leu Leu Ala Thr Phe Glu Leu Lys Thr Asp Val Leu Ile
                325                 330                 335

Asp Glu Val Arg Ala Gly Gly Arg Ile Pro Leu Ile Ile Gly Arg Gly
            340                 345                 350

Leu Thr Thr Lys Ala Arg Glu Ala Leu Gly Leu Pro His Ser Asp Val
        355                 360                 365

Phe Arg Gln Ala Lys Asp Val Ala Glu Ser Ser Arg Gly Phe Ser Leu
    370                 375                 380

Ala Gln Lys Met Val Gly Arg Ala Cys Gly Val Lys Gly Ile Arg Pro
385                 390                 395                 400

Gly Ala Tyr Cys Glu Pro Lys Met Thr Ser Val Gly Ser Gln Asp Thr
                405                 410                 415

Thr Gly Pro Met Thr Arg Asp Glu Leu Lys Asp Leu Ala Cys Leu Gly
            420                 425                 430

Phe Ser Ala Asp Leu Val Met Gln Ser Phe Cys His Thr Ala Ala Tyr
        435                 440                 445

Pro Lys Pro Val Asp Val Thr Thr His His Thr Leu Pro Asp Phe Ile
    450                 455                 460

Met Asn Arg Gly Gly Val Ser Leu Arg Pro Gly Asp Gly Val Ile His
465                 470                 475                 480

Ser Trp Leu Asn Arg Met Leu Leu Pro Asp Thr Val Gly Thr Gly Gly
                485                 490                 495
```

-continued

```
Asp Ser His Thr Arg Phe Pro Ile Gly Ile Ser Phe Pro Ala Gly Ser
            500                 505                 510

Gly Leu Val Ala Phe Ala Ala Thr Gly Val Met Pro Leu Asp Met
        515                 520                 525

Pro Glu Ser Val Leu Val Arg Phe Lys Gly Lys Met Gln Pro Gly Ile
    530                 535                 540

Thr Leu Arg Asp Leu Val His Ala Ile Pro Leu Tyr Ala Ile Lys Gln
545                 550                 555                 560

Gly Leu Leu Thr Val Glu Lys Lys Gly Lys Asn Ile Phe Ser Gly
                565                 570                 575

Arg Ile Leu Glu Ile Glu Gly Leu Pro Asp Leu Lys Val Glu Gln Ala
                580                 585                 590

Phe Glu Leu Thr Asp Ala Ser Ala Glu Arg Ser Ala Ala Gly Cys Thr
    595                 600                 605

Ile Lys Leu Asn Lys Glu Pro Ile Val Glu Tyr Leu Thr Ser Asn Ile
        610                 615                 620

Val Leu Leu Lys Trp Met Ile Ala Glu Gly Tyr Gly Asp Arg Arg Thr
625                 630                 635                 640

Leu Glu Arg Arg Ile Gln Gly Met Glu Lys Trp Leu Ala Asp Pro Gln
                645                 650                 655

Leu Leu Glu Ala Asp Ala Asp Ala Glu Tyr Ala Ala Val Ile Asp Ile
                660                 665                 670

Asp Leu Ala Asp Ile Lys Glu Pro Ile Leu Cys Ala Pro Asn Asp Pro
            675                 680                 685

Asp Asp Ala Arg Leu Leu Ser Asp Val Gln Gly Glu Lys Ile Asp Glu
        690                 695                 700

Val Phe Ile Gly Ser Cys Met Thr Asn Ile Gly His Phe Arg Ala Ala
705                 710                 715                 720

Gly Lys Leu Leu Asp Ser His Lys Gly Gln Leu Pro Thr Arg Leu Trp
                725                 730                 735

Val Ala Pro Pro Thr Arg Met Asp Ala Ala Gln Leu Thr Glu Glu Gly
            740                 745                 750

Tyr Tyr Ser Val Phe Gly Lys Ser Gly Ala Arg Ile Glu Ile Pro Gly
        755                 760                 765

Cys Ser Leu Cys Met Gly Asn Gln Ala Arg Val Ala Asp Gly Ala Thr
        770                 775                 780

Val Val Ser Thr Ser Thr Arg Asn Phe Pro Asn Arg Leu Gly Thr Gly
785                 790                 795                 800

Ala Asn Val Phe Leu Ala Ser Ala Glu Leu Ala Ala Val Ala Ala Leu
                805                 810                 815

Ile Gly Lys Leu Pro Thr Pro Glu Glu Tyr Gln Thr Phe Val Ala Gln
            820                 825                 830

Val Asp Lys Thr Ala Val Asp Thr Tyr Arg Tyr Leu Asn Phe Asp Gln
        835                 840                 845

Leu Ser Gln Tyr Thr Glu Lys Ala Asp Gly Val Ile Phe Gln Thr Ala
    850                 855                 860

Val
865
```

<210> SEQ ID NO 37
<211> LENGTH: 1539
<212> TYPE: DNA
<213> ORGANISM: Escherichia coli

<400> SEQUENCE: 37

```
atgaccaata tcccccttc agcacagatt aagcccggcg agtatggttt ccccctcaag      60
ttaaaagccc gctatgacaa ctttattggc ggcgaatggg tagcccctgc cgacggcgag    120
tattaccaga atctgacgcc ggtgaccggg cagctgctgt gcgaagtggc gtcttcgggc    180
aaacgagaca tcgatctggc gctggatgct gcgcacaaag tgaaagataa atgggcgcac    240
acctcggtgc aggatcgtgc ggcgattctg tttaagattg ccgatcgaat ggaacaaaac    300
ctcgagctgt tagcgacagc tgaaacctgg gataacggca aacccattcg cgaaaccagt    360
gctgcggatg taccgctggc gattgaccat ttccgctatt tcgcctcgtg tattcgggcg    420
caggaaggtg ggatcagtga agttgatagc gaaaccgtgg cctatcattt ccatgaaccg    480
ttaggcgtgg tggggcagat tatcccgtgg aacttcccgc tgctgatggc gagctggaaa    540
atggctcccg cgctggcggc gggcaactgt gtggtgctga acccgcacg tcttaccccg    600
ctttctgtac tgctgctaat ggaaattgtc ggtgatttac tgccgccggg cgtggtgaac    660
gtggtcaatg gcgcaggtgg ggtaattggc gaatatctgg cgacctcgaa acgcatcgcc    720
aaagtggcgt ttaccggctc aacggaagtg ggccaacaaa ttatgcaata cgcaacgcaa    780
aacattattc cggtgacgct ggagttgggc ggtaagtcgc caaatatctt ctttgctgat    840
gtgatggatg aagaagatgc cttttttcgat aaagcgctgg aaggctttgc actgtttgcc    900
tttaaccagg cgaagtttg cacctgtccg agtcgtgctt tagtgcagga atctatctac    960
gaacgcttta tggaacgcgc catccgccgt gtcgaaagca ttcgtagcgg taacccgctc   1020
gacagcgtga cgcaaatggg cgcgcaggtt tctcacgggc aactgaaaac catcctcaac   1080
tacattgata tcggtaaaaa agagggcgct gacgtgctca caggcgggcg cgcaagctg   1140
ctggaaggtg aactgaaaga cggctactac ctcgaaccga cgattctgtt tggtcagaac   1200
aatatgcggg tgttccagga ggagattttt ggcccggtgc tggcggtgac caccttcaaa   1260
acgatggaag aagcgctgga gctggcgaac gatacgcaat atggcctggg cgcgggcgtc   1320
tggagccgca acggtaatct ggcctataag atggggcgcg gcatacaggc tgggcgcgtg   1380
tggaccaact gttatcacgc ttacccggca catgcggcgt ttggtggcta caaacaatca   1440
ggtatcggtc gcgaaaccca aagatgatg ctggagcatt accagcaaac caagtgcctg   1500
ctggtgagct actcggataa accgttgggg ctgttctga                          1539
```

<210> SEQ ID NO 38
<211> LENGTH: 512
<212> TYPE: PRT
<213> ORGANISM: Escherichia coli

<400> SEQUENCE: 38

```
Met Thr Asn Asn Pro Pro Ser Ala Gln Ile Lys Pro Gly Glu Tyr Gly
  1               5                  10                  15

Phe Pro Leu Lys Leu Lys Ala Arg Tyr Asp Asn Phe Ile Gly Gly Glu
                 20                  25                  30

Trp Val Ala Pro Ala Asp Gly Glu Tyr Tyr Gln Asn Leu Thr Pro Val
             35                  40                  45

Thr Gly Gln Leu Leu Cys Glu Val Ala Ser Ser Gly Lys Arg Asp Ile
         50                  55                  60

Asp Leu Ala Leu Asp Ala Ala His Lys Val Lys Asp Lys Trp Ala His
 65                  70                  75                  80

Thr Ser Val Gln Asp Arg Ala Ala Ile Leu Phe Lys Ile Ala Asp Arg
                 85                  90                  95
```

```
Met Glu Gln Asn Leu Glu Leu Leu Ala Thr Ala Glu Thr Trp Asp Asn
                100                 105                 110
Gly Lys Pro Ile Arg Glu Thr Ser Ala Ala Asp Val Pro Leu Ala Ile
            115                 120                 125
Asp His Phe Arg Tyr Phe Ala Ser Cys Ile Arg Ala Gln Glu Gly Gly
        130                 135                 140
Ile Ser Glu Val Asp Ser Glu Thr Val Ala Tyr His Phe His Glu Pro
145                 150                 155                 160
Leu Gly Val Val Gly Gln Ile Ile Pro Trp Asn Phe Pro Leu Leu Met
                165                 170                 175
Ala Ser Trp Lys Met Ala Pro Ala Leu Ala Ala Gly Asn Cys Val Val
            180                 185                 190
Leu Lys Pro Ala Arg Leu Thr Pro Leu Ser Val Leu Leu Met Glu
        195                 200                 205
Ile Val Gly Asp Leu Leu Pro Pro Gly Val Val Asn Val Val Asn Gly
    210                 215                 220
Ala Gly Gly Val Ile Gly Glu Tyr Leu Ala Thr Ser Lys Arg Ile Ala
225                 230                 235                 240
Lys Val Ala Phe Thr Gly Ser Thr Glu Val Gly Gln Gln Ile Met Gln
                245                 250                 255
Tyr Ala Thr Gln Asn Ile Ile Pro Val Thr Leu Glu Leu Gly Gly Lys
            260                 265                 270
Ser Pro Asn Ile Phe Phe Ala Asp Val Met Asp Glu Glu Asp Ala Phe
        275                 280                 285
Phe Asp Lys Ala Leu Glu Gly Phe Ala Leu Phe Ala Phe Asn Gln Gly
    290                 295                 300
Glu Val Cys Thr Cys Pro Ser Arg Ala Leu Val Gln Glu Ser Ile Tyr
305                 310                 315                 320
Glu Arg Phe Met Glu Arg Ala Ile Arg Arg Val Glu Ser Ile Arg Ser
                325                 330                 335
Gly Asn Pro Leu Asp Ser Val Thr Gln Met Gly Ala Gln Val Ser His
            340                 345                 350
Gly Gln Leu Glu Thr Ile Leu Asn Tyr Ile Asp Ile Gly Lys Lys Glu
        355                 360                 365
Gly Ala Asp Val Leu Thr Gly Gly Arg Arg Lys Leu Leu Glu Gly Glu
    370                 375                 380
Leu Lys Asp Gly Tyr Tyr Leu Glu Pro Thr Ile Leu Phe Gly Gln Asn
385                 390                 395                 400
Asn Met Arg Val Phe Gln Glu Glu Ile Phe Gly Pro Val Leu Ala Val
                405                 410                 415
Thr Thr Phe Lys Thr Met Glu Glu Ala Leu Glu Leu Ala Asn Asp Thr
            420                 425                 430
Gln Tyr Gly Leu Gly Ala Gly Val Trp Ser Arg Asn Gly Asn Leu Ala
        435                 440                 445
Tyr Lys Met Gly Arg Gly Ile Gln Ala Gly Arg Val Trp Thr Asn Cys
    450                 455                 460
Tyr His Ala Tyr Pro Ala His Ala Ala Phe Gly Gly Tyr Lys Gln Ser
465                 470                 475                 480
Gly Ile Gly Arg Glu Thr His Lys Met Met Leu Glu His Tyr Gln Gln
                485                 490                 495
Thr Lys Cys Leu Leu Val Ser Tyr Ser Asp Lys Pro Leu Gly Leu Phe
            500                 505                 510
```

<210> SEQ ID NO 39
<211> LENGTH: 1473
<212> TYPE: DNA
<213> ORGANISM: Pantoea ananatis

<400> SEQUENCE: 39

```
atgtcagatt ttgatcccga taaggtccgt ctttcgaccg acatttttat caacggccag    60
tttgtttcgg catccggcaa aacaatgggg attaaacgtc cctcggatgg ccagcattat   120
gccgacatca acgaagcggg cgcagaaacg gtcggcgagg cggtaagcct cgcggaagac   180
gcgcgcattc gcagcggctg gtcaagctgc tcgccacgcg aacggggcgc ggccatttcc   240
cgctgggcgg atttgatcga tgccgacaaa gattatctgg cgcagcttga ggcggtgggc   300
tccacgcgtc cgataacgga cacgatcaat attgaagtgc ctttcaccgc cgctgctctg   360
cgttttatg cagaatgcgc agacaagtac agcggagatg tgtttccaac ccagaacagt   420
agcctgggga tgctggtgcc ggagccttat ggcgtgatcg gcgcgatcac gccgtggaat   480
ttcccgctgt cgatggcgtc gtggaagtgc ggcccggcgc tggctgcggg aaacgcggtg   540
gtactcaagc cctctgagct gacgccattc tccaccgcgc ggctggctga gctggccgtg   600
caggccggta ttccgcccgg tgtgctcaac gtcgttcagg gcggcggaca ggtcaccggc   660
aatgcactgg tgacccatcc tctggtcaga aaggtgtcct ttaccggttc aaccgcgacc   720
ggggcggcga tcatgagcca ggccgcgttg cacggtacca agcccgtgac gctggaactg   780
ggcggaaaaa gcccgcagct ggttttttgac gatgcaggcg atgcggatga atcgccgag   840
cgcctgtttc tgggcttcac cgtcaacgcc ggtcaggcct gtgtttcagg gacgcgtctg   900
atcattcaac aaggtatcgc agaacgggtc atcgaaaagc ttatcgccct atgcaaaaca   960
ccgctgcccg gtatgacctg gcaggccgcc acgcgttact gtccgctgat cgatcaacgt  1020
caggggaaa agtcgcgac gattatcgcg cagtccgtgg cgcaggggc cagcattctg  1080
gccggcggcc agcgttacga aaacaccgcg cagggctggt tctggcaacc gacgctgtta  1140
gccaatgtga atcaggataa cgtcgcgatt caggaggaga tcttcggacc ggtgctcacc  1200
atccagacgt ttagcgatga agaagaagcc ctggcgctcg cacagcatcg cgttttttggc  1260
ttatgtgcag gcgtgcatac gctcaacatg ccacgtgcga tgcggctgat gaaagccctg  1320
gacagcggta cggtctggat caaccgctat cgtcgaacct gggactttat cattccaacc  1380
ggcggctttc aggggtccgg ttttggcaaa gatcttgggc gccaggcctt tgagtcatgt  1440
cagcgctaca agagtgtctt aatcgatttt taa                              1473
```

<210> SEQ ID NO 40
<211> LENGTH: 490
<212> TYPE: PRT
<213> ORGANISM: Pantoea ananatis

<400> SEQUENCE: 40

```
Met Ser Asp Phe Asp Pro Asp Lys Val Arg Leu Ser Thr Gly His Phe
 1               5                  10                  15

Ile Asn Gly Gln Phe Val Ser Ala Ser Gly Lys Thr Met Gly Ile Lys
             20                  25                  30

Arg Pro Ser Asp Gly Gln His Tyr Ala Asp Ile Asn Glu Ala Gly Ala
         35                  40                  45

Glu Thr Val Gly Glu Ala Val Ser Leu Ala Glu Asp Ala Arg Ile Arg
     50                  55                  60

Ser Gly Trp Ser Ser Cys Ser Pro Arg Glu Arg Gly Ala Ala Ile Ser
 65                  70                  75                  80
```

```
Arg Trp Ala Asp Leu Ile Asp Ala Asp Lys Asp Tyr Leu Ala Gln Leu
                 85                  90                  95

Glu Ala Val Gly Ser Thr Arg Pro Ile Thr Asp Thr Ile Asn Ile Glu
            100                 105                 110

Val Pro Phe Thr Ala Ala Ala Leu Arg Phe Tyr Ala Glu Cys Ala Asp
            115                 120                 125

Lys Tyr Ser Gly Asp Val Phe Pro Thr Gln Asn Ser Ser Leu Gly Met
            130                 135                 140

Leu Val Pro Glu Pro Tyr Gly Val Ile Gly Ala Ile Thr Pro Trp Asn
145                 150                 155                 160

Phe Pro Leu Ser Met Ala Ser Trp Lys Cys Gly Pro Ala Leu Ala Ala
                165                 170                 175

Gly Asn Ala Val Val Leu Lys Pro Ser Glu Leu Thr Pro Phe Ser Thr
            180                 185                 190

Ala Arg Leu Ala Glu Leu Ala Val Gln Ala Gly Ile Pro Pro Gly Val
            195                 200                 205

Leu Asn Val Val Gln Gly Gly Gln Val Thr Gly Asn Ala Leu Val
210                 215                 220

Thr His Pro Leu Val Arg Lys Val Ser Phe Thr Gly Ser Thr Ala Thr
225                 230                 235                 240

Gly Ala Ala Ile Met Ser Gln Ala Ala Leu His Gly Thr Lys Pro Val
                245                 250                 255

Thr Leu Glu Leu Gly Gly Lys Ser Pro Gln Leu Val Phe Asp Asp Ala
            260                 265                 270

Gly Asp Ala Asp Glu Ile Ala Glu Arg Leu Phe Leu Gly Phe Thr Val
            275                 280                 285

Asn Ala Gly Gln Ala Cys Val Ser Gly Thr Arg Leu Ile Ile Gln Gln
290                 295                 300

Gly Ile Ala Glu Arg Val Ile Glu Lys Leu Ile Ala Leu Cys Lys Thr
305                 310                 315                 320

Pro Leu Pro Gly Met Thr Trp Gln Ala Ala Thr Arg Tyr Cys Pro Leu
                325                 330                 335

Ile Asp Gln Arg Gln Gly Glu Lys Val Ala Thr Ile Ile Ala Gln Ser
            340                 345                 350

Val Ala Gln Gly Ala Ser Ile Leu Ala Gly Gly Gln Arg Tyr Glu Asn
            355                 360                 365

Thr Ala Gln Gly Trp Phe Trp Gln Pro Thr Leu Leu Ala Asn Val Asn
            370                 375                 380

Gln Asp Asn Val Ala Ile Gln Glu Glu Ile Phe Gly Pro Val Leu Thr
385                 390                 395                 400

Ile Gln Thr Phe Ser Asp Glu Glu Glu Ala Leu Ala Leu Ala Gln His
                405                 410                 415

Arg Val Phe Gly Leu Cys Ala Gly Val His Thr Leu Asn Met Pro Arg
            420                 425                 430

Ala Met Arg Leu Met Lys Ala Leu Asp Ser Gly Thr Val Trp Ile Asn
            435                 440                 445

Arg Tyr Arg Arg Thr Trp Asp Phe Ile Ile Pro Thr Gly Gly Phe Gln
            450                 455                 460

Gly Ser Gly Phe Gly Lys Asp Leu Gly Arg Gln Ala Phe Glu Ser Cys
465                 470                 475                 480

Gln Arg Tyr Lys Ser Val Leu Ile Asp Phe
            485                 490
```

```
<210> SEQ ID NO 41
<211> LENGTH: 1536
<212> TYPE: DNA
<213> ORGANISM: Pectobacterium atrosepticum

<400> SEQUENCE: 41
atggcgcacg ataatctcga aggccgatcc gcatttggcg aagtcggttc tctcgatctg      60
aaaaaacgct atgacaattt tatcggtgga acctgggttc cgcctgatgc tggtcagtat     120
tttgtcaatt taacgccagt gacaggccag ccgatgtgtg aagtagccag ttcgtcaacg     180
cgagatattg accacgcgct ggatgcagcc cacaaggcaa aagcggaatg ggtggtcta      240 tcggtacaga acgggcgct ggtgcttaac cgtattgccg accggatgga acaaaatctt     300
gaacggctag cgcaggtgga aacctgggat aacggtaagc cgatacgtga acaagcggg      360 gcggatgtgc cgctggcgat tgaccacttt cgttattttg ctgcctgtat ccgcgcgcaa     420 gaggggggcaa tcagcgaaat tgacggcgat accgtggcct atcattttca tgagcctctt    480
ggcgttgttg cgcaaatcat tccctggaac ttcccgctgc tgatggcctg ttggaagatg    540
gctcctgcac tggcagccgg taactgtatt gtactgaagc ctgccaagct gacgccgatg    600
tcggtgctga ttttgatgga gcttattcag gatctgctgc ctgcggggt cattaatgtc     660 gtcaatggat cgggaagtga gattggcgag tatctggcaa catcgaaacg cgttgcgaaa    720
gtcgcattca ccgggtcaac cgaagtgggc cagcagatca tgagctatgc ggcacagaat    780
gtgacgccgg tgacgctgga attgggtggc aaatcgccga acatcttctt tgccgatgtg    840
atggataagg aagatagttt ctttgacaaa gcgctcgaag gtttcacgct gtttgccttc    900
aatcagggag aggttttgcac ctgcccgagc gcgcgcgctgg tgcaggaatc tatctatgat    960
cgctttatgg aacgggcaat caagcgcgtt gaagctatcc gcatcggtaa cccgctggac   1020
agcaaaacca tgatgggcgc acaggtgtca gcaggccagc tcgaaaccat ccttaactat   1080
attgatatcg gtaagaaaga gggcgcacgg gtactcactg gcggcagcg taaggcgatg   1140 ccgggcgggc tggcggaagg ctactatttg gagccgacga tattgttcgg taaaaatagt   1200
atgcgtgtct ttcaggagga aattttcggt ccggtgttgg cggtaacaac gttcaagacg   1260
atggaagatg cgctggagat agctaacgat acggaatacg gtctgggtgc tggcgtgtgg   1320
agccgtaacg gtaacgtcgc ttaccgaatg gggcgcggca ttcaggctgg tcgagtttgg   1380
accaactgtt atcacgccta tccggcacat gccgcgtttg ggggctataa gcagtccggt   1440
atcgggcgtg agaatcataa aatgatgctg gatcattatc agcaaaccaa gtgcctgttg   1500
gtgagttact ctgataagcc gatggggctg ttctaa                              1536

<210> SEQ ID NO 42
<211> LENGTH: 511
<212> TYPE: PRT
<213> ORGANISM: Pectobacterium atrosepticum

<400> SEQUENCE: 42

Met Ala His Asp Asn Leu Glu Gly Arg Ser Ala Phe Gly Glu Val Gly
1               5                   10                  15

Ser Leu Asp Leu Lys Lys Arg Tyr Asp Asn Phe Ile Gly Gly Thr Trp
            20                  25                  30

Val Pro Pro Asp Ala Gly Gln Tyr Phe Val Asn Leu Thr Pro Val Thr
        35                  40                  45

Gly Gln Pro Met Cys Glu Val Ala Ser Ser Ser Thr Arg Asp Ile Asp
    50                  55                  60
```

-continued

His Ala Leu Asp Ala Ala His Lys Ala Lys Ala Glu Trp Gly Gly Leu
 65                  70                  75                  80

Ser Val Gln Glu Arg Ala Leu Val Leu Asn Arg Ile Ala Asp Arg Met
                 85                  90                  95

Glu Gln Asn Leu Glu Arg Leu Ala Gln Val Glu Thr Trp Asp Asn Gly
            100                 105                 110

Lys Pro Ile Arg Glu Thr Ser Gly Ala Asp Val Pro Leu Ala Ile Asp
        115                 120                 125

His Phe Arg Tyr Phe Ala Ala Cys Ile Arg Ala Gln Glu Gly Ala Ile
    130                 135                 140

Ser Glu Ile Asp Gly Asp Thr Val Ala Tyr His Phe His Glu Pro Leu
145                 150                 155                 160

Gly Val Val Ala Gln Ile Ile Pro Trp Asn Phe Pro Leu Leu Met Ala
                165                 170                 175

Cys Trp Lys Met Ala Pro Ala Leu Ala Ala Gly Asn Cys Ile Val Leu
            180                 185                 190

Lys Pro Ala Lys Leu Thr Pro Met Ser Val Leu Ile Leu Met Glu Leu
        195                 200                 205

Ile Gln Asp Leu Leu Pro Ala Gly Val Ile Asn Val Val Asn Gly Ser
    210                 215                 220

Gly Ser Glu Ile Gly Glu Tyr Leu Ala Thr Ser Lys Arg Val Ala Lys
225                 230                 235                 240

Val Ala Phe Thr Gly Ser Thr Glu Val Gly Gln Gln Ile Met Ser Tyr
                245                 250                 255

Ala Ala Gln Asn Val Thr Pro Val Thr Leu Glu Leu Gly Gly Lys Ser
            260                 265                 270

Pro Asn Ile Phe Phe Ala Asp Val Met Asp Lys Glu Asp Ser Phe Phe
        275                 280                 285

Asp Lys Ala Leu Glu Gly Phe Thr Leu Phe Ala Phe Asn Gln Gly Glu
    290                 295                 300

Val Cys Thr Cys Pro Ser Arg Ala Leu Val Gln Glu Ser Ile Tyr Asp
305                 310                 315                 320

Arg Phe Met Glu Arg Ala Ile Lys Arg Val Glu Ala Ile Arg Ile Gly
                325                 330                 335

Asn Pro Leu Asp Ser Lys Thr Met Met Gly Ala Gln Val Ser Ala Gly
            340                 345                 350

Gln Leu Glu Thr Ile Leu Asn Tyr Ile Asp Ile Gly Lys Lys Glu Gly
        355                 360                 365

Ala Arg Val Leu Thr Gly Gly Gln Arg Lys Ala Met Pro Gly Gly Leu
    370                 375                 380

Ala Glu Gly Tyr Tyr Leu Glu Pro Thr Ile Leu Phe Gly Lys Asn Ser
385                 390                 395                 400

Met Arg Val Phe Gln Glu Glu Ile Phe Gly Pro Val Leu Ala Val Thr
                405                 410                 415

Thr Phe Lys Thr Met Glu Asp Ala Leu Glu Ile Ala Asn Asp Thr Glu
            420                 425                 430

Tyr Gly Leu Gly Ala Gly Val Trp Ser Arg Asn Gly Asn Val Ala Tyr
        435                 440                 445

Arg Met Gly Arg Gly Ile Gln Ala Gly Arg Val Trp Thr Asn Cys Tyr
    450                 455                 460

His Ala Tyr Pro Ala His Ala Ala Phe Gly Gly Tyr Lys Gln Ser Gly
465                 470                 475                 480

Ile Gly Arg Glu Asn His Lys Met Met Leu Asp His Tyr Gln Gln Thr
                485                 490                 495

Lys Cys Leu Leu Val Ser Tyr Ser Asp Lys Pro Met Gly Leu Phe
        500                 505                 510

<210> SEQ ID NO 43
<211> LENGTH: 1539
<212> TYPE: DNA
<213> ORGANISM: Salmonella enterica

<400> SEQUENCE: 43

| | | | | | |
|---|---|---|---|---|---|
| atgacgaaca | atcccccttc | aacacgtatt | cagccaagtg | aatacgggta | cccactgaag | 60 |
| ttaaaagccc | gctatgacaa | ttttattggc | ggtgactggg | ttgcgcccgc | cgacggcgaa | 120 |
| tattatcaaa | acctgacgcc | agtgaccggc | cagccgctat | gtgaagtcgc | ttcctccggt | 180 |
| aaaaaagata | tcgatttagc | gctcgacgcc | gcgcataagg | cgaaagataa | gtgggcgcat | 240 |
| acgtcagtac | aagaccgtgc | cgctatcttg | tttaagatcg | ccgatcggat | ggaacaaaac | 300 |
| ctcgaactgt | tggcgacagc | ggaaacttgg | ataacggta | aaccgattcg | tgaaaccagt | 360 |
| gccgccgaca | taccgctggc | gatcgatcat | ttccgctatt | cgcctcctg | tatacgtgcg | 420 |
| caggagggcg | ggatcagcga | agttgatagc | gaaaccgtgg | cctaccattt | tcacgaaccg | 480 |
| cttggtgtcg | tggggcagat | aatcccgtgg | aactttccgc | tgctgatggc | aagctggaaa | 540 |
| atggcgccag | cgctggcggc | aggtaactgc | gtggtgctta | aaccggcacg | cctgacgccg | 600 |
| ctttccgttt | tactgttaat | ggaagtcatt | ggcgatctgt | accgccgggg | cgttgtcaac | 660 |
| gtcgtgaacg | gcgcgggcgg | cgagattggc | gaatatctgg | cgacctcaaa | acgtatcgcg | 720 |
| aaggtggcgt | ttaccggttc | gacggaagtg | ggtcaacaga | tcatgcagta | cgccacgcag | 780 |
| aacattattc | cggtgacgct | ggagttaggc | ggcaagtcgc | ccaatatctt | cttcgccgac | 840 |
| gtgatggatg | aggaagatgc | gttctttgat | aaagcgctgg | agggatttgc | cctgtttgcc | 900 |
| tttaaccagg | gcgaggtgtg | tacctgtcca | agccgtgcgc | tggttcagga | gtccatctat | 960 |
| gagcgcttta | tggagcgcgc | tattcgccgg | gtggagagca | ttcgcagcgg | gaacccgcta | 1020 |
| gatagcggta | cacagatggg | agcgcaggtc | tctcacggcc | agcttgagac | tatcctcaat | 1080 |
| tatatcgata | tcggtaaaaa | agagggggcc | gatattctga | ccggtgggcg | acgcaaggaa | 1140 |
| ctggatggcg | aacttaaaga | gggctattac | cttgagccta | ccattctgtt | tggtaagaat | 1200 |
| aatatgcgcg | tctttcagga | ggagatcttt | ggcccggtgc | tggcggtaac | cacctttaaa | 1260 |
| accatggaga | aggcgctgga | aatcgctaac | gatacgcaat | atggcctggg | tgctggcgtc | 1320 |
| tggagccgca | acggcaatct | ggcctataag | atggggcgcg | gcattcaggc | cgggcgcgta | 1380 |
| tggaccaact | gctatcacgc | ctatccggca | catgcgcgt | ttggcggcta | taagcagtcg | 1440 |
| ggcatcgggc | gcgaaaccca | taagatgatg | ctggaacact | accagcaaac | caagtgcctg | 1500 |
| ttggtgagtt | attccgataa | gccgctgggg | ctgttctga | | | 1539 |

<210> SEQ ID NO 44
<211> LENGTH: 512
<212> TYPE: PRT
<213> ORGANISM: Salmonella enterica

<400> SEQUENCE: 44

Met Thr Asn Asn Pro Pro Ser Thr Arg Ile Gln Pro Ser Glu Tyr Gly
1               5                   10                  15

Tyr Pro Leu Lys Leu Lys Ala Arg Tyr Asp Asn Phe Ile Gly Gly Asp
            20                  25                  30

-continued

```
Trp Val Ala Pro Ala Asp Gly Glu Tyr Tyr Gln Asn Leu Thr Pro Val
         35                  40                  45

Thr Gly Gln Pro Leu Cys Glu Val Ala Ser Ser Gly Lys Lys Asp Ile
 50                  55                  60

Asp Leu Ala Leu Asp Ala Ala His Lys Ala Lys Asp Lys Trp Ala His
 65                  70                  75                  80

Thr Ser Val Gln Asp Arg Ala Ala Ile Leu Phe Lys Ile Ala Asp Arg
                 85                  90                  95

Met Glu Gln Asn Leu Glu Leu Leu Ala Thr Ala Glu Thr Trp Asp Asn
                100                 105                 110

Gly Lys Pro Ile Arg Glu Thr Ser Ala Ala Asp Ile Pro Leu Ala Ile
            115                 120                 125

Asp His Phe Arg Tyr Phe Ala Ser Cys Ile Arg Ala Gln Glu Gly Gly
        130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Leu Met Glu
        195                 200                 205

Val Ile Gly Asp Leu Leu Pro Pro Gly Val Val Asn Val Val Asn Gly
210                 215                 220

Ala Gly Gly Glu Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Glu Asp Ala Phe
        275                 280                 285

Phe Asp Lys Ala Leu Glu Gly Phe Ala Leu Phe Ala Phe Asn Gln Gly
290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Gly Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Ile Leu Thr Gly Gly Arg Arg Lys Glu Leu Asp Gly Glu
        370                 375                 380

Leu Lys Glu Gly Tyr Tyr Leu Glu Pro Thr Ile Leu Phe Gly Lys Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Lys Ala Leu Glu Ile Ala Asn Asp Thr
            420                 425                 430

Gln Tyr Gly Leu Gly Ala Gly Val Trp Ser Arg Asn Gly Asn Leu Ala
        435                 440                 445
```

| | | | | | | | | | | | | |
|---|---|---|---|---|---|---|---|---|---|---|---|---|
|Tyr|Lys|Met|Gly|Arg|Gly|Ile|Gln|Ala|Gly|Arg|Val|Trp|Thr|Asn|Cys|
| |450| | | |455| | | |460| | | | | | |

| | | | | | | | | | | | |
|---|---|---|---|---|---|---|---|---|---|---|---|
|Tyr|His|Ala|Tyr|Pro|Ala|His|Ala|Ala|Phe|Gly|Gly|Tyr|Lys|Gln|Ser|
|465| | | | |470| | | | |475| | | | |480|

| | | | | | | | | | | | |
|---|---|---|---|---|---|---|---|---|---|---|---|
|Gly|Ile|Gly|Arg|Glu|Thr|His|Lys|Met|Met|Leu|Glu|His|Tyr|Gln|Gln|
| | | | |485| | | | |490| | | | |495| |

| | | | | | | | | | | | |
|---|---|---|---|---|---|---|---|---|---|---|---|
|Thr|Lys|Cys|Leu|Leu|Val|Ser|Tyr|Ser|Asp|Lys|Pro|Leu|Gly|Leu|Phe|
| | | |500| | | |505| | | |510| | | | |

<210> SEQ ID NO 45
<211> LENGTH: 2676
<212> TYPE: DNA
<213> ORGANISM: Escherichia coli

<400> SEQUENCE: 45

```
atggctgtta ctaatgtcgc tgaacttaac gcactcgtag agcgtgtaaa aaaagcccag      60
cgtgaatatg ccagtttcac tcaagagcaa gtagacaaaa tcttccgcgc cgccgctctg     120
gctgctgcag atgctcgaat cccactcgcg aaaatggccg ttgccgaatc cggcatgggt     180
atcgtcgaag ataaagtgat caaaaaccac tttgcttctg aatatatcta caacgcctat     240
aaagatgaaa aaacctgtgg tgttctgtct gaagacgaca cttttggtac catcactatc     300
gctgaaccaa tcggtattat ttgcggtatc gttccgacca ctaacccgac ttcaactgct     360
atcttcaaat cgctgatcag tctgaagacc cgtaacgcca ttatcttctc cccgcacccg     420
cgtgcaaaag atgccaccaa caaagcggct gatatcgttc tgcaggctgc tatcgctgcc     480
ggtgctccga agatctgat cggctggatc gatcaacctt ctgttgaact gtctaacgca     540
ctgatgcacc acccagacat caacctgatc ctcgcgactg gtggtccggg catggttaaa     600
gccgcataca gctccggtaa accagctatc ggtgtaggcg cgggcaacac tccagttgtt     660
atcgatgaaa ctgctgatat caaacgtgca gttgcatctg tactgatgtc caaaaccttc     720
gacaacggcg taatctgtgc ttctgaacag tctgttgttg ttgttgactc tgtttatgac     780
gctgtacgtg aacgttttgc aacccacggc ggctatctgt gcagggtaa agagctgaaa     840
gctgttcagg atgttatcct gaaaaacggt gcgctgaacg cggctatcgt tggtcagcca     900
gcctataaaa ttgctgaact ggcaggcttc tctgtaccag aaaacaccaa gattctgatc     960
ggtgaagtga ccgttgttga tgaaagcgaa ccgttcgcac atgaaaaact gtccccgact    1020
ctggcaatgt accgcgctaa agatttcgaa gacgcggtag aaaagcaga gaaactggtt    1080
gctatgggcg gtatcggtca tacctcttgc ctgtacactg accaggataa ccaaccggct    1140
cgcgtttctt acttcggtca gaaatgaaa acggcgcgta tcctgattaa caccccagcg    1200
tctcagggtg gtatcggtga cctgtataac ttcaaactcg caccttccct gactctgggt    1260
tgtggttctt ggggtggtaa ctccatctct gaaaacgttg gtccgaaaca cctgatcaac    1320
aagaaaaccg ttgctaagcg agctgaaaac atgttgtggc acaaacttcc gaaatctatc    1380
tacttccgcc gtggctccct gccaatcgcg ctggatgaag tgattactga tggccacaaa    1440
cgtgcgctca tcgtgactga ccgcttcctg ttcaacaatg ttatgctga tcagatcact    1500
tccgtactga aagcagcagg cgttgaaact gaagtcttct tcgaagtaga agcggacccg    1560
accctgagca tcgttcgtaa aggtgcagaa ctggcaaact ccttcaaacc agacgtgatt    1620
atcgcgctgg gtggtggttc cccgatggac gccgcgaaga tcatgtgggt tatgtacgaa    1680
catccggaaa ctcacttcga agagctggcg ctgcgcttta tggatatccg taacgtatc    1740
tacaagttcc cgaaaatggg cgtgaaagcg aaaatgatcg ctgtcaccac cacttctggt    1800
```

```
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga agtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac acgaagggt ctaaaaatcc ggtagcgcgt    2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttaccgctg atctccgagc tgaaacagat tctgctggat   2580
acctactacg tcgtgatta tgtagaaggt gaaactgcag cgaagaaaga agctgctccg   2640
gctaaagctg agaaaaaagc gaaaaaatcc gcttaa                            2676
```

<210> SEQ ID NO 46
<211> LENGTH: 891
<212> TYPE: PRT
<213> ORGANISM: Escherichia coli

<400> SEQUENCE: 46

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220
```

```
Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
            245                 250                 255

Ser Val Tyr Asp Ala Val Arg Glu Arg Phe Ala Thr His Gly Gly Tyr
        260                 265                 270

Leu Leu Gln Gly Lys Glu Leu Lys Ala Val Gln Asp Val Ile Leu Lys
    275                 280                 285

Asn Gly Ala Leu Asn Ala Ala Ile Val Gly Gln Pro Ala Tyr Lys Ile
290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
            325                 330                 335

Leu Ser Pro Thr Leu Ala Met Tyr Arg Ala Lys Asp Phe Glu Asp Ala
        340                 345                 350

Val Glu Lys Ala Glu Lys Leu Val Ala Met Gly Gly Ile Gly His Thr
    355                 360                 365

Ser Cys Leu Tyr Thr Asp Gln Asp Asn Gln Pro Ala Arg Val Ser Tyr
370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
            405                 410                 415

Leu Thr Leu Gly Cys Gly Ser Trp Gly Gly Asn Ser Ile Ser Glu Asn
        420                 425                 430

Val Gly Pro Lys His Leu Ile Asn Lys Lys Thr Val Ala Lys Arg Ala
    435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
            485                 490                 495

Asp Gln Ile Thr Ser Val Leu Lys Ala Ala Gly Val Glu Thr Glu Val
        500                 505                 510

Phe Phe Glu Val Glu Ala Asp Pro Thr Leu Ser Ile Val Arg Lys Gly
    515                 520                 525

Ala Glu Leu Ala Asn Ser Phe Lys Pro Asp Val Ile Ile Ala Leu Gly
530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
            565                 570                 575

Arg Lys Arg Ile Tyr Lys Phe Pro Lys Met Gly Val Lys Ala Lys Met
        580                 585                 590

Ile Ala Val Thr Thr Thr Ser Gly Thr Gly Ser Glu Val Thr Pro Phe
    595                 600                 605

Ala Val Val Thr Asp Asp Ala Thr Gly Gln Lys Tyr Pro Leu Ala Asp
610                 615                 620

Tyr Ala Leu Thr Pro Asp Met Ala Ile Val Asp Ala Asn Leu Val Met
625                 630                 635                 640
```

```
Asp Met Pro Lys Ser Leu Cys Ala Phe Gly Gly Leu Asp Ala Val Thr
            645                 650                 655

His Ala Met Glu Ala Tyr Val Ser Val Leu Ala Ser Glu Phe Ser Asp
        660                 665                 670

Gly Gln Ala Leu Gln Ala Leu Lys Leu Leu Lys Glu Tyr Leu Pro Ala
        675                 680                 685

Ser Tyr His Glu Gly Ser Lys Asn Pro Val Ala Arg Glu Arg Val His
        690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
            725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Tyr Ala Glu Ile Ala Asp His Leu Gly Leu
        770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
            805                 810                 815

Glu Ala Gly Val Gln Glu Ala Asp Phe Leu Ala Asn Val Asp Lys Leu
                820                 825                 830

Ser Glu Asp Ala Phe Asp Gln Cys Thr Gly Ala Asn Pro Arg Tyr
        835                 840                 845

Pro Leu Ile Ser Glu Leu Lys Gln Ile Leu Leu Asp Thr Tyr Tyr Gly
850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
            885                 890

<210> SEQ ID NO 47
<211> LENGTH: 2685
<212> TYPE: DNA
<213> ORGANISM: Pantoea ananatis

<400> SEQUENCE: 47
atggccgtta ctaatgtcgc tgaactcaat gcactggttg aacgtgtaaa aaaagcccag      60
caagaattcg ccaattttc tcaacaacag gtcgatgcca tcttccgcgc agccgcactg     120
gccgccgcgg atgcccgaat tccactcgct aaaatggcgg tggcagaatc gggcatgggc     180
attgttgaag acaaagtcat taaaaatcac ttcgcttctg aatacatcta caacgcctat     240
aaggatgaga aacctgcgg cgtactggac accgatgata cgtttggcac catcacaatc     300
gctgaaccca tcggcctgat tgcggtatc gtccccacca ctaaccctac ctccaccgcg     360
attttcaagg cacttatcag ccttaaaacc cgcaacggga ttatcttctc cccccatcct     420
cgagccaaag atgcgacgaa caaagcggcg gatattgtcc tgcaggcagc gattgccgct     480
ggcgcgccca agacatatat aggctggatt gatgcacctt ctgtggaact gtccaatcag     540
ttgcaccatc ctgatattaa cctgattctg gcgacgggtg gccccggcat ggtcaaagcc     600
gcctacagct caggtaagcc ggcgattggc gtggggccg gtaacaccgc cgttgtcatc     660
gatgaaacag ctgatgttaa acgcgccgtt gcctccatcc tgatgtcaaa aacgtttgat     720
```

```
aacggtgtga tctgtgcctc tgaacagtcg gttatcgtgg tggatgccgt ctacgacgcc    780
gtgcgcgagc gcttcgccag ccatggtggc tatttgcttc agggacagga actgagtgcg    840
gtacaaaata tcattctaaa aaacggtggg cttaacgccg ccattgtggg ccagcctgcg    900
gtgaagattg cggagatggc cggcatcagc gtacctggtg aaaccaaaat cctgattggc    960
gaagttgaac gggtcgatga atcagagcct ttcgctcatg aaaaactgtc gccgacactg   1020
gcgatgtacc gtgctaaaga ttatcaggat gccgtcagca agcgagaaa actggtggcg   1080 atgggtggta ttggtcatac gtcatgcctg tataccgacc aggacaatca gacagcgcgc   1140
gtgcactatt ttggcgacaa gatgaaaaca gcccgcattc tgatcaacac gccagcttct   1200
cagggcggta ttggtgattt atataacttc aaactcgccc cttctctgac actgggttgt   1260
ggttcctggg gcgtaactc catttctgaa acgtggggc ccaaacatct catcaacaag   1320
aaaaccgtcg ctaagcgagc tgaaaatatg ttgtggcata acttccgaa gtccatttac   1380 ttccgtcgcg gctctttacc cattgcgctt gaagagatcg ccaccgacgg tgccaaacgc   1440
gcgtttgtgg tgactgaccg cttcctgttt aacaacggtt atgccgatca ggtcacccgc   1500 gtttttaaaat ctcacggcat cgaaaccgaa gtttctcttg aggttgaagc ggatcccacc   1560
ttaagcatcg tgcgtaaagg tgcagaacag atgaacagct ttaagccaga cgtgatcatc   1620
gccctgggcg gcggttcgcc gatggatgca gccaaaatca tgtgggtcat gtatgagcat   1680
cctgaaaccc attttgaaga gctggcactg cggtttatgg atattcgcaa acgtatctat   1740
aagttcccta aaatgggcgt gaaagcgcgc atggtggcca ttacgacaac ctcaggcaca   1800
ggttcagaag tgacgccttt tgccgtggta acgatgacg cgaccggaca gaaatacccg   1860
ctggccgatt atgcgctgac gccggatatg gctatcgttg atgccaacct ggtcatggat   1920
atgccacgtt cactctgtgc cttcggcggt ctggatgcgg tgacgcacgc gctggaagcc   1980
tatgtgtccg tcctggccaa tgaatactcc gatggtcagg ccctgcaggc gcttaagctg   2040
cttaaagaga acttaccggc gagttatgca gaaggtgcaa aaaatccggt tgcccgtgaa   2100
cgtgtacata atgccgccac catcgccggt atcgcctttg cgaacgcctt cctcggggtt   2160
tgtcactcaa tggcgcataa gcttggctct gagttccata ttcctcatgg actggctaac   2220
tcgctgctga tttccaacgt tattcgctat aacgccaatg acaaccctac taagcaaacc   2280
gcattcagcc agtacgatcg tcccccaggcg cgtcgtcgtt atgctgaaat tgcggatcat   2340
cttggtctca ccgcgccggg cgaccgcact gcccagaaaa ttgagaagct gctggtatgg   2400
ctggatgaaa tcaaaacgga actgggtatt ccggcctcaa ttcgtgaagc cggtgtgcag   2460
gaggctgact tcctggcgaa agtcgataaa ctggcggatg atgcctttga tgaccagtgt   2520
actggcgcga atcacgttta ccgctgatt gccgaactca aacagctgat gctggacagc   2580
tactacggac gcaaatttgt cgagccgttc gccagtgccg ccgaggctgc ccaggctcag   2640
cctgtcagtg acagcaaagc ggcgaagaaa gctaaaaaag cctaa                     2685
```

<210> SEQ ID NO 48
<211> LENGTH: 894
<212> TYPE: PRT
<213> ORGANISM: Pantoea ananatis

<400> SEQUENCE: 48

```
Met Ala Val Thr Asn Val Ala Glu Leu Asn Ala Leu Val Glu Arg Val
1               5                   10                  15

Lys Lys Ala Gln Gln Glu Phe Ala Asn Phe Ser Gln Gln Gln Val Asp
            20                  25                  30
```

```
Ala Ile Phe Arg Ala Ala Ala Leu Ala Ala Asp Ala Arg Ile Pro
         35                  40                  45
Leu Ala Lys Met Ala Val Ala Glu Ser Gly Met Gly Ile Val Glu Asp
 50                  55                  60
Lys Val Ile Lys Asn His Phe Ala Ser Glu Tyr Ile Tyr Asn Ala Tyr
 65                  70                  75                  80
Lys Asp Glu Lys Thr Cys Gly Val Leu Asp Thr Asp Thr Phe Gly
             85                  90                  95
Thr Ile Thr Ile Ala Glu Pro Ile Gly Leu Ile Cys Gly Ile Val Pro
                100                 105                 110
Thr Thr Asn Pro Thr Ser Thr Ala Ile Phe Lys Ala Leu Ile Ser Leu
            115                 120                 125
Lys Thr Arg Asn Gly Ile Ile Phe Ser Pro His Pro Arg Ala Lys Asp
        130                 135                 140
Ala Thr Asn Lys Ala Ala Asp Ile Val Leu Gln Ala Ala Ile Ala Ala
145                 150                 155                 160
Gly Ala Pro Lys Asp Ile Ile Gly Trp Ile Asp Ala Pro Ser Val Glu
                165                 170                 175
Leu Ser Asn Gln Leu His His Pro Asp Ile Asn Leu Ile Leu Ala Thr
            180                 185                 190
Gly Gly Pro Gly Met Val Lys Ala Ala Tyr Ser Ser Gly Lys Pro Ala
        195                 200                 205
Ile Gly Val Gly Ala Gly Asn Thr Pro Val Val Ile Asp Glu Thr Ala
        210                 215                 220
Asp Val Lys Arg Ala Val Ala Ser Ile Leu Met Ser Lys Thr Phe Asp
225                 230                 235                 240
Asn Gly Val Ile Cys Ala Ser Glu Gln Ser Val Ile Val Val Asp Ala
                245                 250                 255
Val Tyr Asp Ala Val Arg Glu Arg Phe Ala Ser His Gly Gly Tyr Leu
            260                 265                 270
Leu Gln Gly Gln Glu Leu Ser Ala Val Gln Asn Ile Ile Leu Lys Asn
        275                 280                 285
Gly Gly Leu Asn Ala Ala Ile Val Gly Gln Pro Ala Val Lys Ile Ala
        290                 295                 300
Glu Met Ala Gly Ile Ser Val Pro Gly Glu Thr Lys Ile Leu Ile Gly
305                 310                 315                 320
Glu Val Glu Arg Val Asp Glu Ser Glu Pro Phe Ala His Glu Lys Leu
                325                 330                 335
Ser Pro Thr Leu Ala Met Tyr Arg Ala Lys Asp Tyr Gln Asp Ala Val
            340                 345                 350
Ser Lys Ala Glu Lys Leu Val Ala Met Gly Gly Ile Gly His Thr Ser
        355                 360                 365
Cys Leu Tyr Thr Asp Gln Asp Asn Gln Thr Ala Arg Val His Tyr Phe
        370                 375                 380
Gly Asp Lys Met Lys Thr Ala Arg Ile Leu Ile Asn Thr Pro Ala Ser
385                 390                 395                 400
Gln Gly Gly Ile Gly Asp Leu Tyr Asn Phe Lys Leu Ala Pro Ser Leu
                405                 410                 415
Thr Leu Gly Cys Gly Ser Trp Gly Gly Asn Ser Ile Ser Glu Asn Val
            420                 425                 430
Gly Pro Lys His Leu Ile Asn Lys Lys Thr Val Ala Lys Arg Ala Glu
        435                 440                 445
```

```
Asn Met Leu Trp His Lys Leu Pro Lys Ser Ile Tyr Phe Arg Arg Gly
    450                 455                 460
Ser Leu Pro Ile Ala Leu Glu Glu Ile Ala Thr Asp Gly Ala Lys Arg
465                 470                 475                 480
Ala Phe Val Val Thr Asp Arg Phe Leu Phe Asn Asn Gly Tyr Ala Asp
                485                 490                 495
Gln Val Thr Arg Val Leu Lys Ser His Gly Ile Glu Thr Glu Val Phe
            500                 505                 510
Phe Glu Val Glu Ala Asp Pro Thr Leu Ser Ile Val Arg Lys Gly Ala
        515                 520                 525
Glu Gln Met Asn Ser Phe Lys Pro Asp Val Ile Ala Leu Gly Gly
530                 535                 540
Gly Ser Pro Met Asp Ala Ala Lys Ile Met Trp Val Met Tyr Glu His
545                 550                 555                 560
Pro Glu Thr His Phe Glu Glu Leu Ala Leu Arg Phe Met Asp Ile Arg
                565                 570                 575
Lys Arg Ile Tyr Lys Phe Pro Lys Met Gly Val Lys Ala Arg Met Val
            580                 585                 590
Ala Ile Thr Thr Thr Ser Gly Thr Gly Ser Glu Val Thr Pro Phe Ala
        595                 600                 605
Val Val Thr Asp Asp Ala Thr Gly Gln Lys Tyr Pro Leu Ala Asp Tyr
610                 615                 620
Ala Leu Thr Pro Asp Met Ala Ile Val Asp Ala Asn Leu Val Met Asp
625                 630                 635                 640
Met Pro Arg Ser Leu Cys Ala Phe Gly Gly Leu Asp Ala Val Thr His
                645                 650                 655
Ala Leu Glu Ala Tyr Val Ser Val Leu Ala Asn Glu Tyr Ser Asp Gly
            660                 665                 670
Gln Ala Leu Gln Ala Leu Lys Leu Leu Lys Glu Asn Leu Pro Ala Ser
        675                 680                 685
Tyr Ala Glu Gly Ala Lys Asn Pro Val Ala Arg Glu Arg Val His Asn
690                 695                 700
Ala Ala Thr Ile Ala Gly Ile Ala Phe Ala Asn Ala Phe Leu Gly Val
705                 710                 715                 720
Cys His Ser Met Ala His Lys Leu Gly Ser Glu Phe His Ile Pro His
                725                 730                 735
Gly Leu Ala Asn Ser Leu Leu Ile Ser Asn Val Ile Arg Tyr Asn Ala
            740                 745                 750
Asn Asp Asn Pro Thr Lys Gln Thr Ala Phe Ser Gln Tyr Asp Arg Pro
        755                 760                 765
Gln Ala Arg Arg Arg Tyr Ala Glu Ile Ala Asp His Leu Gly Leu Thr
770                 775                 780
Ala Pro Gly Asp Arg Thr Ala Gln Lys Ile Glu Lys Leu Leu Val Trp
785                 790                 795                 800
Leu Asp Glu Ile Lys Thr Glu Leu Gly Ile Pro Ala Ser Ile Arg Glu
                805                 810                 815
Ala Gly Val Gln Glu Ala Asp Phe Leu Ala Lys Val Asp Lys Leu Ala
            820                 825                 830
Asp Asp Ala Phe Asp Asp Gln Cys Thr Gly Ala Asn Pro Arg Tyr Pro
        835                 840                 845
Leu Ile Ala Glu Leu Lys Gln Leu Met Leu Asp Ser Tyr Tyr Gly Arg
850                 855                 860
```

| Lys | Phe | Val | Glu | Pro | Phe | Ala | Ser | Ala | Ala | Glu | Ala | Ala | Gln | Ala | Gln |
|---|---|---|---|---|---|---|---|---|---|---|---|---|---|---|---|
| 865 | | | | 870 | | | | 875 | | | | 880 | | | |

| Pro | Val | Ser | Asp | Ser | Lys | Ala | Ala | Lys | Lys | Ala | Lys | Lys | Ala |
|---|---|---|---|---|---|---|---|---|---|---|---|---|---|
| | | | 885 | | | | 890 | | | | | | |

<210> SEQ ID NO 49
<211> LENGTH: 2676
<212> TYPE: DNA
<213> ORGANISM: Pectobacterium atrosepticum

<400> SEQUENCE: 49

```
atggccgtaa ccaacgttgc tgaacttaac gcactggtcg aaagagttaa aaaggcacag      60
caggaatttg ccacttacac tcaggaacaa gtggacaaga tcttccgcgc tgccgcactc     120
gctgcatcgg atgcccgtat cccgctggca aaaatggcgg ttgctgaatc cggtatgggg     180
atcgtggaag ataaagtcat caaaaaccac ttcgcatccg aatacattta taacgcctat     240
caggatgaaa aaacctgtgg cgtcctctct actgatgaca ctttcggtac tattaccatt     300
gcagagccta ttggcctgat ttgcggtatt gttcccacca ccaaccccac ttctaccgcg     360
atttttaaag cgctgatcag cctgaagact cgtaacggga ttatcttctc tccccatcca     420
cgtgcaaaaa atgcgaccaa taaagccgca gacattgtac tgcaagctgc gattgccgct     480
ggcgccccga agatatcat cggctggatt gatcaaccgt ccgtcgattt atccaaccaa     540
ctgatgcacc acccagatat caacctgatt ctggctaccg gcgggccggg tatggtgaaa     600
gcggcataca gctcaggtaa accggcgatc ggcgtaggtg caggtaacac ccccgttgtt     660
attgacgaaa cggcggatat taagcgtgcc gttgcctcta tcctgatgtc gaaaaccttc     720
gataacggcg tcatttgtgc gtcagaacag tcagtcatcg tggtagacag cgcctatgat     780
gccgtacgtg agcgtttcgc cacccacggc ggctacatgc tgaaaggcaa agaacttcat     840
gccgtacaag gcattctgct gaaaaacggc tcactgaatg ccgacattgt gggccagcca     900
gcaccaaaga tcgctgaaat ggcgggtatc accgtccctg cgaacaccaa agtgctgatc     960
ggtgaagtga cggccgttga tgaatccgaa ccgtttgccc atgaaaaact gtctccgacg    1020
ctggcgatgt accgggcgaa agacttcaat gacgccgtca ttaaagcgga aaaactggtg    1080
gcaatgggtg gcatcggtca cacatcctgc ctgtataccg atcaggacaa tcagccagag    1140
cgtgtaaatc atttcgggaa tatgatgaaa acggcacgta tcctgattaa cacgccggct    1200
tctcagggtg gtatcggcga tctctacaac ttcaaactcg ctccgtctct gacactgggc    1260
tgtggctcat ggggcggaaa ctccatctcc gaaaacgtcg gtccgaagca cttgatcaac    1320
aaaaaaacgg tagccaagcg agcagagaat atgttgtggc ataaacttcc taaatccatt    1380
tacttccgtc gtggctcact gcctatcgca cttgaagaag tcgcatccga tggtgcaaaa    1440
cgcgcattta tcgtgactga ccgcttcctg ttcaataatg gctacgttga tcaggtaact    1500
tccgtactga acaacacgg actggaaacc gaagttttct ttgaagttga agctgacccg    1560
acactgagca tcgtgcgcaa aggcgcggaa caaatgcact ccttcaagcc cgatgtgatt    1620
attgcactgg gtggcggttc tccgatggat gctgcgaaga tcatgtgggt gatgtatgag    1680
caccctacta cacacttcga agagctgcg ctgcgcttta tggatatccg taaacgtatc    1740
tataagttcc cgaaaatggg tgtcaaagcc aagatggtgg cgattaccac tacatccggt    1800
actggttccg aagtcacgcc atttgccgtg tgaccgacg atgcaactgg acagaaatat    1860
ccgttggcg actatgcgct gaccccagat atggccattg ttgatgccaa tctggtgatg    1920
aacatgccga atcgctgtg tgcctttggt gggctcgatg ccgtaaccca ctcgctggaa    1980
```

-continued

```
gcctatgttt ccgtgctggc aaatgaatat tcagacggac aggcgttaca agcgctgaaa      2040
ctgctgaagg aaaatctgcc ggacagctac cgtgacggtg cgaaaaaccc ggttgcccgt      2100
gagcgcgtgc acaacgccgc gacgattgcg ggtatcgcgt tgccaacgc cttcctcggc       2160 gtctgtcact caatggcgca taaactgggc tcggagttcc atattccgca cggtctggct      2220
aatgccatgc tgatctcgaa cgtgattcgc tataacgcga acgataaccc gaccaaacaa      2280
acaacgttca gccaatatga ccgtccgcaa gctcgtcgtc gttacgctga aatagccgac      2340
cacctacgtt tgactgcgcc tagcgaccgt actgcacaga aaatcgagaa attactgaac      2400
tggctggaag aaataaagac cgaactgggg atcccagcgt ccattcgtga agcgggcgta      2460
caggaggccg atttcctggc taaggtcgat aaactgtcag aagatgcgtt cgacgatcag      2520
tgtactggtg ctaacccacg ctacccgctg atttctgaat tgaaacagat tctgctggac      2580
acttactatg gtcgtaagtt ctctgaagag gtaaaaacgg aaaccgttga acctgtagca      2640
aaagccgcca aaccggcaa gaaagccgca cattaa                                 2676
```

<210> SEQ ID NO 50
<211> LENGTH: 891
<212> TYPE: PRT
<213> ORGANISM: Pectobacterium atrosepticum

<400> SEQUENCE: 50

```
Met Ala Val Thr Asn Val Ala Glu Leu Asn Ala Leu Val Glu Arg Val
1               5                   10                  15

Lys Lys Ala Gln Gln Glu Phe Ala Thr Tyr Thr Gln Glu Gln Val Asp
            20                  25                  30

Lys Ile Phe Arg Ala Ala Ala Leu Ala Ala Ser Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Gln Asp Glu Lys Thr Cys Gly Val Leu Ser Thr Asp Thr Phe Gly
                85                  90                  95

Thr Ile Thr Ile Ala Glu Pro Ile Gly Leu Ile Cys Gly Ile Val Pro
            100                 105                 110

Thr Thr Asn Pro Thr Ser Thr Ala Ile Phe Lys Ala Leu Ile Ser Leu
        115                 120                 125

Lys Thr Arg Asn Gly Ile Ile Phe Ser Pro His Pro Arg Ala Lys Asn
    130                 135                 140

Ala Thr Asn Lys Ala Ala Asp Ile Val Leu Gln Ala Ala Ile Ala Ala
145                 150                 155                 160

Gly Ala Pro Lys Asp Ile Ile Gly Trp Ile Asp Gln Pro Ser Val Asp
                165                 170                 175

Leu Ser Asn Gln Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Ile Asp Glu Thr
    210                 215                 220

Ala Asp Ile Lys Arg Ala Val Ala Ser Ile Leu Met Ser Lys Thr Phe
225                 230                 235                 240

Asp Asn Gly Val Ile Cys Ala Ser Glu Gln Ser Val Ile Val Val Asp
                245                 250                 255
```

```
Ser Ala Tyr Asp Ala Val Arg Glu Arg Phe Ala Thr His Gly Gly Tyr
            260                 265                 270

Met Leu Lys Gly Lys Glu Leu His Ala Val Gln Gly Ile Leu Leu Lys
            275                 280                 285

Asn Gly Ser Leu Asn Ala Asp Ile Val Gly Gln Pro Ala Pro Lys Ile
            290                 295                 300

Ala Glu Met Ala Gly Ile Thr Val Pro Ala Asn Thr Lys Val Leu Ile
305                 310                 315                 320

Gly Glu Val Thr Ala Val Asp Glu Ser Glu Pro Phe Ala His Glu Lys
                    325                 330                 335

Leu Ser Pro Thr Leu Ala Met Tyr Arg Ala Lys Asp Phe Asn Asp Ala
            340                 345                 350

Val Ile Lys Ala Glu Lys Leu Val Ala Met Gly Gly Ile Gly His Thr
            355                 360                 365

Ser Cys Leu Tyr Thr Asp Gln Asp Asn Gln Pro Glu Arg Val Asn His
            370                 375                 380

Phe Gly Asn Met Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                    405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
            435                 440                 445

Glu Asn Met Leu Trp His Lys Leu Pro Lys Ser Ile Tyr Phe Arg Arg
            450                 455                 460

Gly Ser Leu Pro Ile Ala Leu Glu Glu Val Ala Ser Asp Gly Ala Lys
465                 470                 475                 480

Arg Ala Phe Ile Val Thr Asp Arg Phe Leu Phe Asn Asn Gly Tyr Val
                    485                 490                 495

Asp Gln Val Thr Ser Val Leu Lys Gln His Gly Leu Glu Thr Glu Val
            500                 505                 510

Phe Phe Glu Val Glu Ala Asp Pro Thr Leu Ser Ile Val Arg Lys Gly
            515                 520                 525

Ala Glu Gln Met His Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Thr Thr His Phe Glu Glu Leu Ala Leu Arg Phe Met Asp Ile
                    565                 570                 575

Arg Lys Arg Ile Tyr Lys Phe Pro Lys Met Gly Val Lys Ala Lys Met
            580                 585                 590

Val Ala Ile Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asn Met Pro Lys Ser Leu Cys Ala Phe Gly Gly Leu Asp Ala Val Thr
                    645                 650                 655

His Ser Leu Glu Ala Tyr Val Ser Val Leu Ala Asn Glu Tyr Ser Asp
            660                 665                 670
```

Gly Gln Ala Leu Gln Ala Leu Lys Leu Leu Lys Glu Asn Leu Pro Asp
            675                 680                 685

Ser Tyr Arg Asp Gly Ala Lys Asn Pro Val Ala Arg Glu Arg Val His
    690                 695                 700

Asn Ala Ala Thr Ile Ala Gly Ile Ala Phe Ala Asn Ala Phe Leu Gly
705                 710                 715                 720

Val Cys His Ser Met Ala His Lys Leu Gly Ser Glu Phe His Ile Pro
                725                 730                 735

His Gly Leu Ala Asn Ala Met Leu Ile Ser Asn Val Ile Arg Tyr Asn
            740                 745                 750

Ala Asn Asp Asn Pro Thr Lys Gln Thr Thr Phe Ser Gln Tyr Asp Arg
    755                 760                 765

Pro Gln Ala Arg Arg Tyr Ala Glu Ile Ala Asp His Leu Arg Leu
    770                 775                 780

Thr Ala Pro Ser Asp Arg Thr Ala Gln Lys Ile Glu Lys Leu Leu Asn
785                 790                 795                 800

Trp Leu Glu Glu Ile Lys Thr Glu Leu Gly Ile Pro Ala Ser Ile Arg
                805                 810                 815

Glu Ala Gly Val Gln Glu Ala Asp Phe Leu Ala Lys Val Asp Lys Leu
            820                 825                 830

Ser Glu Asp Ala Phe Asp Asp Gln Cys Thr Gly Ala Asn Pro Arg Tyr
    835                 840                 845

Pro Leu Ile Ser Glu Leu Lys Gln Ile Leu Leu Asp Thr Tyr Tyr Gly
    850                 855                 860

Arg Lys Phe Ser Glu Glu Val Lys Thr Glu Thr Val Glu Pro Val Ala
865                 870                 875                 880

Lys Ala Ala Lys Thr Gly Lys Lys Ala Ala His
                885                 890

<210> SEQ ID NO 51
<211> LENGTH: 2679
<212> TYPE: DNA
<213> ORGANISM: Salmonella enterica

<400> SEQUENCE: 51
atggctgtta ctaatgtcgc tgaacttaac gcactcgtag agcgtgtaaa aaaagcccag      60
cgtgaatatg ccagtttcac tcaagaacag gtcgacaaaa tcttccgcgc cgccgctctg     120
gcagccgctg atgcccgcat tccgctggcc aaaatggccg tcgccgaatc aggtatgggt     180
atcgtggaag acaaagtgat taaaaaccac ttcgcttctg aatatattta caatgcctat     240
aaagatgaaa aacctgcggc gtgctgtca gaagacgaca ccttcgggac catcaccatt     300
gctgaaccta tcggcattat ttgcggtatc gttccaacca ctaacccgac ctctactgcg     360
atcttcaaat cgctgattag cctgaagacc cgtaacgcca tcatcttttc tccgcatccg     420
cgcgctaaag aagcaactaa caaagcggca gacatcgttc tgcaagcggc tatcgctgcc     480
ggcgcaccga agatctgat tggctggatc gatcaacctt ccgtagaact gtctaatgcg     540
ctgatgcacc acccggatat taacctgatc ctcgccactg gcggtccagg catggttaaa     600
gctgcataca gctccggtaa accggcaatc ggcgtaggcg caggtaacac cccgttgtc     660 attgatgaaa ccgctgatat caaacgcgct gtggcgtctg ttctgatgtc taaaaccttc     720
gataacggcg taatctgtgc ttctgaacag tctgttgtcg ttgttgattc cgtctatgat     780
gccgttcgcg aacgtttcgc cagccacggc ggctacatgc tgcagggcca ggagctgaaa     840
gcggttcaaa acgttattct gaaaaatggc gctctgaacg ccgctatcgt cggtcagcca     900

```
gcctacaaaa tcgctgaact ggcaggcttc tccgtaccag aaaccaccaa gattctgatc    960
ggtgaagtta cggtcgttga cgaaagcgaa ccgttcgcac acgaaaaact gtctccgact   1020
ctagcgatgt accgtgcgaa agatttcgaa gaagcggtag aaaaagcaga aaactggtc    1080
gctatgggcg gtatcggtca cacctcctgc ctgtacactg accaggataa ccagccagaa   1140
cgcgttgctt acttcggtca gatgatgaaa accgcgcgta tcctgatcaa caccccggcc   1200
tctcagggtg gtatcggtga cctgtacaac ttcaaactcg caccttccct gacgttgggt   1260
tgtggttcct ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctctct gcccatcgcg ctggatgaag tgattactga tggccacaaa   1440
cgtgcgctca tcgtgactga ccgcttcctg ttcaacaacg gctatgcaga ccagatcacc   1500
tctgtgctga aagcggctgg cgttgaaacc gaagtcttct tcgaagttga agcagacccg   1560
acgctttccg ttgttcgcaa aggcgctgag ctggctaact ccttcaaacc ggacgtgatc   1620
atcgcgctgg gcggcggttc cccgatggac gccgcgaaaa tcatgtgggt catgtacgaa   1680
catccggaaa ctcacttcga gaactggcg ctgcgcttta tggacatccg taaacgtatc   1740
tacaagttcc cgaaaatggg cgtgaaagcg aaaatgatcg ccgtcaccac cacttccggt   1800
accggttctg aagtcacacc gtttgcggtt gtgaccgaca atgcaaccgg tcagaaatat   1860
ccgctggctg actatgccct gaccccggat atggcgattg tcgatgccaa cctggtgatg   1920
gatatgccga agtccctgtg tgcgttcggt ggtctggatg cggtaactca cgccctggaa   1980
gcttacgttt ccgtactggc ttctgagttc tctgacggtc aggctctgca ggctctgaaa   2040
ctgctgaaag aaaacctgcc ggcgtcttac acgaagggt ctaaaaaccc ggttgcgcgt   2100
gaacgtgttc acagtgcagc gactatcgcc ggtatcgcgt ttgccaacgc cttcctcggt   2160
gtatgtcact ccatggcgca caaactgggc tctcagttcc acattccgca cggtctggcg   2220
aacgccctgc tgatttgtaa cgttatccgc tacaacgcga atgacaaccc gaccaagcag   2280
accgctttca gccagtacga tcgtccgcag gcacgccgtc gttacgctga aattgctgac   2340
cacctgggcc tgagcgcgcc gggcgaccgt accgccgcta agattgaaaa actgctggca   2400
tggctggaaa gcattaaagc tgagctgggc attcctaagt ctatacgtga agcaggcgtg   2460
caggaagctg acttcctggc acacgttgac aaactgtctg aagatgcctt cgatgaccag   2520
tgcaccggcg ctaacccgcg ttatccgctg atctccgaac tgaaacagat tctgctggat   2580
acctactacg tcgtgatttt caccgaaggt gaagttgcag cgaagaaaga cgtcgttgcc   2640
gcaccgaaag cagagaaaaa agcgaaaaaa tccgcttaa                          2679
```

<210> SEQ ID NO 52
<211> LENGTH: 892
<212> TYPE: PRT
<213> ORGANISM: Salmonella enterica

<400> SEQUENCE: 52

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60
```

```
Lys Val Ile Lys Asn His Phe Ala Ser Glu Tyr Ile Tyr Asn Ala Tyr
 65                  70                  75                  80

Lys Asp Glu Lys Thr Cys Gly Val Leu Ser Glu Asp Thr Phe Gly
                 85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
            115                 120                 125

Lys Thr Arg Asn Ala Ile Ile Phe Ser Pro His Pro Arg Ala Lys Glu
        130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
                180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Ile Asp Glu Thr
        210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Ser His Gly Gly Tyr
            260                 265                 270

Met Leu Gln Gly Gln Glu Leu Lys Ala Val Gln Asn Val Ile Leu Lys
        275                 280                 285

Asn Gly Ala Leu Asn Ala Ala Ile Val Gly Gln Pro Ala Tyr Lys Ile
290                 295                 300

Ala Glu Leu Ala Gly Phe Ser Val Pro Glu Thr Thr Lys Ile Leu Ile
305                 310                 315                 320

Gly Glu Val Thr Val Val Asp Glu Ser Glu Pro Phe Ala His Glu Lys
            325                 330                 335

Leu Ser Pro Thr Leu Ala Met Tyr Arg Ala Lys Asp Phe Glu Glu Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Glu Arg Val Ala Tyr
370                 375                 380

Phe Gly Gln Met Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
450                 455                 460

Gly Ser Leu Pro Ile Ala Leu Asp Glu Val Ile Thr Asp Gly His Lys
465                 470                 475                 480
```

```
Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Val Val Arg Lys Gly
            515                 520                 525

Ala Glu Leu Ala Asn Ser Phe Lys Pro Asp Val Ile Ile Ala Leu Gly
            530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
                565                 570                 575

Arg Lys Arg Ile Tyr Lys Phe Pro Lys Met Gly Val Lys Ala Lys Met
            580                 585                 590

Ile Ala Val Thr Thr Thr Ser Gly Thr Gly Ser Glu Val Thr Pro Phe
            595                 600                 605

Ala Val Val Thr Asp Asn Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                645                 650                 655

His Ala Leu Glu Ala Tyr Val Ser Val Leu Ala Ser Glu Phe Ser Asp
                660                 665                 670

Gly Gln Ala Leu Gln Ala Leu Lys Leu Leu Lys Glu Asn Leu Pro Ala
            675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
            740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Lys Ile Glu Lys Leu Leu Ala
785                 790                 795                 800

Trp Leu Glu Ser Ile Lys Ala Glu Leu Gly Ile Pro Lys Ser Ile Arg
                805                 810                 815

Glu Ala Gly Val Gln Glu Ala Asp Phe Leu Ala His Val Asp Lys Leu
            820                 825                 830

Ser Glu Asp Ala Phe Asp Asp Gln Cys Thr Gly Ala Asn Pro Arg Tyr
            835                 840                 845

Pro Leu Ile Ser Glu Leu Lys Gln Ile Leu Leu Asp Thr Tyr Tyr Gly
            850                 855                 860

Arg Asp Phe Thr Glu Gly Glu Val Ala Ala Lys Lys Asp Val Val Ala
865                 870                 875                 880

Ala Pro Lys Ala Glu Lys Lys Ala Lys Lys Ser Ala
                885                 890
```